(12) United States Patent
Caldirola et al.

(10) Patent No.: US 7,144,883 B2
(45) Date of Patent: Dec. 5, 2006

(54) BICYCLIC SULFONAMIDE COMPOUNDS

(75) Inventors: Patrizia Caldirola, Uppsala (SE); Gary Johansson, Uppsala (SE); Andrew Mott, Knivsta (SE); Katarina Beierlien, Uppsala (SE); Markus Thor, Knivsta (SE); Lars Tedenborg, Uppsala (SE); Ulf Bremberg, Uppsala (GB); Annika Jenmalm Jensen, Uppsala (SE)

(73) Assignee: Biovitrum AB, Stockholm (SE)

( * ) Notice: Subject to any disclaimer, the term of this patent is extended or adjusted under 35 U.S.C. 154(b) by 289 days.

(21) Appl. No.: 10/167,141

(22) Filed: Jun. 11, 2002

(65) Prior Publication Data

US 2003/0158202 A1 Aug. 21, 2003

(30) Foreign Application Priority Data

| Jun. 11, 2001 | (SE) | ................................... 0102048 |
| Jul. 3, 2001 | (SE) | ................................... 0102386 |
| Oct. 16, 2001 | (SE) | ................................... 0103437 |

(51) Int. Cl.
  A61P 3/04   (2006.01)
  A61P 7/00   (2006.01)
  A61K 31/42  (2006.01)
  A61K 31/445 (2006.01)
  A61K 31/497 (2006.01)

(52) U.S. Cl. .............. 514/254.11; 514/218; 514/249; 514/252.13; 514/253.06; 514/254.04; 514/254.06; 514/254.08; 514/254.09; 514/320; 514/321; 514/322; 514/323; 514/324; 514/367; 514/373; 514/375; 514/379; 514/393; 514/403; 514/414; 540/575; 544/349; 544/363; 544/368; 544/370; 544/371; 544/373; 544/376; 544/377; 546/196; 546/197; 546/198; 546/199; 546/201; 546/202

(58) Field of Classification Search ............... 544/363, 544/368, 376; 514/253.06, 254.11
See application file for complete search history.

(56) References Cited

U.S. PATENT DOCUMENTS 4,808,595 A   2/1989 Hoffman, Jr. ................ 514/302

FOREIGN PATENT DOCUMENTS

| EP | 0 701 819 | 3/1996 |
| EP | 0 815 861 | 1/1998 |
| EP | 1 020 445 | 7/2000 |
| GB | 947606 | 1/1964 |
| WO | WO 84/01151 | 3/1984 |
| WO | WO 94/21619 | 9/1994 |
| WO | WO 98/27081 | 6/1998 |
| WO | WO 9827081 A1 * | 6/1998 |
| WO | WO 99/02502 | 1/1999 |
| WO | WO 99/37623 | 7/1999 |
| WO | WO 99/42465 | 8/1999 |
| WO | WO 00/12073 | 3/2000 |
| WO | WO 00/55159 | 9/2000 |
| WO | WO 01/32646 | 5/2001 |
| WO | WO 01/32660 A1 | 5/2001 |
| WO | WO 200132646 A2 * | 5/2001 |
| WO | WO 01/85722 | 11/2001 |
| WO | WO 01/96336 | 12/2001 |
| WO | WO 02/32863 | 4/2002 |
| WO | WO 02/092585 | 11/2002 |
| WO | WO 02/098857 | 12/2002 |
| WO | WO 02/100822 | 12/2002 |

OTHER PUBLICATIONS

STN International, file CAPLUS, CAPLUS Accession No. 1970:509549, document No. 73:109549, Werbel, Leslie M. et al: Synthetic schistosomicides . . . J. Med. Chem 13(4):592-598, 1970.
Methvin Isaac et al., "6-Bicyclopiperazinyl-1-arylsulfonylindoles and 6-Bicyclopiperidinyl-1-arylsulfonylindoles Derivatives as Novel, Potent, and Selective 5-$HT_6$ Receptor Antagonists", Bioorganic & Medicinal Chemistry Letters, 10, pp. 1719-1721 (2000).

* cited by examiner

Primary Examiner—Brenda Coleman
(74) Attorney, Agent, or Firm—Fish & Richardson P.C.

(57) ABSTRACT

The present invention relates to substituted sulfonamide compounds of the general formula (I), wherein P is sulfonamide or amide-substituted sulfonic acid, which compounds are potentially useful for the prophylaxis and treatment of medical conditions relating to obesity, type II diabetes and/or disorders of the central nervous system (I)

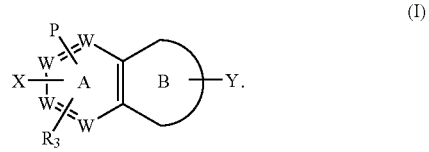

19 Claims, No Drawings

US 7,144,883 B2

BICYCLIC SULFONAMIDE COMPOUNDS

RELATED APPLICATIONS

This application claims priority to Swedish application number 0102048-6, filed on Jun. 11, 2001, Swedish application number 0102386-0, filed on Jul. 3, 2001, and Swedish application number 0103437-0, filed on Oct. 16, 2001, the contents of which are incorporated herein by reference.

TECHNICAL FIELD

The present invention relates to substituted sulfonamide compounds, to pharmaceutical compositions comprising these compounds, and to the use of the compounds for the prophylaxis and treatment of medical conditions relating to obesity, type II diabetes, and CNS disorders.

BACKGROUND ART

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type II diabetes. Searching for compounds, which reduce body weight has been going on for many decades. One line of research has been activation of serotoninergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and depression. Multiple serotonin receptor subtypes have been identified and cloned. One of these, the 5-HT$_6$ receptor, was cloned by several groups in 1993 (Ruat, M. et al. (1993) Biochem. Biophys. Res. Commun. 193: 268–276; Sebben, M. et al. (1994) NeuroReport 5: 2553–2557). This receptor is positively coupled to adenylyl cyclase and displays affinity for antidepressants such as clozapine. Recently, the effect of 5-HT$_6$ antagonist and 5-HT$_6$ antisense oligonucleotides to reduce food intake in rats has been reported (Bentley, J. C. et al. (1999) Br J Pharmac. Suppl. 126, P66; Bentley, J. C. et al. (1997) J. Psychopharmacol. Suppl. A64, 255).

Compounds with enhanced affinity and selectivity for the 5-HT$_6$ receptor have been identified, e.g. in WO 00/34242 and by Isaac, M. et al. (2000) 6-Bicyclopiperazinyl-1-arylsulfonylindoles and 6-Bicyclopiperidinyl-1-arylsulfonylindoles derivatives as novel, potent and selective 5-HT$_6$ receptor antagonists. Bioorganic & Medicinal Chemistry Letters 10: 1719–1721 (2000).

INFORMATION DISCLOSURE

J. Med. Chem. 1970, 13(4), 592–598 describes N-(4-{[2-(diethylamino)ethyl]amino}-1-naphthyl)amides; N-{5,6,7,8-Tetrahydro-4-[(3-piperidinopropyl)amino]-1-naphthyl}amides and related amides and urea derivatives as schistosomicides.

WO 99/42465 discloses sulphonamides derivatives that bind to the 5-HT$_6$ receptor and that can be used for the treatment of CNS disorders such as anxiety, depression, epilexy, obsessive compulsive disorders, cognitive disorders, ADHD, anorexia and bulimia schizophrenia, drug abuse.

WO 01/32646 A1 discloses compounds that binds to the 5-HT$_6$ receptor and that are used for the treatment of CNS disorders and which inter alia may be used for the treatment of eating disorders.

WO 99/37623 A2 discloses compounds that binds to the 5-HT$_6$ receptor and that are used for the treatment of CNS disorders and which inter alia may be used for the treatment of eating disorders.

WO 99/42465 A3 discloses compounds that binds to the 5-HT$_6$ receptor and that are used for the treatment of CNS disorders and which inter alia may be used for the treatment of eating disorders.

EP 0 815 861 A1 discloses compounds that binds to the 5-HT$_6$ receptor and that are used for the treatment of CNS disorders.

WO 99/02502 A2 discloses compounds that binds to the 5-HT$_6$ receptor and that are used for the treatment of CNS disorders and which inter alia may be used for the treatment of eating disorders.

WO 98/27081 A1 discloses compounds that binds to the 5-HT$_6$ receptor and that are used for the treatment of CNS disorders and which inter alia may be used for the treatment of eating disorders.

DISCLOSURE OF THE INVENTION

It has surprisingly been found that the compounds of formula (I) show affinity for the 5-HT$_6$ receptor as antagonists at low nanomolar range. Compounds according to the invention and their pharmaceutically acceptable salts have 5-HT$_6$ receptor antagonist activity and are believed to be of potential use in the treatment or prophylaxis of obesity and type II diabetes, as well as in the treatment or prophylaxis of disorders of the central nervous system such as anxiety, depression, panic attacks, memory disorders, sleep disorders, migraine, anorexia, bulimia, binge disorders, obsessive compulsive disorders, psychoses, Alzheimer's disease, Parkinson's disease, Huntington's chorea and/or schizophrenia, Attention Deficit Hyperactive Disorders (ADHD), drug abuse.

Definitions

Unless otherwise stated or indicated, the term "$C_{1-6}$ alkyl" denotes a straight or branched alkyl group having from 1 to 6 carbon atoms. Examples of said lower alkyl include methyl, ethyl, n-propyl, iso-propyl, n-butyl, iso-butyl, sec-butyl, t-butyl and straight- and branched-chain pentyl and hexyl.

Unless otherwise stated or indicated, the term "$C_{1-6}$ alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "halogen" shall mean fluorine, chlorine, bromine or iodine.

The term "$C_{3-7}$ cycloalkyl" denotes a cyclic alkyl group having a ring size from $C_3$ to $C_7$. Examples of said cycloalkyl include cyclopropyl, cyclobutyl, cyclopentyl, cyclohexyl, methylcyclohexyl and cycloheptyl.

The term "heterocyclic" refers to a hydrocarbon ring system containing 4 to 8 ring members that have at least one heteroatom (e.g., S, N, or O) as part of the ring. It includes saturated, unsaturated, aromatic, and nonaromatic heterocycles. Suitable heterocyclic groups include thienyl, furyl, pyridyl, pyrrolidinyl, imidazolyl, pyrazolyl, piperidyl, azepinyl, morpholinyl, pyranyl, dioxanyl, pyridazinyl, pyrimidinyl, and piperazinyl groups The term "heteroaryl" refers to a hydrocarbon ring system having at least one aromatic ring which contains at least one heteroatom such as O, N, or S. Examples of heteroaryl groups include furyl, pyrrolyl, thienyl, oxazolyl, imidazolyl, thiazolyl, pyridinyl, pyrimidinyl, quinazolinyl, and indolyl groups.

Compounds of Formula I

In a first aspect, the present invention provides a compound having the general formula I:

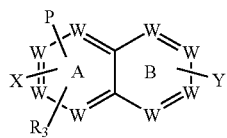

or a pharmaceutically acceptable salt thereof, wherein:
W is N or —(CH)—, provided that not more than three groups W are N;
P is

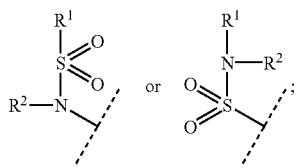

with the proviso that P and $R^3$ can only be in meta or para position to each other;
$R^1$ is
(a) $C_{1-6}$ alkyl,
(b) $C_{1-6}$ alkoxyalkyl,
(c) straight or branched $C_{1-6}$ hydroxyalkyl,
(d) straight or branched $C_{1-6}$ alkylhalides; or
(e) a group Ar;
Ar is
(a) phenyl,
(b) 1-naphthyl,
(c) 2-naphthyl,
(d) benzyl,
(e) cinnamoyl,
(f) a 5 to 7-membered, optionally aromatic, partially saturated or completely saturated, heterocyclic ring containing 1 to 4 heteroatoms, selected from oxygen, nitrogen and sulfur, or
(g) a bicyclic ring system comprising at least one heterocyclic ring according to (f).
wherein the group Ar is substituted in one or more positions with
(a) H, X or Y, or
(b) a 5 to 7-membered, optionally aromatic, partially saturated or completely saturated, mono- or bi-cyclic heterocyclic ring each containing 1 to 4 heteroatoms selected from oxygen, nitrogen or sulfur;

$R^2$ is
(a) H,
(b) $C_{1-6}$ alkyl,
(c) $C_{1-6}$ alkoxyalkyl,
(d) straight or branched $C_{1-6}$ hydroxyalkyl, or
(e) straight or branched $C_{1-6}$ alkylhalides;
$R^3$ is a group

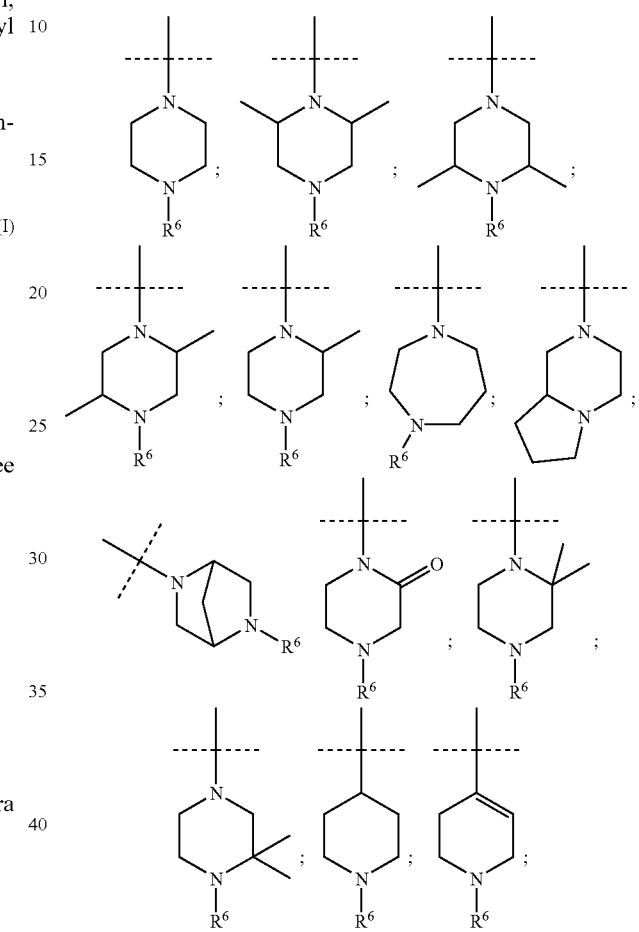

X and Y are independently
(a) H,
(b) halogen,
(c) $C_{1-6}$ alkyl,
(d) $CF_3$,
(e) hydroxy,
(f) $C_{1-6}$ alkoxy,
(g) $C_{1-4}$ alkenyl;
(h) phenyl;
(i) phenoxy,
(j) benzyloxy,
(k) benzoyl,
(l) —$OCF_3$,
(m) —CN,
(n) straight or branched $C_{1-6}$ hydroxyalkyl,
(o) straight or branched $C_{1-6}$ alkylhalides,
(p) —$NH_2$,
(q) —$NHR^4$,
(r) —$NR^4R^5$,
(s) —$NO_2$,
(t) —$CON R^4R^5$,
(u) —$NHSO_2 R^4$, (v) —NR$^6$COR$^5$,
(x) —SO$_2$NR$^4$R$^5$,
(z) —C(=O) R$^4$,
(aa) —CO$_2$R$^4$, or
(ab) —S(O)$_n$ R$^4$; wherein n is 0, 1, 2 or 3,
(ac) —S—(C$_{1-6}$)alkyl
(ad) —SCF$_3$
R$^4$ and R$^5$ are independently
(a) H,
(b) C$_{1-6}$ alkyl,
(c) C$_{3-7}$ cycloalkyl, or
(d) Ar, as defined above for R$^1$;
alternatively, R$^4$ and R$^5$ are linked to form a group (CH$_2$)$_2$O, (CH$_2$)$_4$O or (CH$_2$)$_{3-5}$; and
R$^6$ is
(a) H, or
(b) C$_{1-6}$ alkyl.

In one aspect, this invention features a compound of the formula (I):

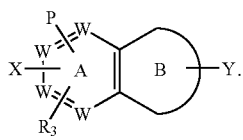

(I)

or a pharmaceutically acceptable salt thereof, wherein:
ring B is

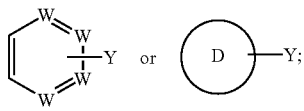

in which D is a five-membered heterocyclic or heteroaryl ring, said ring comprising one or two atoms selected from the group consisting of nitrogen, sulfur and oxygen, with the proviso that when D contains an oxygen atom, D is heteroaryl;
W is N or —(CH)—, provided that not more than three groups W are N in both rings A and B together;
P is

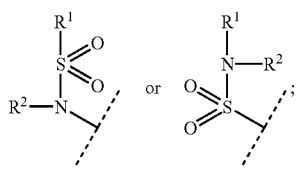

P and R$^3$ are bound to the same ring and are disposed in the meta- or para-positions relative to each other;
R$_1$ is
(a) C$_{1-6}$ alkyl,
(b) C$_{1-6}$ alkoxyalkyl,
(c) straight or branched C$_{1-6}$ hydroxyalkyl,
(d) straight or branched C$_{1-6}$ alkylhalides; or
(e) a group Ar;
Ar is
(a) phenyl,
(b) 1-naphthyl,
(c) 2-naphthyl,
(d) benzyl,
(e) cinnamoyl,
(f) a 5 to 7-membered, optionally aromatic, partially saturated or completely saturated, heterocyclic ring containing 1 to 4 heteroatoms, selected from oxygen, nitrogen and sulfur, or
(g) a bicyclic ring system comprising at least one heterocyclic ring according to (f).
wherein the group Ar is substituted in one or more positions with
(a) H, X or Y, or
(b) a 5 to 7-membered, optionally aromatic, partially saturated or completely saturated, heterocyclic ring each containing 1 to 4 heteroatoms selected from oxygen, nitrogen or sulfur;
R$^2$ is
(a) H,
(b) C$_{1-6}$ alkyl,
(c) C$_{1-6}$ alkoxy,
(d) straight or branched C$_{1-6}$ hydroxyalkyl, or
(e) straight or branched C$_{1-6}$ alkylhalides;
or R$^1$ and R$^2$ are linked to form a group (CH$_2$)$_4$O, which represents (CH$_2$)—(CH$_2$)—O—(CH$_2$)—(CH$_2$);
One of R$^3$ is a group

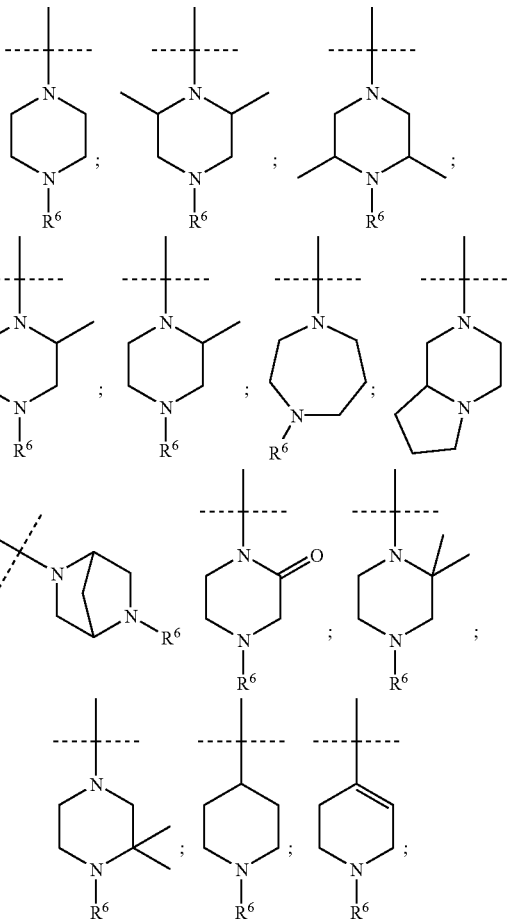

X and Y are independently
(a) H,
(b) halogen,
(c) C$_{1-6}$ alkyl, (d) —$CF_3$,
(e) hydroxy,
(f) $C_{1-6}$ alkoxy,
(g) $C_{1-4}$ alkenyl;
(h) phenyl;
(i) phenoxy,
(j) benzyloxy,
(k) benzoyl,
(l) —$OCF_3$,
(m) —CN,
(n) straight or branched $C_{1-6}$ hydroxyalkyl,
(o) straight or branched $C_{1-6}$ alkylhalides,
(p) —$NH_2$,
(q) —$NHR^4$,
(r) —$NR^4R^5$,
(s) —$NO_2$,
(t) —$CONR^4R^5$,
(u) —$NHSO_2R^4$,
(v) —$NR^4COR^5$,
(x) —$SO_2NR^4R^5$,
(z) —C(=O)$R^4$,
(aa) —$CO_2R^4$, or
(ab) —S(O)$_n$$R^4$; wherein n is 0, 1, 2 or 3;
(ac) —S—($C_{1-6}$)alkyl
(ad) —$SCF_3$
$R^4$ and $R^5$ are independently
(a) H,
(b) $C_{1-6}$ alkyl,
(c) $C_{3-7}$ cycloalkyl, or
(d) Ar, as defined above for $R^1$;
alternatively, $R^4$ and $R^5$ are linked to form a group $(CH_2)_2O$, $(CH_2)_4O$ or $(CH_2)_{3-5}$; in which $(CH_2)_2O$ represents $(CH_2)$—O—$(CH_2)$ and $(CH_2)_4O$ represents $(CH_2)$—$(CH_2)$—O—$(CH_2)$—$(CH_2)$; and
$R^6$ is
(a) H, or
(b) straight of branched $C_{1-6}$ alkyl.

In preferred forms, the invention provides naphthalene compounds of the formula (II), isoquinoline compounds of the formula (III), quinoline compounds of the formula (IV), 1,7-naphthyridine compounds of the formula (V), and benzofuran, benzothiophene, or indole compounds of the formula (VI):

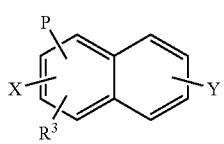
(II)

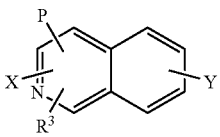
(III)

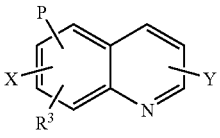
(IV)

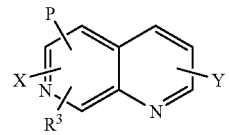
(V)

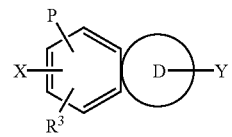
(VI)

wherein $R^3$, P, X and Y are as defined for formula (I); and wherein D in formula (VI) is a five-membered heterocyclic or heteroaryl ring, said ring comprising one or two atoms selected from the group consisting of nitrogen, sulfur and oxygen, with the proviso that when D contains an oxygen atom, D is heteroaryl. The group Y can be attached to any unsubstituted carbon atom in D. When the heteroaryl ring comprises one or two nitrogen atoms, a group $R^6$ could be attached at the secondary nitrogen.

Preferred compounds of the general formulas (I), (II), (III), and (IV), (V), (VI) are those wherein:
$R^1$ is
(a) $C_{1-6}$ alkyl, or
(e) a group Ar;
Ar is
(a) phenyl,
(b) 1-naphthyl,
(c) 2-naphthyl, or
(f) a 5 to 7-membered, partially or completely saturated, mono- or bi-cyclic heterocyclic ring each containing 1 to 4 heteroatoms selected from oxygen, nitrogen or sulfur;

wherein the group Ar is substituted in one or more positions with X or Y; wherein X or Y is
(a) H,
(b) halogen,
(c) $C_{1-6}$ alkyl,
(d) —$CF_3$,
(f) $C_{1-6}$ alkoxy,
(g) $C_{1-4}$ alkenyl;
(l) —$OCF_3$, or
(m) straight or branched $C_{1-6}$ hydroxyalkyl
(n) phenyloxy
(o) benzyloxy
(ab) —S(O)$_n$$R^4$; wherein n is 0, 1, 2 or 3,
(ac) —S—($C_{1-6}$)alkyl
(ad) —$SCF_3$
(v) —$NR^4COR^5$,
(x) —$SO_2NR^4R^5$,
(z) —C(=O)$R^4$.
$R^2$ is
(a) H, or
(b) $C_{1-3}$ alkyl, in particular methyl;
or $R^1$ and $R^2$ are linked to form a group $(CH_2)_4O$;

R³ is

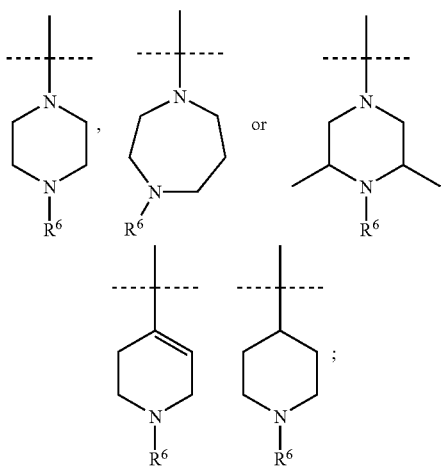

wherein R⁶ is
(a) H, or
(b) $C_{1-6}$ alkyl, in particular methyl;
X and Y are H; and/or
D is furanyl.

Preferred compounds of the formula II are para-substituted naphthalene compounds wherein P is

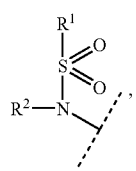

wherein $R^1$ and $R^2$ are as defined for formula (I); and X and Y are H, halogens, methyl, methoxy, (cf. Table I). Particularly preferred of such compounds are those wherein $R^1$ is phenyl, methylphenyl, methoxyphenyl, dimethoxyphenyl, 1-naphthyl, 2-naphthyl, fluoromethylphenyl, chlorophenyl, dichlorophenyl, fluorochlorophenyl, dichlorothienyl, chlorothienyl, trifluoromethylphenyl, or methoxymethylphenyl; $R^2$ is H or methyl; and $R^3$ is piperazinyl or homopiperazinyl, 3,5-dimethylpiperazine, 4-piperidine, 4-(4,3)-dihydropyridine, 4-(1,2,3,6)-tetrahydropyridine; $R^6$ is H, methyl, ethyl, isopropyl. Further preferred compounds of the formula II are compounds with a group P and a group $R^3$ in para-position.

Further preferred compounds of the formula II are compounds with a group P and a group $R^3$ in para-position, wherein P is

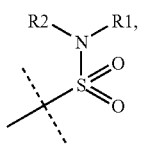

wherein $R^1$ and $R^2$ are as defined for formula (I) (cf. Table III); and X or Y are H, methyl, ethyl, isopropyl, methoxy, thiomethyl, 1-naphthyl, phenyloxy, trifluoromethoxy, trifluorothienyl (cf. Table II). Particularly preferred of such compounds are those wherein $R^1$ is phenyl, 1-naphthyl, phenyloxyphenyl, dimethoxyphenyl, dimethylphenyl, methylchlorophenyl, isopropylphenyl, fluorophenyl, 1(2H)-3,4-dihydroquinolin, $R^2$ is H or methyl, $R^3$ is piperazinyl, and $R^6$ is H.

Preferred compounds of the formula III are isoquinoline compounds wherein P is

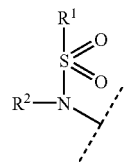

and occupies position 3 of the ring, wherein $R^1$ and $R^2$ are as defined for formula (I); and X or Y are H, methyl, bromo, methoxy, acetylamino (cf. Table IV). Particularly preferred of such compounds are those wherein $R^1$ is phenyl, bromophenyl, methylchlorophenyl, methylphenyl, methoxyphenyl, trimethylphenyl, dimethoxyphenyl, bromomethoxyphenyl; $R^2$ is H or methyl; and $R^3$ is methylpiperazinyl.

Preferred compounds of the formula IV are quinoline compounds wherein P is

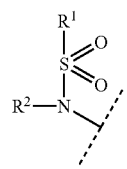

and occupies position 5 of the ring, wherein $R^1$ and $R^2$ are as defined for formula (I); and X, Y is H (cf. Table V). Particularly preferred of such compounds are those wherein $R^1$ is phenyl; $R^2$ is H or methyl; and $R^3$ is piperidinyl.

Preferred compounds of the formula V are 1,7-naphthyridine compounds wherein P is

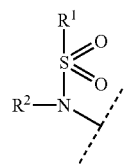

and occupies position 8 of the ring, wherein $R^1$ and $R^2$ are as defined for formula (I); and X and Y are halogen, methoxy (cf. Table V). Particularly preferred of such compounds are those wherein $R^1$ is phenyl, dimethoxyphenyl, 1-naphthyl; $R^2$ is H or methyl; and $R^3$ is piperidinyl;

Preferred compounds of the formula VI are benzofuran compounds wherein P is

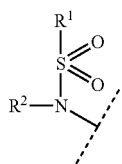

and occupies position 5 of the ring, wherein $R^1$ and $R^2$ are as defined for formula (I) and wherein D in formula (VI) is a five-membered heterocyclic or heteroaryl ring, said ring comprising one or two atoms selected from the group consisting of nitrogen, sulfur and oxygen, with the proviso that when D contains an oxygen atom, D is heteroaryl. The group Y can be attached to any unsubstituted carbon atom in D. When the heteroaryl ring comprises one or two nitrogen atoms, a group $R^6$ could be attached at the secondary nitrogen; and X and Y are halogen, methoxy (cf. Table V). Particularly preferred of such compounds are those wherein $R^1$ is phenyl, dichlorophenyl, bromophenyl, dichloromethylphenyl, 1-naphthyl, phenyl, methylphenyl, fluorophenyl, thiophenyl, chlorothiophenyl; $R^2$ is H or methyl; and $R^3$ is piperidinyl or N-methylpiperidinyl.

TABLE I

Para-substituted naphthalene compounds of the formula II wherein P is [structure]; and X, Y are H:

| Compound name | $R^1$ | $R^3$ | $R^2$ |
|---|---|---|---|
| 1 N-(4-Methylphenyl)-4-(1-piperazinyl)-1-naphthalenesulfonamide, hydrochloride | 4-methylphenyl | piperazinyl | H |
| 2 N-(2,4-Dimethoxyphenyl)-4-(1-piperazinyl)-1-naphthalenesulfonamide, hydrochloride | 2,4-dimethoxyphenyl | piperazinyl | H |
| 3 N-(3,4-di-Fluorophenyl)-4-(4-methyl-1,4-diazepan-1-yl)-1-naphthalenesulfonamide, hydrochloride | 3,4-difluorophenyl | 4-methyl-1,4-diazepan-1-yl | H |
| 4 N-(3-Fluorophenyl)-4-(4-methyl-1,4-diazepan-1-yl)-1-naphthalenesulfonamide, hydrochloride | 3-fluorophenyl | 4-methyl-1,4-diazepan-1-yl | H |

TABLE I-continued

| | | | | |
|---|---|---|---|---|
| 5 | 4-(4-Ethyl-1-piperazinyl)-N-phenyl-1-naphthalenesulfonamide, hydrochloride | 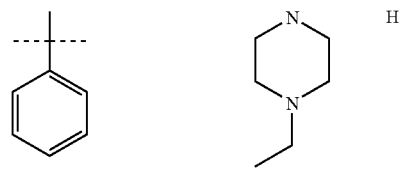 | | H |
| 6 | 4-Hexahydropyrrolo[1,2-a]pyrazin-2(1H)-yl-N-(4-methylphenyl)-1-naphthalenesulfonamide, hydrochloride | 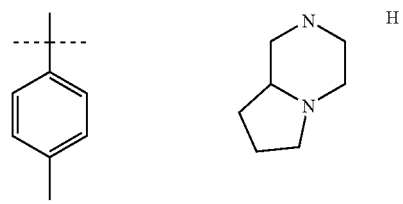 | | H |
| 7 | N-(3,4-Dimethoxyphenyl)-4-hexahydropyrrolo[1,2-a]pyrazin-2(1H)-yl-1-naphthalenesulfonamide, hydrochloride | 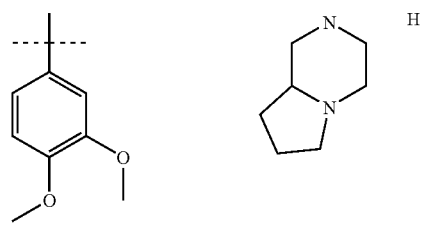 | | H |
| 8 | 4-(4-Ethyl-1-piperazinyl)-N-(4-methylphenyl)-1-naphthalenesulfonamide, hydrochloride | 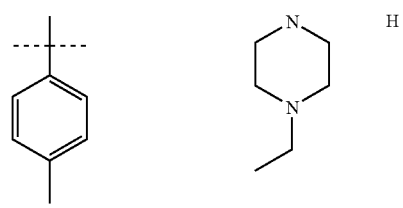 | | H |
| 9 | N-(3,4-Dimethoxyphenyl)-4-(3-methyl-1-piperazinyl)-1-naphthalenesulfonamide, hydrochloride | 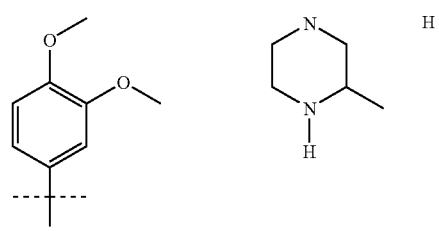 | | H |
| 10 | N-(4-Methylphenyl)-4-(4-methyl-1-piperazinyl)-1-naphthalenesulfonamide, hydrochloride | 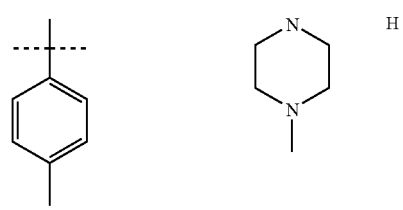 | | H |
| 11 | N-[4-(2,5-Diazabicyclo[2.2.1]hept-2-yl)-1-naphthyl]-4-methylbenzenesulfonamide, hydrochloride | 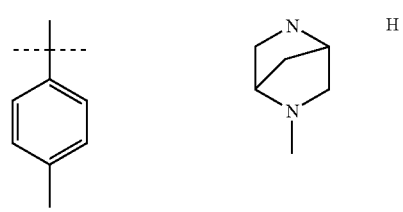 | | H |

TABLE I-continued

| | | | | |
|---|---|---|---|---|
| 12 | N-(4-Methylphenyl)-4-(3-methyl-1-piperazinyl)-1-naphthalenesulfonamide, hydrochloride | 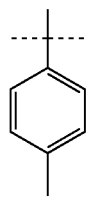 | 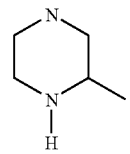 | H |
| 13 | N-(2-Naphthyl)-4-(1-piperazinyl)-1-naphthalenesulfonamide, hydrochloride | 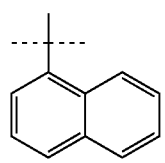 | 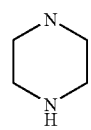 | H |
| 14 | N-Methyl-N-(4-methylphenyl)-4-(1-piperazinyl)-1-naphthalenesulfonamide, hydrochloride | 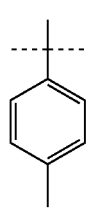 | 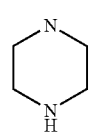 | —CH₃ |
| 15 | 4-(1,4-Diazepan-1-yl)-N-(4-methylphenyl)-1-naphthalenesulfonamide, hydrochloride | 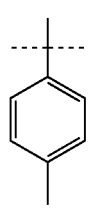 | 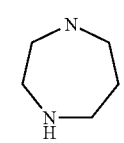 | H |
| 16 | 4-(1,4-Diazepan-1-yl)-N-(2-methoxy-4-methylphenyl)-1-naphthalenesulfonamide, hydrochloride | 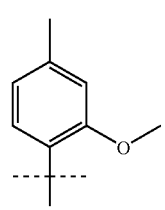 | 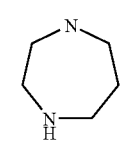 | H |
| 17 | N-(2-Methoxy-4-methylphenyl)-4-(3,5-trimethyl-1-piperazinyl)-1-naphthalenesulfonamide, hydrochloride | 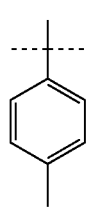 | 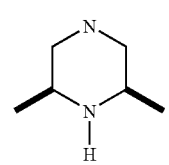 | H |
| 18 | 4-(4-Isopropyl-1-piperazinyl)-N-(4-methylphenyl)-1-naphthalenesulfonamide, hydrochloride | 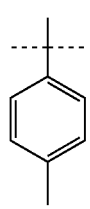 | 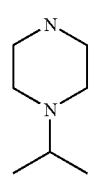 | H |
| 19 | 4-Bromo-N-(4-piperazin-1-yl-naphthalen-1-yl)-benzenesulfonamide, hydrochloride | 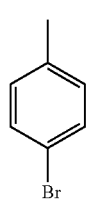 | 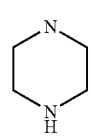 | H |

TABLE I-continued

| | | | | |
|---|---|---|---|---|
| 20 | 2,5-di-Chloro-N-[4-(1-piperazinyl)-1-naphthyl]benzenesulfonamide, hydrochloride | 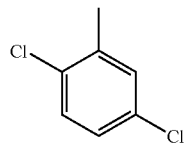 | 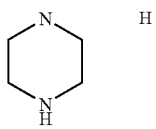 | H |
| 21 | 2-Chloro-4-fluoro-N-[4-(1-piperazinyl)-1-naphthyl]benzenesulfonamide, hydrochloride | 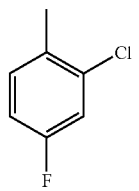 | 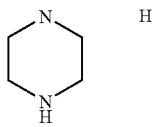 | H |
| 22 | 2,3-di-Chloro-N-[4-(1-piperazinyl)-1-naphthyl]benzenesulfonamide, hydrochloride | 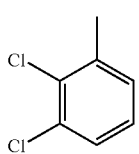 | 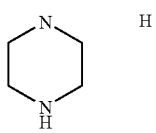 | H |
| 23 | 2,4-di-Chloro-5-methyl-N-[4-(1-piperazinyl)-1-naphthyl]benzenesulfonamide, hydrochloride | 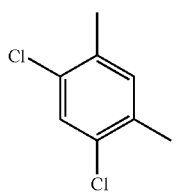 | 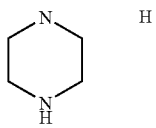 | H |
| 24 | 3-tri-Fluoromethyl-N-[4-(1-piperazinyl)-1-naphthyl]benzenesulfonamide, hydrochloride | 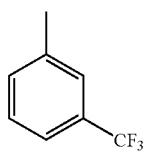 | 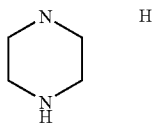 | H |
| 25 | 2-tri-Fluoromethyl-N-[4-(1-piperazinyl)-1-naphthyl]benzenesulfonamide, hydrochloride | 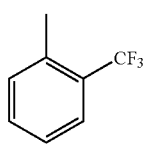 | 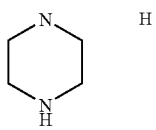 | H |
| 26 | 4-Bromo-N-methyl-N-(4-piperazin-1-yl-naphthalen-1-yl)-benzenesulfonamide, hydrochloride. | 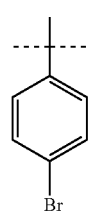 | 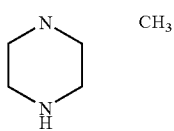 | CH$_3$ |
| 27 | Naphthalene-1-sulfonic acid (4-piperazin-1-yl-naphthalen-1-yl)-amide, hydrochloride | 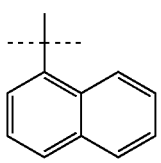 | 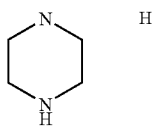 | H |
| 28 | 2,5-Dichloro-thiophene-3-sulfonic acid (4-piperazin-1-yl-naphthalen-1-yl)-amide, hydrochloride | 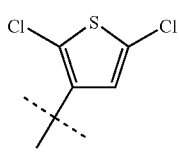 | 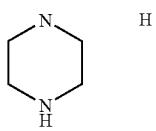 | H |

TABLE I-continued

| | | | | |
|---|---|---|---|---|
| 29 | 4-Methoxy-N-(4-piperazin-1-yl-naphthalen-1-yl)-benzenesulfonamide, hydrochloride | 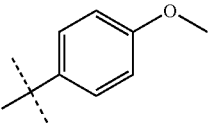 | 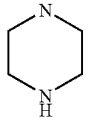 | H |
| 30 | 4-Chloro-N-(4-piperazin-1-yl-naphthalen-1-yl)-benzenesulfonamide, hydrochloride | 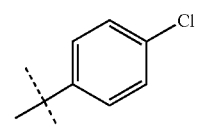 | 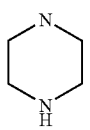 | H |
| 31 | 2-Chloro-N-(4-piperazin-1-yl-naphthalen-1-yl)-benzenesulfonamide, hydrochloride | 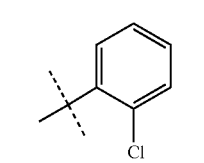 | 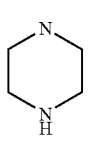 | H |
| 32 | N-(4-Piperazin-1-yl-naphthalen-1-yl)-4-trifluoromethyl-benzenesulfonamide, hydrochloride | 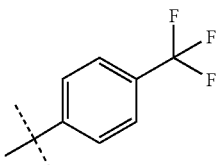 | 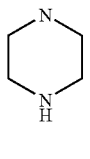 | H |
| 33 | 4-Fluoro-N-(4-piperazin-1-yl-naphthalen-1-yl)-benzenesulfonamide, hydrochloride | 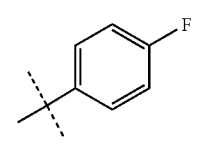 | 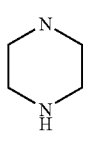 | H |
| 34 | 5-Fluoro-2-methyl-N-(4-piperazin-1-yl-naphthalen-1-yl)-benzenesulfonamide, hydrochloride | 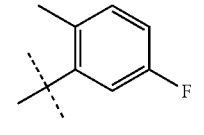 | 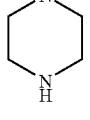 | H |
| 35 | 4-Phenoxy-N-(4-piperazin-1-yl-naphthalen-1-yl)-benzenesulfonamide, hydrochloride | 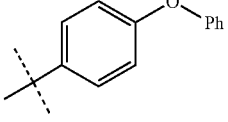 | 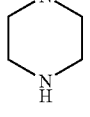 | H |
| 36 | 2-Bromo-4-iodo-N-(4-piperazin-1-yl-naphthalen-1-yl)-benzenesulfonamide, hydrochloride | 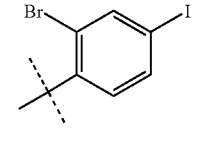 | 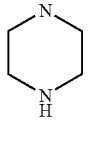 | H |
| 37 | Thiophene-2-sulfonic acid (4-piperazin-1-yl-naphthalen-1-yl)-amide, hydrochloride | 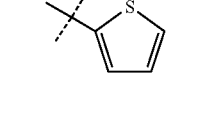 | 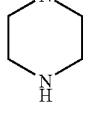 | H |
| 38 | 5-Chloro-thiophene-2-sulfonic acid (4-piperazin-1-yl-naphthalen-1-yl)-amide, hydrochloride | 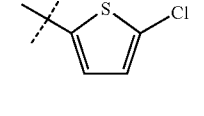 | 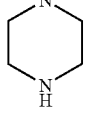 | H |
| 39 | 3-Methyl-N-(4-piperazin-1-yl-naphthalen-1-yl)-benzenesulfonamide, hydrochloride | 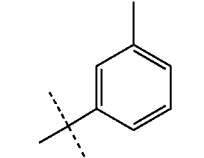 | 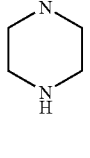 | H |

TABLE I-continued

| | | | | |
|---|---|---|---|---|
| 40 | 4-Butyl-N-(4-piperazin-1-yl-naphthalen-1-yl)-benzenesulfonamide hydrochloride | 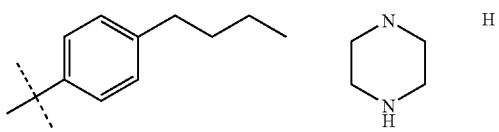 | 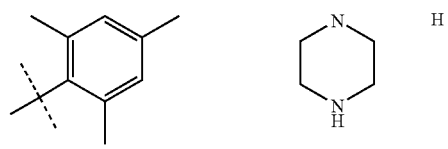 | H |
| 41 | 2,4,6-Trimethyl-N-(4-piperazin-1-yl-naphthalen-1-yl)-benzenesulfonamide hydrochloride | 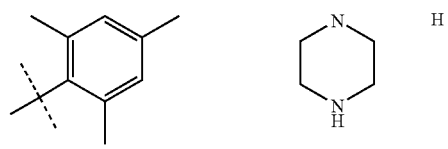 | | H |
| 42 | 2,4,5-Trichloro-N-(4-piperazin-1-yl-naphthalen-1-yl)-benzenesulfonamide, hydrochloride | 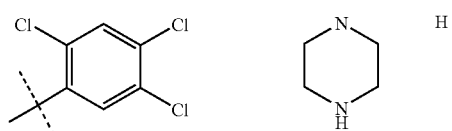 | | H |
| 43 | 4-Iodo-N-(4-piperazin-1-yl-naphthalen-1-yl)-benzenesulfonamide, hydrochloride | 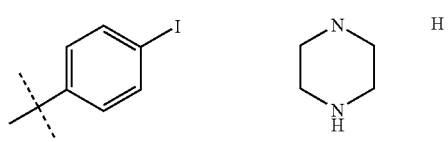 | | H |
| 44 | 2-Methyl-N-(4-piperazin-1-yl-naphthalen-1-yl)-benzenesulfonamide, hydrochloride |  | | H |
| 45 | 3,4-Dichloro-N-(4-piperazin-1-yl-naphthalen-1-yl)-benzenesulfonamide, hydrochloride | 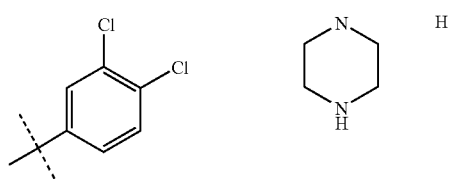 | | H |
| 46 | 5-Bromo-2-methoxy-N-(4-piperazin-1-yl-naphthalen-1-yl)-benzenesulfonamide, hydrochloride | 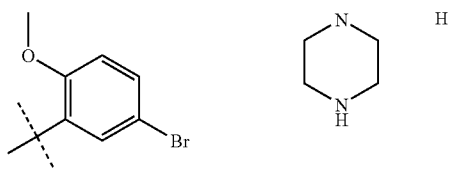 | | H |
| 47 | 2-Bromo-N-(4-piperazin-1-yl-naphthalen-1-yl)-benzenesulfonamide, hydrochloride |  | | H |
| 48 | 3-Chloro-2-methyl-N-(4-piperazin-1-yl-naphthalen-1-yl)-benzenesulfonamide, hydrochloride | 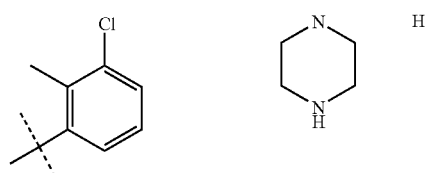 | | H |
| 49 | 2,6-Dichloro-N-(4-piperazin-1-yl-naphthalen-1-yl)-benzenesulfonamide, hydrochloride | 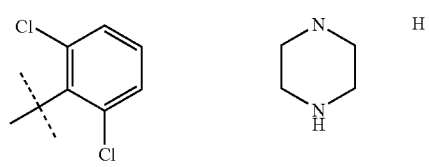 | | H |

TABLE I-continued

| | | | | |
|---|---|---|---|---|
| 50 | 3-Methoxy-N-(4-piperazin-1-yl-naphthalen-1-yl)-benzenesulfonamide, hydrochloride | 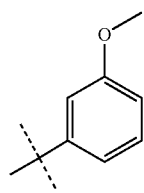 | 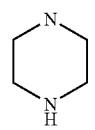 | H |
| 51 | 3-Chloro-4-methyl-N-(4-piperazin-1-yl-naphthalen-1-yl)-benzenesulfonamide, hydrochloride | 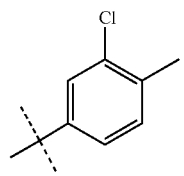 | 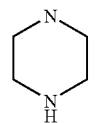 | H |
| 52 | 4-Bromo-2-fluoro-N-(4-piperazin-1-yl-naphthalen-1-yl)-benzenesulfonamide, hydrochloride | 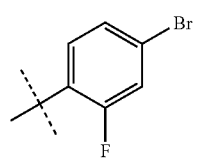 | 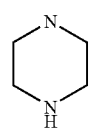 | H |
| 53 | 2,4-Dichloro-6-methyl-N-(4-piperazin-1-yl-naphthalen-1-yl)-benzenesulfonamide, hydrochloride | 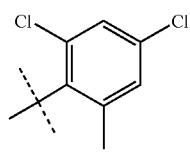 | 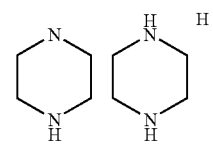 | H |
| 54 | 4-Bromo-2-methyl-N-(4-piperazin-1-yl-naphthalen-1-yl)-benzenesulfonamide, hydrochloride | 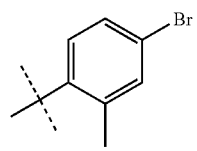 | 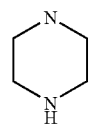 | H |
| 55 | 4,5-Dichloro-thiophene-2-sulfonic acid (4-piperazin-1-yl-naphthalen-1-yl)-amide, hydrochloride | 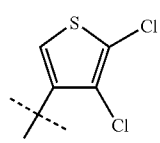 | 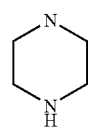 | H |
| 56 | N-Methyl-N-(4-bromo-2-methylphenyl)-4-(1-pyperazinyl)-1-napthalenesulphonamide, hydrochloride | 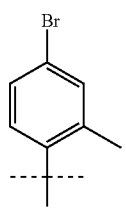 | 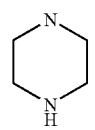 | $CH_3$ |
| 57 | N-Methyl-N-(5-fluoro-2-methylphenyl)-4-(1-pyperazinyl)-1-napthalenesulphonamide, hydrochloride | 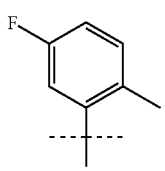 | 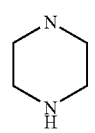 | $CH_3$ |

TABLE I-continued

| | | | | |
|---|---|---|---|---|
| 58 | N-Methyl-N-(2-methylphenyl)-4-(1-pyperazinyl)-1-napthalenesulphonamide, hydrochloride | 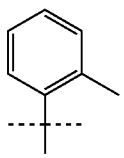 | piperazine-NH | CH₃ |
| 59 | N-Methyl-N-(3-chloro-2-methylphenyl)-4-(1-pyperazinyl)-1-napthalenesulphonamide, hydrochloride | 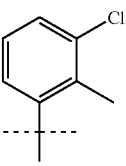 | piperazine-NH | CH₃ |
| 60 | 2,5-di-Chlorothiophen-3-yl-N-Methyl-N-(2,5-dichlorothiophen-3-yl)-4-(1-pyperazinyl)-1-napthalenesulphonamide, hydrochloride | 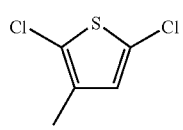 | piperazine-NH | CH₃ |
| 61 | N-Methyl-N-(1-naphthyl)-4-(1-pyperazinyl)-1-napthalenesulphonamide, hydrochloride | 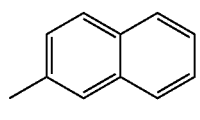 | piperazine-NH | CH₃ |
| 62 | N-Methyl-N-(1-naphthyl)-4-(1-pyperazinyl)-1-napthalenesulphonamide, hydrochloride | 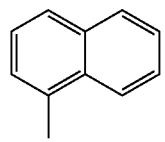 | piperazine-NH | CH₃ |
| 63 | N-Methyl-N-(4-chlorophenyl)-4-(1-pyperazinyl)-1-napthalenesulphonamide, hydrochloride | 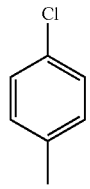 | piperazine-NH | CH₃ |
| 64 | N-Methyl-N-(4-methoxyphenyl)-4-(1-pyperazinyl)-1-napthalenesulphonamide, hydrochloride | 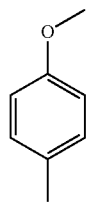 | piperazine-NH | CH₃ |
| 65 | 5-Fluoro-2-methyl-N-{4-[(2R,5S)-2,5-dimethyl-1-]piperazin-1-yl-1-naphthyl}benzenesulfonamide, hydrochloride | 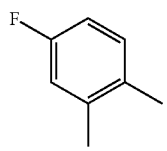 | (2R,5S)-2,5-dimethylpiperazine-NH | H |
| 66 | 5-Fluoro-2-methyl-N-[4-(1,2,3,6-tetrahydropyridin-4-yl)-1-naphthyl]benzenesulfonamide, hydrochloride | 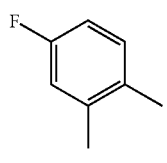 | 1,2,3,6-tetrahydropyridin-4-yl | H |

TABLE II

3-Substituted naphthalene compounds of the formula II wherein P is 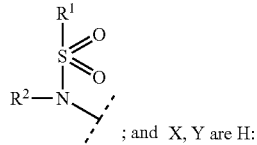 ; and X, Y are H:

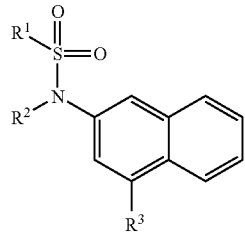

| Compound name | R¹ | R³ | R² |
|---|---|---|---|
| 67 N-[4-(4-Methyl-1-piperazinyl)-2-naphthyl]benzenesulfonamide, hydrochloride | 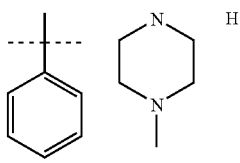 | 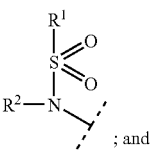 | H |

TABLE III

5-Substituted naphthalene compounds of the formula II wherein P is 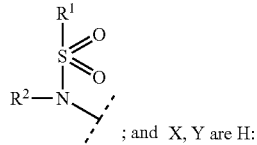 ; and X, Y and R⁴ are H:

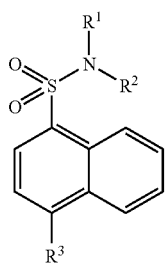

| Compound name | R¹ | R³ | R² |
|---|---|---|---|
| 68 4-Piperazin-1-yl-naphthalene-1-sulfonic acid phenylamide, hydrochloride | 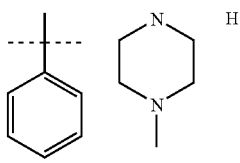 | 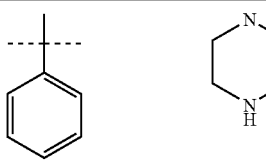 | H |
| 69 4-Piperazin-1-yl-naphthalene-1-sulfonic acid (2-methoxy-phenyl)-amide, hydrochloride | 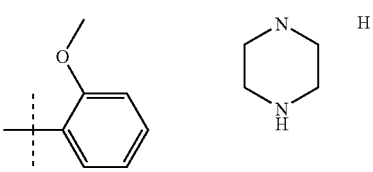 | 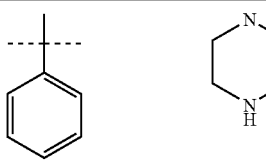 | H |

TABLE III-continued

| | | | | |
|---|---|---|---|---|
| 70 | 4-(cis-3,5-Dimethyl-piperazin-1-yl)-naphthalene-1-sulfonic acid (2-methoxy-phenyl)-amide, hydrochloride | 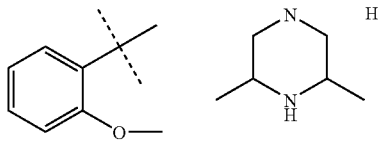 | | H |
| 71 | 4-(cis-3,5-Dimethyl-piperazin-1-yl)-naphthalene-1-sulfonic acid (3-chloro-phenyl)-amide, hydrochloride | 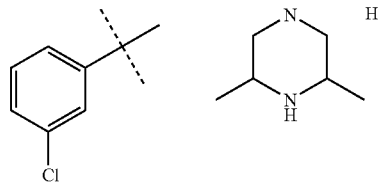 | | H |
| 72 | 4-[1,4]Diazepan-1-yl-naphthalene-1-sulfonic acid (3-chloro-phenyl)-amide, hydrochloride | 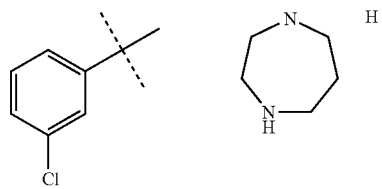 | | H |
| 73 | 4-[1,4]Diazepan-1-yl-naphthalene-1-sulfonic acid phenylamide, hydrochloride | 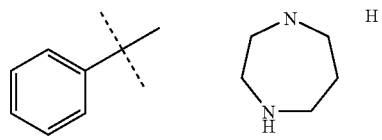 | | H |
| 74 | 4-Piperazin-1-yl-naphthalene-1-sulfonic acid (3-chloro-phenyl)-amide, hydrochloride | 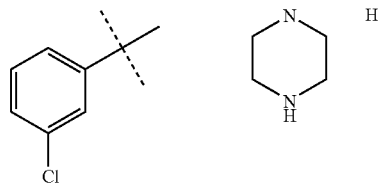 | | H |
| 75 | 4-Piperazin-1-yl-naphthalene-1-sulfonic acid (2-methylsulfanyl-phenyl)-amide, hydrochloride | 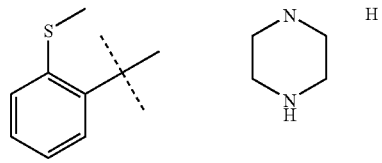 | | H |
| 76 | 4-Piperazin-1-yl-naphthalene-1-sulfonic acid methyl-naphthalen-1-yl-amide, hydrochloride | 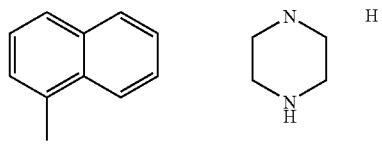 | | H |
| 77 | 4-Piperazin-1-yl-naphthalene-1-sulfonic acid (2,3-dihydro-benzo[1,4]dioxin-6-yl)-methyl-amide, hydrochloride | 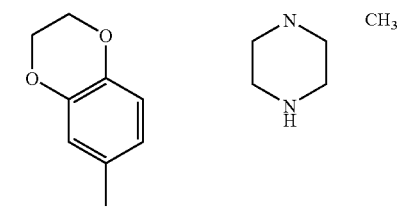 | | CH$_3$ |
| 78 | 4-Piperazin-1-yl-naphthalene-1-sulfonic acid (2,3-dihydro-benzo[1,4]dioxin-6-yl)-amide, hydrochloride | 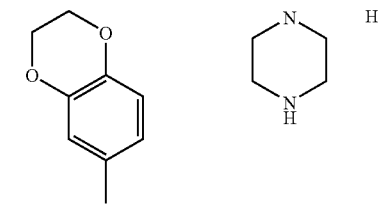 | | H |

TABLE III-continued

| | | | | |
|---|---|---|---|---|
| 79 | 4-Piperazin-1-yl-naphthalene-1-sulfonic acid methyl-(2-methylsulfanyl-phenyl)-amide, hydrochloride | 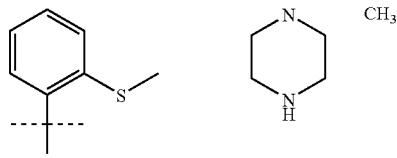 | | CH₃ |
| 80 | 4-Piperazin-1-yl-naphthalene-1-sulfonic acid methyl-(3-trifluoromethyl-phenyl)-amide, hydrochloride | 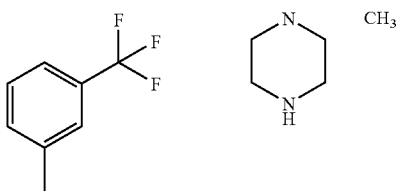 | | CH₃ |
| 81 | 4-Piperazin-1-yl-naphthalene-1-sulfonic acid (3-chloro-4-methyl-phenyl)-methyl-amide, hydrochloride | 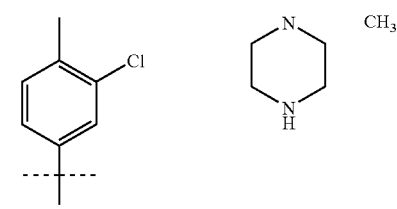 | | CH₃ |
| 82 | 4-Piperazin-1-yl-naphthalene-1-sulfonic acid (3-ethyl-phenyl)-methyl-amide, hydrochloride | 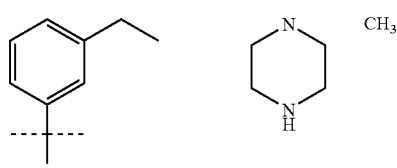 | | CH₃ |
| 83 | 4-(3,5-Dimethyl-piperazin-1-yl)-naphthalene-1-sulfonic acid (2-isopropyl-phenyl)-amide, hydrochloride | 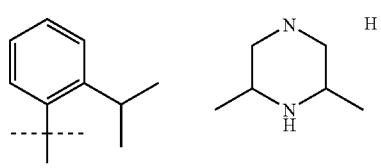 | | H |
| 84 | 4-[1,4]Diazepan-1-yl-naphthalene-1-sulfonic acid (2-isopropyl-phenyl)-amide, hydrochloride | 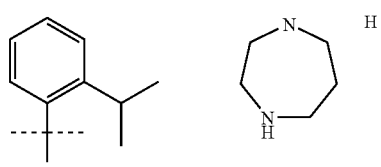 | | H |
| 85 | 4-[1,4]Diazepan-1-yl-naphthalene-1-sulfonic acid (3-ethyl-phenyl)-amide, hydrochloride | 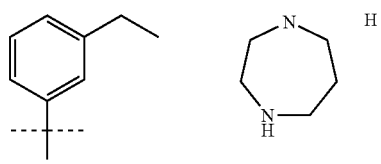 | | H |
| 86 | N-(2-Fluorophenyl)-4-Piperazin-1-ylnaphthalene-1-sulfonamide, hydrochloride | 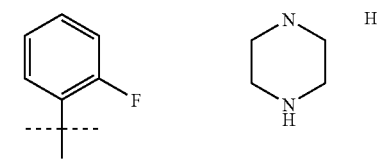 | | H |
| 87 | 4-[1,4]Diazepan-1-yl-naphthalene-1-sulfonic acid (3-trifluoromethyl-phenyl)-amide, hydrochloride | 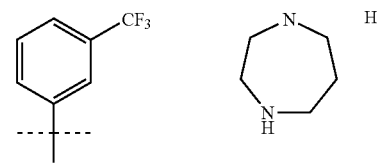 | | H |

TABLE III-continued

| | | | | |
|---|---|---|---|---|
| 88 | N-(2,4-di-Fluorophenyl)-4-piperazin-1-ylnaphthalene-1-sulfonamide, hydrochloride | 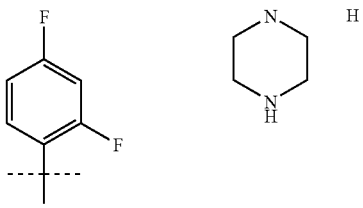 | piperazine | H |
| 89 | 4-Piperazin-1-yl-naphthalene-1-sulfonic acid (2-trifluoromethoxy-phenyl)-amide, hydrochloride | 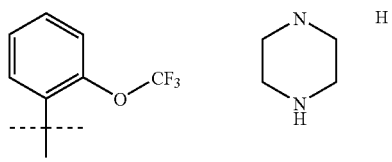 | piperazine | H |
| 90 | 4-Piperazin-1-yl-naphthalene-1-sulfonic acid (3-trifluoromethoxy-phenyl)-amide, hydrochloride | 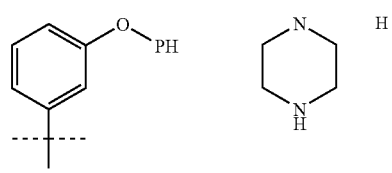 | piperazine | H |
| 91 | 4-Piperazin-1-yl-naphthalene-1-sulfonic acid (3-trifluoromethoxy-phenyl)-amide, hydrochloride | 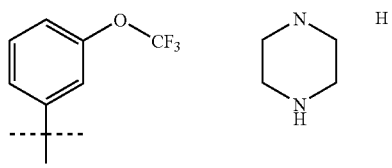 | piperazine | H |
| 92 | 4-Piperazin-1-yl-naphthalene-1-sulfonic acid (2-chloro-5-methyl-phenyl)-amide, hydrochloride | 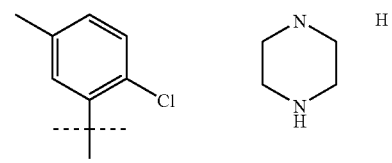 | piperazine | H |
| 93 | 4-Piperazin-1-yl-naphthalene-1-sulfonic acid (4-isopropyl-phenyl)-amide, hydrochloride | 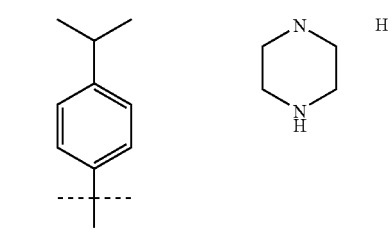 | piperazine | H |
| 94 | N-(3,5-di-Fluorophenyl)-4-piperazin-1-ylnaphthalene-1-sulfonamide, hydrochloride | 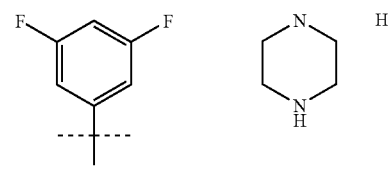 | piperazine | H |
| 95 | 1-[4-(3,4-Dihydroquinolin-1(2H)-ylsulfonyl)-1-naphthyl]piperazine, hydrochloride | 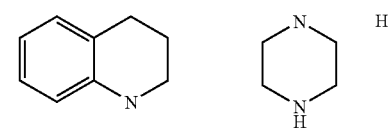 | piperazine | H |
| 96 | 4-[1,4]Diazepan-1-yl-naphthalene-1-sulfonic acid (3-nitro-phenyl)-amide, hydrochloride | 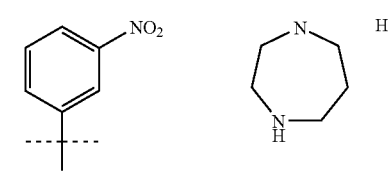 | diazepane | H |

TABLE III-continued

| | | | | |
|---|---|---|---|---|
| 97 | 4-Piperazin-1-yl-naphthalene-1-sulfonic acid (3-nitro-phenyl)-amide, hydrochloride | 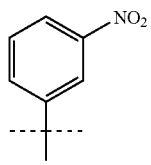 | 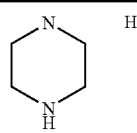 | H |
| 98 | 4-[1,4]Diazepan-1-yl-naphthalene-1-sulfonic acid (3-nitro-phenyl)-methyl-amide, hydrochloride | 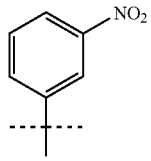 | 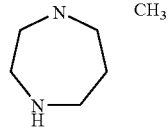 | $CH_3$ |
| 99 | N-(4-methylphenyl)-4-piperazin-1-ylnaphthalene-1-sulfonamide, hydrochloride | 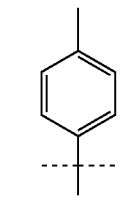 | 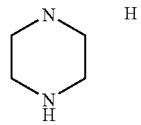 | H |
| 100 | N-(3-chloro-4-methylphenyl)-4-piperazin-1-ylnaphthalene-1-sulfonamide, hydrochloride | 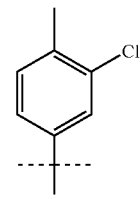 | 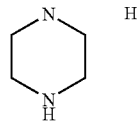 | H |
| 101 | 4-[1,4]Diazepan-1-yl-naphthalene-1-sulfonic acid (2,3-dimethyl-phenyl)-methyl-amide, hydrochloride | 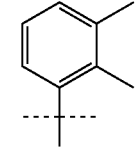 | 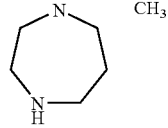 | $CH_3$ |
| 102 | 4-[1,4]Diazepan-1-yl-naphthalene-1-sulfonic acid (4-isopropyl-phenyl)-amide, hydrochloride | 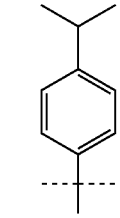 | 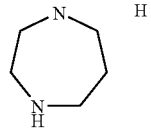 | H |
| 103 | 4-[1,4]Diazepan-1-yl-naphthalene-1-sulfonic acid (4-isopropyl-phenyl)-methyl-amide, hydrochloride | 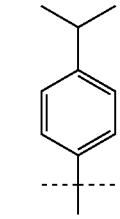 | 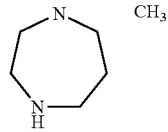 | $CH_3$ |
| 104 | 4-[1,4]Diazepan-1-yl-naphthalene-1-sulfonic acid (2,4-dimethyl-phenyl)-amide, hydrochloride | 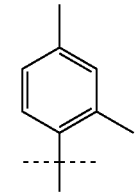 | 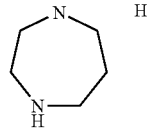 | H |

TABLE III-continued

| | | | | |
|---|---|---|---|---|
| 105 | 4-[1,4]Diazepan-1-yl-naphthalene-1-sulfonic acid (2-chloro-5-methyl-phenyl)-amide, hydrochloride | 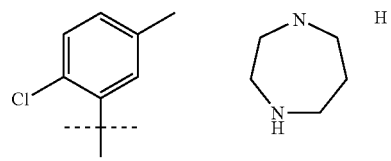 | | H |
| 106 | 4-Piperazin-1-yl-naphthalene-1-sulfonic acid (2,5-dimethoxy-phenyl)-amide, hydrochloride | 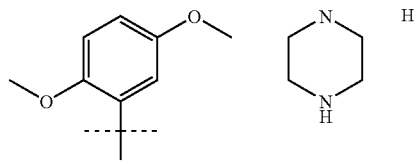 | | H |
| 107 | 4-Piperazin-1-yl-naphthalene-1-sulfonic acid (3-acetyl-phenyl)-amide, hydrochloride | 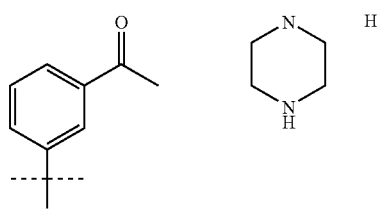 | | H |
| 108 | 4-Piperazin-1-yl-naphthalene-1-sulfonic acid (2,4-dimethyl-phenyl)-amide, hydrochloride | 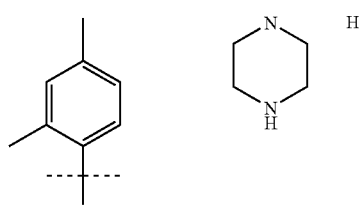 | | H |
| 109 | 4-Piperazin-1-yl-naphthalene-1-sulfonic acid (3-trifluoromethyl-phenyl)-amide, hydrochloride | 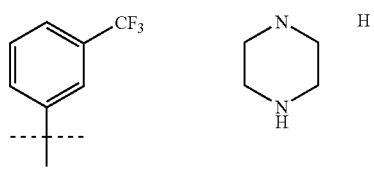 | | H |
| 110 | 4-Piperazin-1-yl-naphthalene-1-sulfonic acid biphenyl-2-ylamide, hydrochloride | 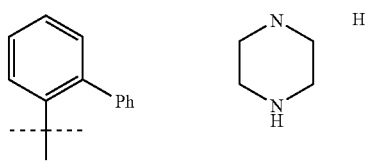 | | H |
| 111 | 4-Piperazin-1-yl-naphthalene-1-sulfonic acid (3-benzyloxy-phenyl)-amide, hydrochloride | 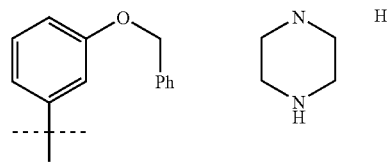 | | H |
| 112 | N-(4-fluorophenyl)-4-piperazin-1-ylnaphthalene-1-sulfonamide, hydrochloride | 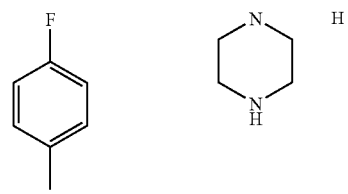 | | H |
| 113 | N-(3-Ethylphenyl)-4-piperazin.1.ylnaphthalene-1-sulphonamine, hydrochloride | 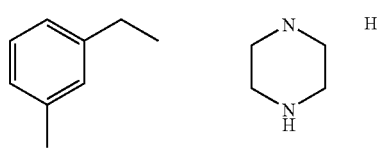 | | H |

TABLE III-continued

| # | Compound name | Structure | | |
|---|---|---|---|---|
| 114 | 4-Piperazinyl-N-[3-(trifluoromethyl)phenyl]naphthalene-1-sulfonamide, hydrochloride | 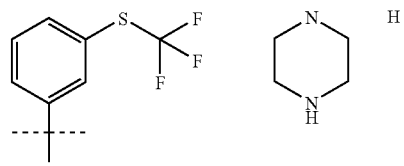 | | H |
| 115 | 4-Piperazinyl-N-[3-benzoylphenyl]naphthalene-1-sulfonamide, hydrochloride | 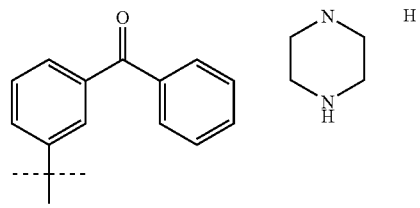 | | H |
| 116 | 4-Piperazinyl-N-[3-(4-bromo-1-methyl-1H-pyrazol-3-yl)phenyl]naphthalene-1-sulfonamide, hydrochloride | 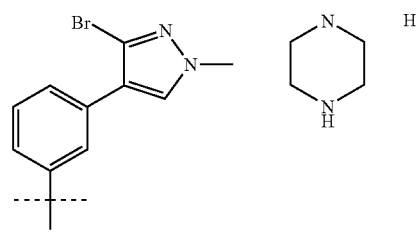 | | H |
| 117 | 4-Piperazinyl-N-[3-biphenylphenyl]naphthalene-1-sulfonamide, hydrochloride | 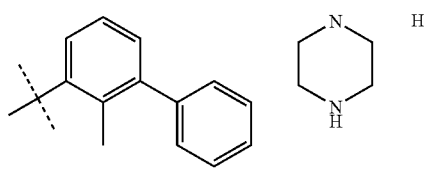 | | H |

TABLE IV

Meta-substituted isoquinoline compounds of the formula III wherein P is 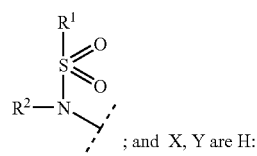 ; and X, Y are H:

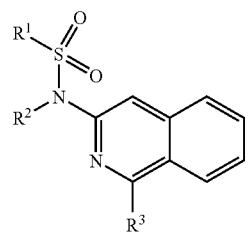

| | Compound name | R¹ | R³ | R² |
|---|---|---|---|---|
| 118 | N-[1-(4-methyl-1-piperazinyl)-3-isoquinolinyl]benzenesulfonamide, hydrochloride | 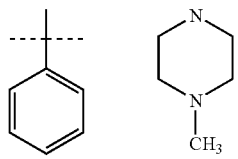 | | |

TABLE IV-continued

| | | | |
|---|---|---|---|
| 119 | 2,4-di-Fluoro-N-[1-(4-methyl-1-piperazinyl)-3-isoquinolinyl]benzenesulfonamide, hydrochloride | 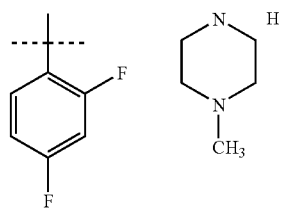 | |
| 120 | 4-Bromo-N-[1-(4-methyl-piperazin-1-yl)-isoquinolin-3-yl]-benzenesulfonamide, hydrochloride | 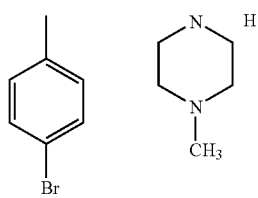 | |
| 121 | 5-Chloro-3-methyl-benzo[b]thiophene-2-sulfonic acid [1-(4-methyl-piperazin-1-yl)-isoquinolin-3-yl]-amide, hydrochloride | 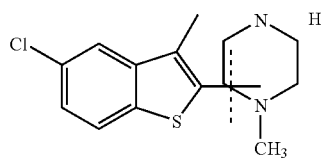 | |
| 122 | 3-Chloro-2-methyl-N-[1-(4-methyl-piperazin-1-yl)-isoquinolin-3-yl]-benzene sulfonamide, hydrochloride | 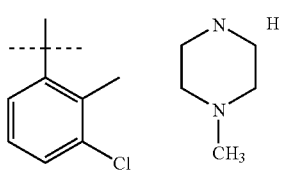 | |
| 123 | 3,4-Dichloro-N-[1-(4-methyl-piperazin-1-yl)-isoquinolin-3-yl]-benzenesulfonamide, hydrochloride | 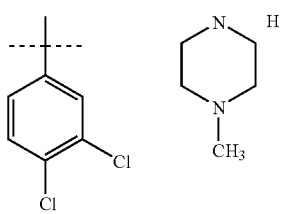 | |
| 124 | 4-Methyl-N-[1-(4-methyl-piperazin-1-yl)-isoquinolin-3-yl]-benzenesulfonamide, hydrochloride | 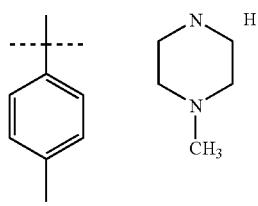 | |
| 125 | 3-Methoxy-N-[1-(4-methyl-piperazin-1-yl)-isoquinolin-3-yl]-benzenesulfonamide, hydrochloride | 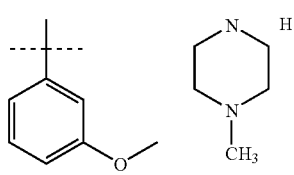 | |

TABLE IV-continued

| | | | |
|---|---|---|---|
| 126 | 5-Chloro-thiophene-2-sulfonic acid [1-(4-methyl-piperazin-1-yl)-isoquinolin-3-yl]-amide, hydrochloride | 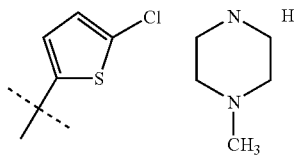 | |
| 127 | N-{2-Chloro-4-[1-(4-methyl-piperazin-1-yl)-isoquinolin-3-ylsulfamoyl]-phenyl}-acetamide hydrochloride | 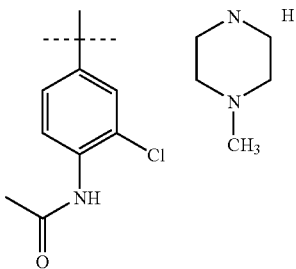 | |
| 128 | 2,5-Dichloro-thiophene-3-sulfonic acid [1-(4-methyl-piperazin-1-yl)-isoquinolin-3-yl]-amide, hydrochloride | 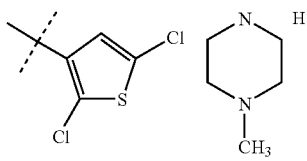 | |
| 129 | N-[1-(4-Methyl-piperazin-1-yl)-isoquinolin-3-yl]-3-trifluoromethyl-benzenesulfonamide, hydrochloride | 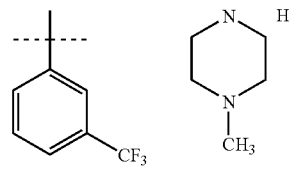 | |
| 130 | N-[1-(4-Methyl-piperazin-1-yl)-isoquinolin-3-yl]-4-phenoxy-benzenesulfonamide, hydrochloride | 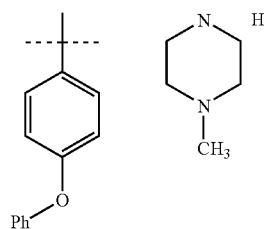 | |
| 131 | 5-Bromo-2-methoxy-N-[1-(4-methyl-piperazin-1-yl)-isoquinolin-3-yl]-benzenesulfonamide, hydrochloride | 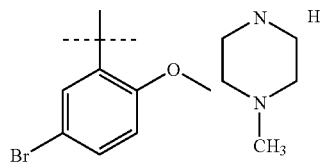 | |
| 132 | 2-Methanesulphonayl-N-[1-(4-methyl-piperazin-1-yl)-isoquinolin-3-yl]-benzenesulfonamide, hydrochloride | 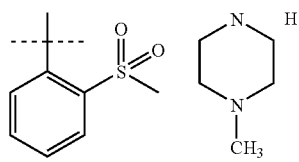 | |

TABLE IV-continued

| | | | |
|---|---|---|---|
| 133 | 3,5-Dimethyl-isoxazole-4-sulfonic acid [1-(4-methyl-piperazin-1-yl)-isoquinolin-3-yl]-amide, hydrochloride | 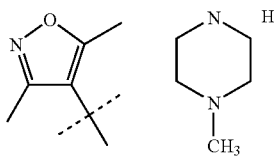 | |
| 134 | 2,4,6-Trimethyl-N-[1-(4-methyl-piperazin-1-yl)-isoquinolin-3-yl]-benzenesulfonamide, hydrochloride | 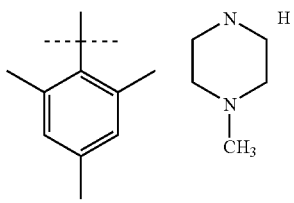 | |
| 135 | 3,4-Dimethoxy-N-[1-(4-methyl-piperazin-1-yl)-isoquinolin-3-yl]-benzenesulfonamide, hydrochloride | 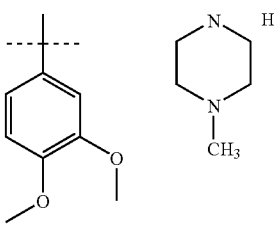 | |

TABLE V

5-Substituted quinoline compounds of the formula IV wherein P is

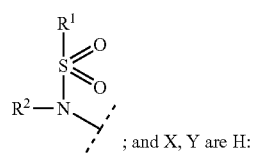 ; and X, Y are H:

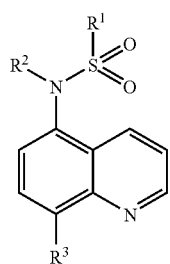

| Compound name | R$^1$ | R$^3$ | R$^2$ |
|---|---|---|---|
| 136 N-(8-{[2-(di-Methylamino)ethyl]-amino}-5-quinolinyl)benzene-sulfonamide, hydrochloride | 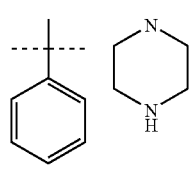 | | H |

TABLE VI 1,7-Naphthyridine compounds of the formula V wherein P is

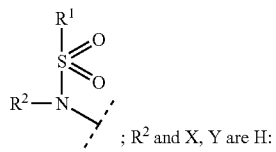 ; R$^2$ and X, Y are H:

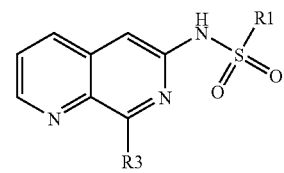

| Compound name | R1 | R3 |
|---|---|---|
| 137 4-Methyl-N-(8-piperazin-1-yl-1,7-naphthyridin-6-yl)benzene-sulfonamide, trifluoroacetic acid | 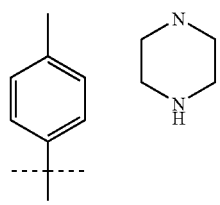 | |
| 138 4-Bromo-N-(8-piperazin-1-yl-1,7-naphthyridin-6-yl)benzene-sulfonamidetrifluoroacetic acid | 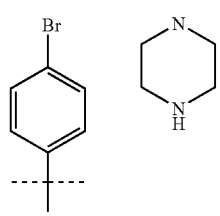 | |

TABLE VI-continued

| # | Name | Structure |
|---|---|---|
| 139 | N-(8-Piperazin-1-yl-1,7-naphthyridin-6-yl)naphthalene-1-sulfonamide, trifluoroacetic acid | 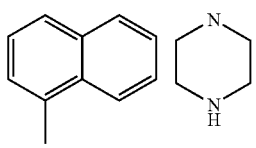 |
| 140 | N-(8-Piperazin-1-yl-1,7-naphthyridin-6-yl)butane-1-sulfonamide, trifluoroacetic acid | 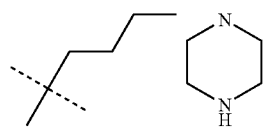 |
| 141 | 3-Trifluoromethyl-N-(8-piperazin-1-yl-1,7-naphthyridin-6-yl)benzenesulfonamide, trifluoroacetic acid | 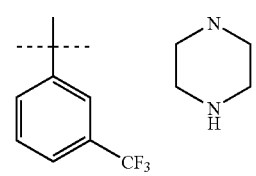 |
| 142 | 3,4-Dimethoxy-N-(8-piperazin-1-yl-1,7-naphthyridin-6-yl)benzenesulfonamide, trifluoroacetic acid | 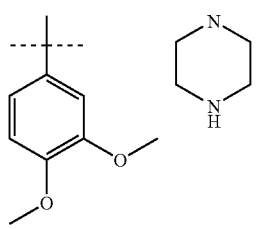 |
| 143 | 2,4-Dichloro-N-(8-piperazin-1-yl-1,7-naphthyridin-6-yl)benzenesulfonamide, trifluoroacetic acid | 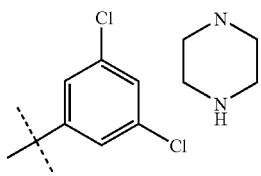 |
| 144 | N-(8-Piperazin-1-yl-1,7-naphthyridin-6-yl)thiophene-2-sulfonamide, trifluoroacetic acid | 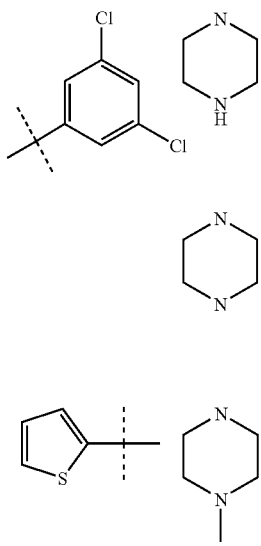 |
| 145 | 1-Phenyl-N-(8-piperazin-1-yl-1,7-naphthyridin-6-yl)methane-sulfonamide, trifluoroacetic acid | 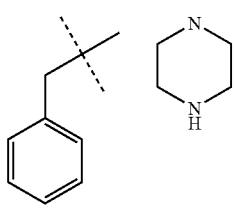 |

TABLE VII

5-Substituted benzofuran compounds of the formula VI wherein P is 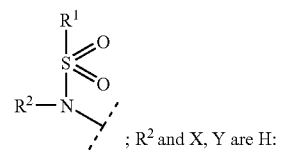; $R^2$ and X, Y are H:

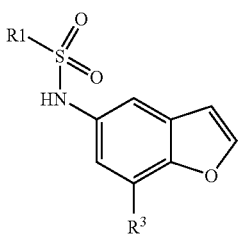

| Compound name | R1 | R3 |
|---|---|---|
| 146 3-Cyanophenyl-N-(7-piperazin-1-yl-benzofuran-5-yl)-benzenesulfonamide, hydrochloride | 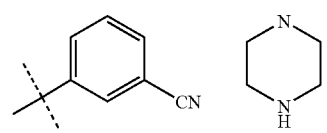 | |

TABLE VII-continued

| | | | |
|---|---|---|---|
| 147 | 4-Phenoxy-N-(7-piperazin-1-yl-benzofuran-5-yl)-benzenesulfonamide, hydrochloride | 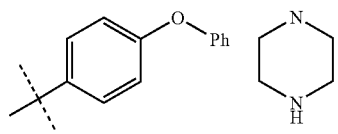 | |
| 148 | 1-Naphthyl-N-(7-piperazin-1-yl-benzofuran-5-yl)-benzenesulfonamide, hydrochloride | 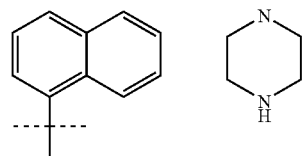 | |
| 149 | N-(7-Piperazin-1-yl-benzofuran-5-yl)-benzenesulfonamide, hydrochloride | 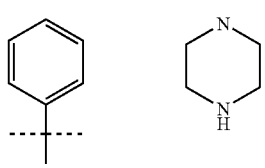 | |
| 150 | 5-Chloro-3-methyl-benzo[b]thiophene-2-sulfonic acid (7-piperazin-1-yl-benzofuran-5-yl)-amide, hydrochloride | 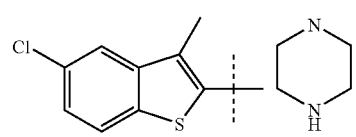 | |
| 151 | N-[7-(4-Methylpiperazin-1-yl)-1-benzofuran-5-yl]-benzenesulfonamide, hydrochloride | 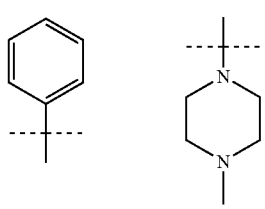 | |
| 152 | 4-Methyl-N-(7-piperazin-1-yl-benzofuran-5-yl)-benzenesulfonamide, hydrochloride | 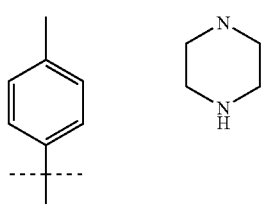 | |
| 153 | 3,4-Dimethoxy-N-(7-piperazin-1-yl-benzofuran-5-yl)-benzenesulfonamide, hydrochloride | 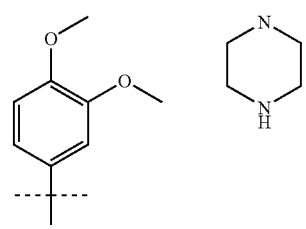 | |
| 154 | 4-Bromo-N-(7-piperazin-1-yl-benzofuran-5-yl)-benzenesulfonamide, hydrochloride | 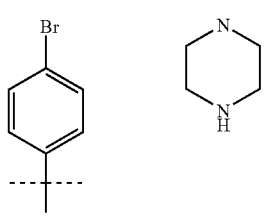 | |

TABLE VII-continued

| | | | |
|---|---|---|---|
| 155 | 2,3-Dichloro-N-(7-piperazin-1-yl-benzofuran-5-yl)-benzenesulfonamide, hydrochloride | 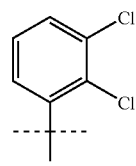 | 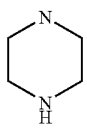 |
| 156 | 2,4-Dichloro-5-methyl-N-(7-piperazin-1-yl-benzofuran-5-yl)-benzenesulfonamide, hydrochloride | 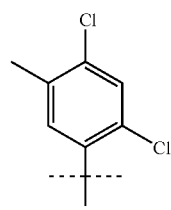 | 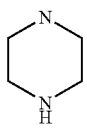 |
| 157 | 4-Methoxy-N-(7-piperazin-1-yl-benzofuran-5-yl)-benzenesulfonamide, hydrochloride | 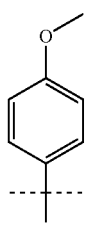 | 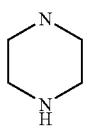 |
| 158 | 4-Chloro-N-(7-piperazin-1-yl-benzofuran-5-yl)-benzenesulfonamide, hydrochloride | 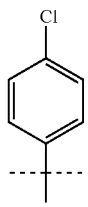 | 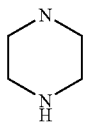 |
| 159 | N-(7-Piperazin-1-yl-benzofuran-5-yl)-4-trifluoromethyl-benzenesulfonamide, hydrochloride | 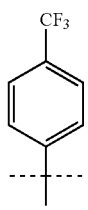 | 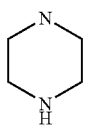 |
| 160 | 5-Fluoro-2-methyl-N-(7-piperazin-1-yl-benzofuran-5-yl)-benzenesulfonamide, hydrochloride | 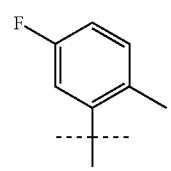 | 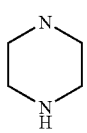 |
| 161 | 5-Chloro-thiophene-2-sulfonic acid (7-piperazin-1-yl-benzofuran-5-yl)-amide, hydrochloride | 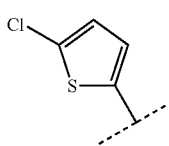 | 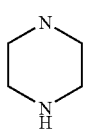 |

Methods for Preparation

The compounds according to the invention (Tables I, II, IV, V, VI) can be prepared starting from halo-nitro substituted bicyclic aromatic rings by base (potassium carbonate) catalyzed aromatic nucleophilic substitution of a halogen in the desired position of the central bicyclic ring with the diamine of choice ($R^3$). Reduction of a nitro group properly positioned on the central bicyclic ring by Raney-Ni catalyzed reaction leads to the aniline that is substituted further by sulfonylation with the alkyl- or aryl-sulfonylchloride of choice ($R^1$—$SO_2$—Cl). Scheme 1 and Scheme 3

The compounds according to the invention (Tables III) can be prepared starting from fluoro substituted bicyclic aromatic rings in which the sulfonylchloride functionality is introduced by acid catalyzed sulfonylation. The sulfonyl group is reacted further with anilines of choice ($R^1$—$NH_2$). The diamine group ($R^3$) is introduced by base catalyzed aromatic nucleophilic substitution. Scheme 2

The compounds according to the invention (Tables VII) can be prepared starting from iodo substituted bicyclic aromatic rings. The diamine group ($R^3$) is introduced by Palladium catalysed nucleophilic substitution. Reduction of a nitro group properly positioned on the central bicyclic ring by Raney-Ni catalyzed reaction leads to the aniline that is substituted further by sulfonylation with the alkyl- or aryl-sulfonylchloride of choice ($R^1$—$SO_2$—Cl). Scheme 4

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the compounds of formula (I). In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 2nd Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Depending on the process conditions, the end products of the formula (I) are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids, sulfuric acid, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbenzenesulfonic acid, toluenesulfonic acid, mandelic acid or naphthalenesulfonic acid.

Throughout the specification and the appended claims, a given chemical formula or name shall encompass all stereo and optical isomers and racemates thereof where such isomers exist. All diastereomeric forms possible (pure enantiomers, tautomers, racemic mixtures and unequal mixtures of two enantiomers) are within the scope of the invention. Such compounds can also occur as cis- or trans-, E- or Z- double bond isomer forms. All isomeric forms are contemplated.

Pharmaceutical formulations are usually prepared by mixing the active substance, or a pharmaceutically acceptable salt thereof, with conventional pharmaceutical excipients. The formulations can be further prepared by known methods such as granulation, compression, microencapsulation, spray coating, etc.

This invention relates to a method of treatment or prophylaxis of obesity, type II diabetes, and/or disorders of the central nervous system. The method includes administering to a subject (e.g., a mammal, a human, a horse, a dog, or a cat) in need thereof an effective amount of one or more compounds of the formula (I) described above.

This invention also features a method for reducing body-weight (e.g., treating body-weight disorders) or reducing food intake. The method includes administering to a subject in need thereof an effective amount of a compound of the formula (I). As used herein, the term "body weight disorders" refers to the disorders caused by an imbalance between energy intake and energy expenditure, resulting in abnormal body (e.g., excessive) weights. Such body weight disorders include obesity.

Also within the scope of this invention is a method for modulating (e.g., inhibiting) 5-$HT_6$ receptor activity. The method includes administering to a subject in need thereof an effective amount of a compound of the formula (I).

The methods delineated herein can also include the step of identifying that the subject is in need of treatment of obesity, type II diabetes, or disorders of the central nervous system, or in need of reducing body-weight or reducing food intake.

"An effective amount" refers to an amount of a compound which confers a therapeutic effect on the treated subject. The therapeutic effect may be objective (i.e., measurable by some test or marker) or subjective (i.e., subject gives an indication of or feels an effect). For clinical use, the compounds of the invention are formulated into pharmaceutical formulations for oral, rectal, parenteral or other mode of administration. Usually the amount of active compounds is between 0.1–95% by weight of the preparation, preferably between 0.2–20% by weight in preparations for parenteral use and preferably between 1 and 50% by weight in preparations for oral administration.

The typical daily dose of the active substance varies within a wide range and will depend on various factors such as, for example, the individual requirement of each patient and the route of administration. In general, oral and parenteral dosages will be in the range of 5 to 1000 mg per day of active substance, preferably 50 to 150 mg per day.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Synthesis of Examples and Intermediates in Table I

Scheme 1

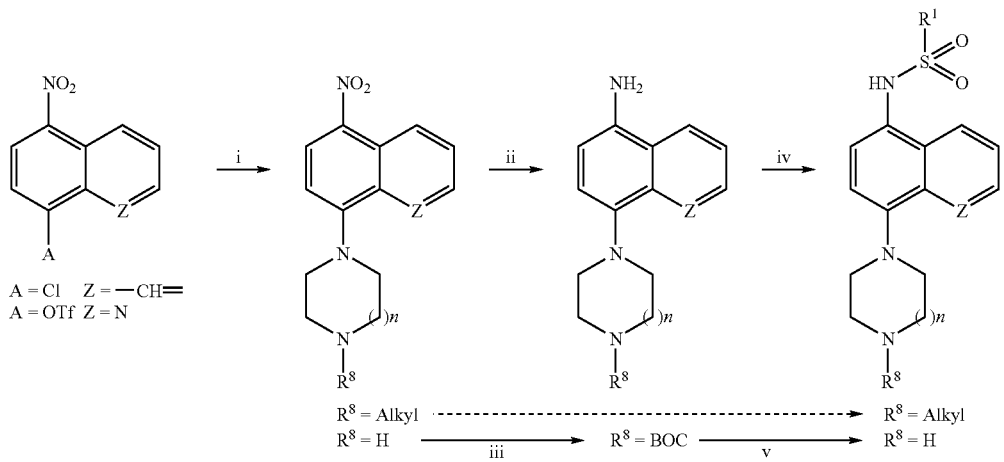

In scheme 1, the following symbols are used: (i) $K_2CO_3$, DMF, diamine of chioce; (ii) $H_2$, Raney-Ni or Pd/C, THF: Ethanol; (iii) $(BOC)_2O$, NaOH; (iv) $R^1$—$SO_2$—Cl, Py, $CH_2Cl_2$; (v) HCl in diethyl ether; (vi) alkylhalides. TfO=trifluoromethanesulfonate.

General Method A

Reduction of Nitronapthalenes Derivatives to Naphthylamine Derivatives

To a solution of nitronapthalenes derivatives (1 eq)in EtOH:THF (4:1) was added Raney-Ni (~1.0 mL suspension in EtOH) followed by hydrazine monohydrate (6 eq). The mixtures are stirred vigorously for 3 hours and then filtered through celite pretreated with water. The filtrate was concentrated, followed by the addition of toluene. Purifications are performed by flash column chromatography ($SiO_2$, $CHCl_3$/MeOH/$NH_3$ 9:1:0.4% and 2 parts of light petroleum) to obtain the free base of napthylamine derivatives.

General Method B

Reaction of 4-nitro-chloronaphthalenes with Diamines

Diamines (1.2 eq) are added to a suspension of chloronaphthalenes derivatives (1 eq) and $K_2CO_3$ (3.5) in DMF. The suspensions are stirred at 65° C. for 16 hours followed by filtration. Elimination of volatiles to give a crude residue. The residues are purified by flash chromatography ($SiO_2$, $CHCl_3$→$CHCl_3$/10% MeOH/0.4% aq. $NH_3$) to give the corresponding products as free bases.

(a) Intermediates for Preparation of Compounds in Tables I, II, IV and V According to Scheme I Intermediate 1

1-Methyl-4-(4-nitro-1-naphthyl)-1,4-diazepane—To a suspension of 1-chloro-4-nitronaphthalene (1.0 g, 4.82 mmol) and $K_2CO_3$ (2.0 g, 14.46 mmol) in DMF (10 mL) was added 1-methyl-1,4-diazepane (0.66 g, 5.78 mmol). The suspension was stirred at 65° C. for 16 hours followed by filtration. Elimination of volatiles to give a crude residue. The residue was purified by flash chromatography ($SiO_2$, $CHCl_3$→$CHCl_3$/10% MeOH/0.4% aq. $NH_3$) to give 0.79 g (57%) of the free base: $^1$H NMR ($CDCl_3$) δ 8.85–8.75 (m, 1H), 8.35–8.25 (m, 1H), 8.20–8.12 (m, 1H), 7.70–7.60 (m, 1H), 7.55–7.45 (m, 1H), 6.97–6.90 (m, 1H), 3.70–3.55 (m, 4H), 2.83–2.71 (m, 4H), 2.44 (s, 3H), 2.09–1.97 (m, 2H); $^{13}$C NMR ($CDCl_3$) δ 157.47, 139.13, 129.26, 127.82, 127.66, 126.53, 125.69, 125.40, 123.94, 111.22, 58.37, 57.37, 55.44, 54.71, 46.97, 27.88; MS (posES-FIA) m/z=found 285.1463. calc 285.1477.

Intermediate 2

4-(4-Methyl-1,4-diazepan-1-yl)-1-naphthylamine—To a solution of 1-methyl-4-(4-nitro-1-naphthyl)-1,4-diazepane (0.793 g, 2.78 mmol) in 40 mL of EtOH:THF (4:1) was added Raney-Ni (~1.0 mL suspension in EtOH) followed by hydrazine monohydrate (0.696 g, 13.9 mmol). The mixture was stirred vigorously for 3 hours and then filtered through celite pretreated with water. The filtrate was concentrated, followed by the addition of toluene. Purification by flash column chromatography ($SiO_2$, $CHCl_3$/MeOH/$NH_3$ 9:1:0.4% and 2 parts of light petroleum) gave 0.441 g (62%) of the free base: $^1$H NMR ($CDCl_3$) δ 8.37–8.29 (m, 1H), 7.85–7.76 (m, 1H), 7.55–7.40 (m, 2H), 7.07–7.01 (m, 1H), 6.75–6.68 (m, 1H), 3.96 (br s, 2H), 3.36–3.20 (m, 4H), 2.95–2.76 (m, 4H), 2.48 (s, 3H), 2.10–1.95 (m, 2H); MS (posESI) m/z=256 (M+H).

Intermediate 3

1-Ethyl-4-(4-nitro-1-naphthyl)piperazine—To a mixture of 1-chloro-4-nitronaphthalene (0.794 g, 3.82 mmol), and $K_2CO_3$ (0.791 g, 5.73 mmol) in DMF (3 mL) was added N-ethyl piperazine (0.486 mL, 3.82 mmol). The mixture was heated in a microwave oven at 100W for 1 minute. The reaction mixture was allowed to cool down and the procedure was repeated 5 times. The mixture was filtered and concentrated. The crude product was purified by column chromatography ($SiO_2$, $CHCl_3$→$CHCl_3$/MeOH/$NH_3$ 9:1:0.4%) to give 0.950 g (87%) of a reddish brown solid: $^1$H NMR ($CDCl_3$) δ; 8.75–8.70 (m, 1H), 8.30 (d, J=8.4 Hz, 1H), 8.24–8.20 (m, 1H), 7.72–7.66 (m, 1H), 7.60–7.54 (m, 1H), 7.02 (d, J=8.4 Hz, 1H), 3.32–3.24 (m, 4H), 2.85–2.70 (m, 4H), 2.54 (q, J=7.3 Hz, 2H), 1.17 (tr, J=7.3 Hz, 3); MS (posEI) m/z 385 ($M^+$).

Intermediate 4

(cis)-3,5-Dimethyl-1-(4-nitro-1-naphthyl)piperazine—This compound was prepared from 1-chloro-4-nitronaphthalene (0.481 g, 2.32 mmol) and cis-2,6-dimethylpiperazine (0.481 g, 2.32 mmol) by the method described above, yield 0.554 g (84%) of the pure product as a reddish brown solid; $^1$H NMR (CDCl$_3$) δ; 8.76–8.71 (m, 1H), 8.30 (d, J=8.4 Hz, 1H), 8.23–8.14 (m, 1H), 7.72–7.66 (m, 1H), 7.61–7.55 (m, 1H), 7.0 (d, J=8.4 Hz, 1H), 3.45–3.37 (m, 2H), 3.35–3.25 (m, 2H), 2.55–2.47 (m, 2H), 1.17–1.4 (m, 6H); MS (posEI) m/z 385 (M$^+$).

Intermediate 5

3-Methyl-1-(4-nitro-1-naphthyl)piperazine—This compound was prepared from 1-chloro-4-nitronaphthalene (0.395 g, 1.90 mmol) and 2-methylpiperazine (0.395 g, 1.90 mmol) by the method described above: yield 0.470 g (84%) of the pure product as a solid; $^1$H NMR (CDCl$_3$) δ 8.75–8.70 (m, 1H), 8.29 (d, J=8.55 Hz, 1H), 8.24–8.20 (m, 1H), 7.72–7.65 (m, 1H), 7.61–7.55 (m, 1H), 7.00 (d, J=8.55 Hz, 1H), 3.46–3.37 (m, 2H), 3.31–3.15 (m, 3H), 2.95–2.89 (m, 1H), 2.61–2.53 (m, 1H), 1.15 (d, J=6.4 Hz, 3H)); MS (EI) m/z 271 (M$^+$).

Intermediate 6

2-(4-Nitro-1-naphthyl)octahydropyrrolo[1,2-a]pyrazine—This compound was prepared from 1-chloro-4-nitronaphthalene (0.306 g, 1.47 mmol) and octahydropyrrolo[1,2-a]pyrazine (0.185 g, 1.47 mmol) by the method described above, yield 0.332 g (76%) of the pure product as a yellow oil; $^1$H NMR (CDCl$_3$) δ 8.75–8.71 (m, 1H), 8.29 (d, J=8.5 Hz, 1H), 8.23–8.20 (m, 1H), 7.72–7.67 (m, 1H), 7.60–7.55 (m, 1H), 7.05 (d, J=8.5 Hz, 1H), 3.64–3.59 (m, 1H), 3.54–3.48 (m, 1H), 3.27–3.10 (m, 3H), 2.90–2.80 (m, 1H), 2.70–2.65 (m, 1H), 2.60–2.30 (m, 2H), 2.00–1.80 (m, 3H), 1.65–1.50 (m, 1H); MS (posESI) m/z 298 (M+H).

Intermediate 7

1-(4-Nitro-1-naphthyl)-1,4-diazepane—To a solution of 1-chloro-4-nitronaphthalene (0.971 g, 4.68 mmol) and K$_2$CO$_3$ (0.973 g, 7.10 mmol) in CH$_3$CN (5.0 mL) was added homopiperazine (0.711 g, 7.10 mmol). The reaction mixture was heated in a closed sealed vessel at 120° C. in a microwave oven for 10 min. The suspension was filtered and concentrated. Purification by column chromatography (SiO$_2$, CHCl$_3$→CHCl$_3$/MeOH 9:1) gave 0.952 g of the pure product; $^1$H NMR (CDCl$_3$) δ 8.80–8.74 (m, 1H), 8.29 (d, J=8.5 Hz, 1H), 8.25–8.19 (m, 1H), 7.71–7.63 (m, 1H), 7.57–7.49 (m, 1H), 7.03 (d, J=8.5 Hz, 1H), 3.57–3.48 (m, 4H), 3.18–3.10 (m, 4H), 2.10–1.95 (m, 2H); MS (posEI) m/z 272 (M$^+$).

Intermediate 8 tert-Butyl 4-(4-nitro-1-naphthyl)-1-piperazinecarboxylate—1-Chloro-4-nitronaphthalene (2.7 g, 13 mmol), tert-butyl-1-piperazinecarboxylate (2.4 g, 13 mmol) and potassium carbonate (2 g) were heated together in DMSO (100 mL) at 90° C. overnight. The solution was allowed to cool to room temperature and poured into water (500 mL). The product was collected by filtration and recrystallised from methanol/water to yield 2.8 g (60%) of the title compound; mp 158.2° C.; $^1$H NMR (CDCl$_3$) δ 1.52 (s, 9 H), 3.2 (br, 4 H), 3.75 (br, 4 H), 7.04 (d, J=8.53 Hz, 1 H), 7.62 (t, J=7.02 Hz, 1H), 7.73 (t, J=7.02 Hz, 1 H), 8.25 (d, J=8.53 Hz, 1 H), 8.3 (d, J=8.54 Hz, 1 H), 8.73 (d, J=8.53 Hz, 1 H).

Intermediate 9

1-tert-Butyl 4-(4-{bis[(4-methylphenyl)sulfonyl]amino}-1-naphthyl)-1-piperazinecarboxylate—tert-Butyl 4-(4-nitro-1-naphthyl)-1-piperazinecarboxylate (1 g, 2.8 mmol) in ethanol (200 mL) was hydrogenated at atmospheric pressure over Pd/C (10%, 0.2 g) for 3 hours after which time the uptake of hydrogen ceased. The solution was filtered and evaporated. The residue was dissolved in toluene (100 mL) and evaporated to give an off white solid. The solid was dissolved in acetonitrile (50 mL) containing 4-dimethylaminopyridine (0.73 g). Toluene sulfonyl chloride (1.14 g, 6 mmol) was added and the mixture stirred at 35° C. overnight. Brine was added and the product extracted into ethyl acetate (2×100 mL). The organic extracts were dried over MgSO$_4$ and evaporated to give a pale brown solid which was re-crystallized from ethanol. Yield 1.04 g (58%) of a white solid. Mp 176–178; $^1$H NMR (400 MHz, CDCl$_3$) δ 1.40 (s, 9 H), 2.36 (s, 6 H), 3.0 (br, 4 H), 3.6 (br, 4 H), 6.81 (AB, J=8.03 Hz, 1 H), 6.89 (AB, J=8.03 Hz, 1 H), 7.17 (m, 1 H), 7.19 (d, J=7.53 Hz, 4 H), 7.32 (m, 1 H), 7.45 (d, J=8.53 Hz, 1 H), 7.70 (d, J=8.54 Hz, 4 H), 8.03 (d, J=8.03 Hz, 1 H).

Intermediate 10

1-tert-Butyl 4-(4-{[(4-methylphenyl)sulfonyl]amino}-1-naphthyl)-1-piperazinecarboxylate—1-tert-Butyl 4-(4-{bis[(4-methylphenyl)sulfonyl]amino}-1-naphthyl)-1-piperazinecarboxylate (1 g, 1.6 mmol) was dissolved in ethanol (50 mL). Potassium hydroxide (85%, 0.54 g) was added and the solution refluxed for 12 hours. The solution was poured into water (100 mL) and acidified with acetic acid (0.6 mL). The product precipitated and was collected by filtration, washed with water and dried. Yield 0.81 g; $^1$H NMR (400 MHz, CDCl$_3$) δ 1.36 (s, 9 H), 2.22 (s, 3 H), 2.8 (br, 4 H), 3.5 (br, 4 H), 6.47 (s, 1 H), 6.79 (d, J=8.03 Hz, 1 H), 7.03 (d, J=8.03 Hz, 2 H), 7.07 (d, J=8.03 Hz, 1 H), 7.3 (m, 2 H), 7.47 (d, J=8.53 Hz, 2 H), 7.69 (1, J=9.04 Hz, 1 H), 8.03 (d, J=7.02 Hz, 1 H).

Intermediate 11

1-tert-Butyl 4-(4-{methyl[(4-methylphenyl)sulfonyl]amino}-1-naphthyl)-1-piperazinecarboxylate—1-tert-Butyl 4-(4-{[(4-methylphenyl)sulfonyl]amino}-1-naphthyl)-1-piperazinecarboxylate (0.1 g, 0.2 mmol) was dissolved in DMSO (5 mL) and potassium carbonate (0.2 g) and methyl iodide (0.1 g) were added. The mixture was stirred and heated at 85° C. for 15 hours. The solution was poured into water (50 mL) and the product collected by filtration, washed with water and dried. Yield 0.078 g (78%) of a white solid. $^1$H NMR (400 MHz, CDCl$_3$) δ 1.60 (s, 9 H), 2.56 (s, 3 H), 3.1 (br, 4 H), 3.36 (s, 3 H), 3.7 (br, 4 H), 6.90 (AB, J=8.03 Hz, 1 H), 6.97 (AB, J=8.03 Hz, 1 H), 7.41 (d, J=8.03 Hz, 2 H), 7.6 (m, 2 H), 7.75 (d, J=8.29 Hz, 2 H), 8.3 (m, 2 H).

Intermediate 12

5-Nitro-8-quinolinyl trifluoromethanesulfonate—To a solution of 5-nitro-8-quinolinol (1.89 g, 9.40 mmol) and Et$_3$N (6.60 mL, 4.70 mmol) in CH$_2$Cl$_2$ (125 mL) was added N-phenyl-trifluoromethanesulfonimide (5.06 g, 14.1 mmol). The mixture was stirred at room temperature for 16 hours and then more of added N-phenyl-trifluoromethanesulfonimide (1.0 equiv.) was added and the mixture was stirred from another 16 hours. The reaction mixture was washed with 10% aqueous NaHCO$_3$, dried with K$_2$CO$_3$, filtered and concentrated. The crude residue was triturated in MeOH to give 1.2 g (40%) of the pure product: $^1$H NMR (CDCl$_3$) δ 9.20–9.18 (m, 1H), 9.11–9.07 (m, 1H), 8.48–8.45 (m, 1H), 7.83–7.79 (m, 1H), 7.76–7.72 (m, 1H); MS (posEI-DIP) m/z 321 (M+H).

Intermediate 13

8-(4-Methyl-1-piperazinyl)-5-nitroquinoline—To a suspension of 5-nitro-8-quinolinyl trifluoromethanesulfonate (0.50 g, 1.56 mmol) and $K_2CO_3$ (0.43 g, 3.12 mmol) in $CH_3CN$ (6.0 mL) was added 1-methylpiperazine (0.19 mL, 1.71 mmol). The suspension was stirred at room temperature for 16 hours. The mixture was filtered and concentrated. Purification via flash column chromatography chromatography ($SiO_2$, $CHCl_3/MeOH/NH_3$ 9:1:0.4%) gave 0.509 g of the pure product: reversed phase HPLC>95% purity; MS (posESI) m/z 273 (M+H).

Intermediate 14 tert-Buyl (2R,6S)-2,6-dimethyl-4-(4-nitro-1-naphthyl)-1-piperazinecarboxylate—To a solution of cis-3,5-dimethyl-1-(4-nitro-1-naphthyl)piperazine (0.565 g, 1.98 mmol) and NaOH (0.198 g, 4.95 mmol) in THF:water (20 mL, 1:1) was added di-tert-butyl dicarbonate (1.30 g, 5.94 mmol) in THF (4 mL). The reaction mixture was stirred at room temperature for 4 hours followed by the addition of 3.0 equiv. of di-tert-butyl dicarbonate and 2.5 equiv. of NaOH. The mixture was stirred at room temperature for another 3 days. The mixture was concentrated and extracted with $CHCl_3$ (3×20 mL). The combined organic phases were dried with $K_2CO_3$, filtered and concentrated. The crude residue was purified by column chromatography on silica using $CHCl_3$ as eluent gave 0.200 g (26%) of the pure product as a solid brown solid: MS (posESI) m/z 386 (M+H).

Intermediate 15 tert-Butyl-2-methyl-4-(4-nitro-1-naphthyl)-1-piperazinecarboxylate was prepared from 3-methyl-1-(4-nitro-1-naphthyl)piperazine (0.436 g, 1.61 mmol) by the method described above: yield 0.552 g (92%) of the pure product as a yellow oil; $^1H$ NMR ($CDCl_3$) δ 8.73–8.70 (m, 1H), 8.34–8.30 (m, 1H), 8.28 (d, J=8.5 Hz, 1H), 7.74–7.69 (m, 1H), 7.63–7.58 (m, 1H), 7.02 (d, J=8.5 Hz, 1H), 4.50–4.442 (m, 1H), 4.10–4.03 (m, 1H), 3.52–3.39 (m, 2H), 3.32–3.27 (m, 1H), 3.08–3.03 (m, 1H), 2.89–2.82 (m, 1H), 1.53 (s, 3H), 1.51 (s, 9H); MS (posESI) m/z 372 (M+H).

Examples of Compounds According to the Invention

Example 1

4-Methyl-N-[4-(1-piperazinyl)-1-naphthyl]benzenesulfonamide, hydrochloride 1-tert-Butyl 4-(4-{[(4-methylphenyl)sulfonyl]amino}-1-naphthyl)-1-piperazinecarboxylate (intermediate 10) (0.4 g, 0.8 mmol) was dissolved in THF (20 mL) and treated with a 1N solution of HCl in diethyl ether (30 mL) for twelve hours. The product was collected as a pale pink solid. Yield 0.2 g (60%). mp 181° C. (dec); $^1H$ NMR (DMSO-$d_6$) δ 2.80 (s, 3 H), 3.1 (br, 4 H), 3.3 (br, 4 H), 7.00 (q, J=8.06 Hz, 2 H), 7.27 (ab, J=8.30 Hz, 2 H), 7.4–7.5 (m, 2 H), 7.53 (ab, J=8.30 Hz, 2 H), 7.99 (d, J=8.06 Hz, 1 H), 8.07 (d, J=7.57 Hz, 1 H), 9.2 (br, 2 H); MS (ESI+) for C21 H23 N3 O2 S Found m/z 381.1499 M+. Calc. 381.1611.

Example 2

3,4-Dimethoxy-N-[4-(1-piperazinyl)-1-naphthyl]benzenesulfonamide, hydrochloride tert-Butyl 4-(4-nitro-1-naphthyl)-1-piperazinecarboxylate (1 g, 2.8 mmol) in ethanol (200 mL) was hydrogenated at atmospheric pressure over Pd/C (10%, 0.2 g) for 3 hours after which time the uptake of hydrogen ceased. The solution was filtered and evaporated. The residue was dissolved in toluene (100 mL) and evaporated to give an off white solid. The solid was dissolved in acetonitrile (50 mL) containing 4-dimethylaminopyridine (0.73 g). This solution was divided into three portions. To one portion was added 3,4-dimethoxybenzene sulfonyl chloride (0.24 g). The mixture was stirred for 4 hours at 40° C. under nitrogen. Ethyl acetate (50 mL) was added and the solution washed with brine (2×100 mL). The organic phase was separated, dried over $MgSO_4$ and evaporation. Purification by flash chromatography ($SiO_2$, Petrol:Ethyl acetate 1:1) afforded the butoxycarbonyl protected product which was dissolved in methanol (2 mL) and treated with a 1N solution of HCl in ethyl acetate (25 mL) for three hours. The product was precipitated with ether (200 mL) and collected as a pale pink solid, 45 mg (12%). $^1H$ NMR (DMSO-$d_6$) δ 3.17 (br, 4 H), 3.35 (br, 4 H), 3.63 (s, 3 H), 3.78 (s, 3 H), 7.03 (d, J=8.55 Hz, 1 H), 7.07 (ab, J=13.92, 8.06 Hz, 2 H), 7.24 (dd, J=8.30, 2.19 Hz, 1 H), 7.46 (m, 1 H), 7.51 (m, 1 H), 8.05 (d, J=7.57 Hz, 1 H), 8.12 (d, J=7.56 Hz, 1 H), 9.2 (br, 2 H), 9.93 (s, 1 H); MS (ESI+) for C22 H25 N3 O4 S m/z 427 (M+H)+.

Example 3

3,4-di-Fluoro-N-[4-(4-methyl-1,4-diazepan-1-yl)-1-naphthyl]benzenesulfonamide, hydrochloride To a solution of (intermediate 2) 4-(4-methyl-1,4-diazepan-1-yl)-1-naphthylamine (0.173 g, 0.676 mmol) and pyridine (0.450 mL, 4.73 mmol) in $CH_2Cl_2$ (3 mL) was added a solution of 2,4-Di-fluorobenzenesulfonyl chloride (0.158 g, 0.743 mmol) in $CH_2Cl_2$ (2 mL). The mixture was stirred at room temperature for 16 hours and then concentrated. The crude mixture was purified by column chromatography chromatography ($SiO_2$, $CHCl_3/MeOH/NH_3$ 9:1:0.4%). The free base was converted to its HCl-salt and recrystallized from MeOH and ether to give 0.227 g (79%) of the salt: $^1H$ NMR (DMSO-d6) δ 11.23 (br s, 1H), 10.49 (s, 1H), 8.21–8.17 (m, 1H), 7.72–7.65 (m, 1H), 7.55–7.46 (m, 3H), 7.19–7.10 (m, 3H), 3.65–3.35 (m, 6H), 3.30–3.15 (m, 2H), 2.85–2.82 (m, 3H), 2.33–2.10 (m, 2H); MS (posES-FIA) m/z 432 (M+H).

Example 4

3-Fluoro-N-[4-(4-methyl-1,4-diazepan-1-yl)-1-naphthyl]benzenesulfonamide, hydrochloride To a solution of (intermediate 3 after reduction according to Method A) 4-(4-methyl-1,4-diazepan-1-yl)-1-naphthylamine (0.173 g, 0.676 mmol) and pyridine (450 μL, 4.73 mmol) in $CH_2Cl_2$ (3.0 mL) was added 3-fluorobenzenesulfonyl chloride (0.145 g, 0.743 mmol) in $CH_2Cl_2$ (1.0 mL). The solution was stirred at room temperature for 16 hours and the volatiles were evaporated. The crude product was purified by column chromatography ($SiO_2$, $CHCl_3/MeOH/NH_3$ 9:1:0.4%) to give 240 mg of the product as solid that was triturated with MeOH/ether to give 0.180 g (64%) of the free base which was converted to its HCl-salt: $^1H$ NMR (DMSO-d6) δ 11.07 (br s, 1H), 10.28 (br s, 1H), 8.20–8.16 (m, 1H), 7.98–7.94 (m, 1H), 7.60–7.40 (m, 6H), 7.16–7.12 (m, 1H), 7.06–7.02 (m, 1H), 3.65–3.30 (m, partly obscured by solvent signal, HDO, 6H), 3.26–3.18 (m, 2H), 2.84 (s, 3H), 2.30–2.05 (m, 2H); MS (posES-FIA) m/z=414 (M+H).

Example 5

N-[4-(4-Ethyl-1-piperazinyl)-1-naphthyl]benzenesulfonamide, hydrochloride

The title compound was prepared from (intermediate 3 after reduction according to Method A) 4-(4-ethyl-1-piperazinyl)-1-naphthylamine (0.241 g, 0.945 mmol) and benzenesulfonyl chloride (0.121 mL, 0.945 mmol) by the method described above to yield HCl-salt 0.210 g (51%); $^1$H NMR (CD$_3$OD) δ 8.19–8.15 (m, 1H), 7.94–7.90 (m, 1H), 7.70–7.66 (m, 2H), 7.56–7.46 (m, 2H), 7.44–7.36 (m, 3H), 7.19 (d, J=8.0 Hz, 1H), 7.11 (d, J=8.0 Hz, 1H), 3.75–3.40 (m, 6H), 3.34 (q, J=7.6 Hz, 2H), 3.25–3.10 (m, 2H), 1.43 (tr, J=7.6 Hz, 3H); MS(posEI) m/z 387 (M$^+$).

Example 6

N-(4-Hexahydropyrrolo[1,2-a]pyrazin-2(1H)-yl-1-naphthyl)-4-methylbenzenesulfonamide, hydrochloride To a solution of (intermediate 6) 2-(4-nitro-1-naphthyl)octahydropyrrolo[1,2-a]pyrazine (0.160 g, 0.54 mmol) in 10 mL THF:EtOH (20 mL,1:4) was added Raney-Ni (1.0 mL suspension in EtOH) followed by hydrazine hydrate (0.135 g, 2.70 mmol). The mixture was stirred vigorously at room temperature for 16 hours and then filtered through celite pretreated with water. The filtrate was concentrated and the residue was dissolved in CH$_2$Cl$_2$ (3 mL) and pyridine (0.35 mL, 3.78 mmol) and p-toluensulfonyl chloride (0.13 g, 0.54 mmol) were added to the solution. The reaction mixture was stirred at room temperature for 16 hours and then concentrated. The crude product was purified by column chromatography chromatography (SiO$_2$, CHCl$_3$/MeOH/NH$_3$ 9:1:0.4%) to give 0.217 g (95%) of the free base which was converted to its HCl-salt: $^1$H NMR (CD$_3$OD) δ 8.21–8.14 (m, 1H), 7.97–7.93 (m, 1H), 7.58–7.47 (m, 3H), 7.43–7.37 (m, 1H), 7.25–7.10 (m, 4H), 4.12–4.02 (m, 1H), 3.80–3.0 (m, partly obscured by solvent signal, 8H), 2.45–2.10 (m, 3H), 2.35 (s, 3H), 1.87–1.75 (m, 1H); MS (posEI) m/z 421 (M$^+$).

Example 7

N-(4-Hexahydropyrrolo[1,2-a]pyrazin-2(1H)-yl-1-naphthyl)-3,4-dimethoxybenzenesulfonamide, hydrochloride The title compound was prepared from (intermediate 6) 2-(4-nitro-1-naphthyl)octahydropyrrolo[1,2-a]pyrazine (0.133 g, 0.447 mmol) by the method described above: yield 0.160 g (76%) of the pure product as the free base which was converted to its HCl-salt; $^1$H NMR (CD$_3$OD) δ 8.20–8.16 (m, 1H), 7.96–7.92 (m, 1H), 7.54–7.48 (m, 1H), 7.43–7.38 (m, 1H), 7.30–7.26 (m, 1H), 7.23 (d, J=8.0 Hz, 1H), 7.16 (d, J=8.0 Hz, 1H), 7.09–7.07 (m, 1H), 6.95–6.92 (m, 1H), 3.83 (s, 3H), 3.82–3.0 (m, partly obscured by solvent signal, 10H), 3.62 (s, 3H), 2.50–2.10 (m, 2H); MS (posEI) m/z 467 (M$^+$).

Example 8

N-[4-(4-Ethyl-1-piperazinyl)-1-naphthyl]-4-methylbenzenesulfonamide, hydrochloride To a solution of (intermediate 3 after reduction according to Method A) 4-(4-ethyl-1-piperazinyl)-1-naphthylamine (0.241 g, 0.945 mmol) and pyridine (0.534 mL, 0.945 mmol) in CH$_2$Cl$_2$ (3.0 mL) was added p-toluenesulfonyl chloride (0.180 g, 0.945 mmol) in CH$_2$Cl$_2$ (2.0 mL). The mixture was stirred at room temperature for 16 hours followed by the addition of CH$_2$Cl$_2$ (15 mL). The reaction mixture was washed with saturated aqueous NaHCO$_3$, dried with Na$_2$SO$_4$, filtered and concentrated. The crude residue was purified by column chromatography (SiO$_2$, CHCl$_3$→CHCl$_3$/MeOH/NH$_3$ 9:1:0.4%) to give a solid which was converted to its HCl-salt: yield HCl-salt 0.372 g (88%); $^1$H NMR (CD$_3$OD) δ 8.20–8.15 (m, 1H), 7.97–7.93 (m, 1H), 7.58–7.54 (m, 2H), 7.53–7.47 (m, 1H), 7.43–7.37 (m, 1H), 7.25–7.20 (m, 2H), 7.18 (d, J=8.0 Hz, 1H), 7.10 (d, J=8.0 Hz, 1H), 3.80–3.10 (m, partly obscured by solvent signal, 10 H), 2.35 (s, 3H), 1.43 (tr, J=7.3 Hz, 3H); MS (posEI) m/z 409 (M$^+$).

Example 9

3,4-Dimethoxy-N-[4-(3-methyl-1-piperazinyl)-1-naphthyl]benzenesulfonamide, hydrochloride The title compound was prepared from (intermediate 8 after reduction according to Method A) tert-butyl 4-(4-amino-1-naphthyl)-2-methyl-1-piperazinecarboxylate (0.189 g, 0.55 mmol) and 3,4-dimethoxybenzenesulfonyl chloride (0.130 g, 0.55 mmol) by the method described above: yield HCl-salt 0.068 g (26%); 1H NMR (CD$_3$OD)

Example 10

4-Methyl-N-[4-(4-methyl-1-piperizinyl)-1-naphthyl]-1-benzenesulfonamide, hydrochloride To a solution of 4-(4-methyl-1-piperazinyl)-1-naphthylamine (prepared according to methods A and B) (0.099 g, 0.409 mmol) and pyridine (231 µL, 2.86 mmol) in CH$_2$Cl$_2$ (3.0 mL) was added 4-methylbenzenesulfonyl chloride (0.078 g, 0.409 mmol) in CH$_2$Cl$_2$ (1.0 mL). The solution was stirred at room temperature for 16 hours and then washed with saturated aqueous NaHCO$_3$, dried with Na$_2$SO$_4$, filtered and concentrated. The crude product was purified via column chromatography (SiO$_2$, CHCl$_3$→CHCl$_3$/MeOH/NH$_3$ 9:1:0.4%) to give the pure base which was converted to its HCl-salt: yield 110 mg (62%); $^1$H NMR (DMSO-d6) δ 10.86 (br s, 1H), 10.02 (s, 1H), 8.11–8.03 (m, 2H), 7.60–7.56 (m, 2H), 7.55–7.44 (m, 2H), 7.33–7.30 (m, 2H), 7.09–7.06 (m, 1H), 7.04–7.01 (m, 1H), 3.55–3.32 (m, 6H), 3.19–3.10 (m, 2H), 2.86 (s, 3H), 2.34 (s, 3H); MS (posES-FIA) m/z=395.1665 (M+H)(calc 395.1667).

Example 11

4-Methyl-N-[4-(5-methyl-2,5-diazabicyclo[2,2,1]hept-2-yl]-naphtyl]benzenesulfonamide, hydrochloride To a solution of 4-(5-methyl-2,5-diazabicyclo[2,2,1]hept-2-yl)-1-naphtylamine (0.210 g, 0.829 mmol) (prepared according to methods A and B), pyridine (468 µL, 5.80 mmol) in CH$_2$Cl$_2$ (3.0 mL) was added 4-methylbenzenesulfonyl chloride (0.158 g, 0.829 mmol) in CH$_2$Cl$_2$ (1.0 mL). The solution was stirred at room temperature for 16 hours and then concentrated. The crude product was purified via column chromatography (SiO$_2$, CHCl$_3$→CHCl$_3$/MeOH/NH$_3$ 9:1:0.4%) to give the pure base which was converted to its HCl-salt: yield 160 mg (43%); $^1$H NMR (DMSO-d6) δ

10.78 (br s, 1H), 9.90–9.88 (m, 1H), 8.02–7.98 (m, 2H), 7.58–7.55 (m, 2H), 7.49–7.41 (m, 2H), 7.33–7.30 (m, 2H), 7.06–7.03 (m, 1H), 6.93–6.90 (m, 1H), 4.38–4.30 (m, 3H), 3.65–3.60 (m, 3H), 2.90–2.87 (m, 3H), 2.86–2.83 (m, 3H), 2.36 (br s, 2H), 2.35 (s, 3H); MS (posES-FIA) m/z=407.1655 (M+H)(calc 407.1667).

Example 12

4-Methyl-N-[4-(3-methyl-1-piperazinyl)-1-naphthyl] benzenesulfonamide, hydrochloride To a solution of (intermediate 8 after resuction according to Method A) tert-butyl 4-(4-amino-1-naphthyl)-2-methyl-1-piperazinecarboxylate (0189 g, 0.55 mmol) and pyridine (0.311 mL, 3.85 mmol) in $CH_2Cl_2$ (3 mL) was added tolouenesulfonyl chloride (0.105 g, 0.55 mmol). The mixture was stirred at room temperature for 16 hours and then concentrated. The crude residue was purified by column chromatography ($SiO_2$, EtOAc:pentane 3:7). The pure intermediate was dissolved in small amount of MeOH and de-protected using ether saturated with HCl-gas. The precipitate was collected by filtration and triturated with MeOH and ether: yield HCl-salt 0.047 g (19%); $^1$H NMR ($CDCl_3$) δ 8.28–8.20 (m, 1H), 7.85–7.79 (m, 1H), 7.65–7.55 (m, 1H), 7.50–7.10 (m, partly obscured by solvent signal, 5H), 6.95–6.85 (m, 1H), 6.51 (br s, 1H), 4.50–4.25 (m, 1H), 4.05–3.85 (m, 1H), 3.52–3.33 (m, 1H), 3.28–3.05 (m, 2H), 2.97–2.85 (m, 1H), 2.82–2.67 (m, 1H), 2.85 (s, 3H), 1.52–1.47 (m, partly obscured by $H_2O$ signal, 3H); MS (pos-ES) m/z=395 (M+H).

Example 13

2-N-[4-(1-Piperazinyl)-1-naphthyl]naphthalene-sulfonamide, hydrochloride

To another portion of the solution of the reduced nitro compound was added 2-naphthalenesulfonyl chloride (0.23 g). The mixture was stirred for 4 hours at 40° C. under nitrogen and worked up as above. The product obtained was identified as 1-tert-butyl 4-(4-{bis[(2-naphthalene)sulfonyl]amino}-1-naphthyl)-1-piperazinecarboxylate. This bis sulfonamide was refluxed for 3 hours in ethanol (10 mL) containing NaOH (0.1 g). This solution was added to a solution of HCl in ethyl acetate (1 N, 100 mL) and stirred overnight. The solution was evaporated to give the crude product which was purified by preparative hplc ($CH_3CN$:$H_2O$ 10% to 50% gradient). Yield 47 mg. $^1$H NMR (400 MHz, DMSO-$d_6$) δ 3.05 (br, 4 H), 3.3 (br, 4 H), 7.0 (s, 2 H), 7.2–7.5 (m, 2 H), 7.55 (t, J=7.9 Hz, 1 H), 7.62 (t, J=6.9 Hz, 1 H), 7.76 (m, 1 H), 7.9–8.1 (m, 5 H), 8.21 (s, 1 H), 8.7 (br, 2 H)

Example 14

N,4-Dimethyl-N-[4-(1-piperazinyl)-1-naphthyl]benzenesulfonamide, hydrochloride 1-tert-Butyl 4-(4-{methyl[(4-methylphenyl)sulfonyl]amino}-1-naphthyl)-1-piperazinecarboxylate (intermediate 14 after reduction according to Method A) (75 mg, 0.15 mmol) was dissolved in methanol (5 mL) and treated with 1N HCl in ether (20 mL). After stirring overnight, the product precipitated and was collected by filtration, washed with ether and dried. Yield 60 mg (92%) of an off white solid.

Example 15

N-[4-(1,4-Diazepan-1-yl)-1-napthyl]-4-methylbenzenesulfonamide, hydrochloride

To a solution of (intermediate 7 after reduction according to Method A) 4-(1,4-diazepan-1-yl)-1-naphtylamine (0.399 g, 1.17 mmol), pyridine (661 μL, 8.19 mmol) and $Et_3N$ (329 μL, 2.34 mmol in $CH_2Cl_2$ (3.0 mL) was added 4-methylbenzenesulfonyl chloride (0.223 g, 1.17 mmol) in $CH_2Cl_2$ (1.0 mL). The solution was stirred at room temperature for 16 hours and then concentrated. The crude product was purified via column chromatography ($SiO_2$, $CHCl_3 \rightarrow CHCl_3$/MeOH/$NH_3$ 9:1:0.4%) to give 0.360 g of the boc-protected compound. De-protection was accomplished by dissolving the intermediate in MeOH and then adding HCl-gas dissolved in ether. The precipitate was collected by filtration to give 0.143 g (28%) of the pure compound as the HCl-salt: $^1$H NMR (DMSO-d6) δ 10.00 (s, 1H), 9.28 (br s, 1H), 8.20–8.16 (m, 1H), 8.04–7.99 (m, 1H), 7.60–7.55 (m, 2H), 7.54–7.49 (m, 1H), 7.47–7.42 (m, 1H), 7.33–7.29 (m, 2H), 7.12 (d, J=8.16 Hz, 1H), 7.01 (d, J=8.16 Hz, 1H), 3.42–3.31 (m, 6H), 3.20.3.16 (m, 2H), 2.34 (s, 3H), 2.14–2.08 (m, 2); MS (posES-FIA) m/z=395.1667 (M+H) (calc 395.1667)

Example 16

N-[4-(1,4-Diazepan-1-yl)-1-naphthyl]-2-methoxy-4-methylbenzenesulfonamide, hydrochloride To a solution of (intermediate 7 after reduction according to Method A) 4-(1,4-diazepan-1-yl)-1-naphtylamine (0.399 g, 1.17 mmol), pyridine (661 μL, 8.19 mmol) and $Et_3N$ (329 μL, 2.34 mmol in $CH_2Cl_2$ (3.0 mL) was added 2-methoxy-4-methylbenzenesulfonyl chloride (0.258 g, 1.17 mmol) in $CH_2Cl_2$ (1.0 mL). The solution was stirred at room temperature for 16 hours and then concentrated. The crude product was dissolved in EtOH and powdered KOH was added to the solution. The mixture was stirred at 70° C. for 16 hours. The suspension was concentrated and water was added. The solution was neutralized with 1N HCl and extracted with $CH_2Cl_2$ (2×20 mL). The combined organic phases were washed with brine, dried with $Na_2SO_4$, and concentrated. Column chromatography ($SiO_2$, $CH_2Cl_2 \rightarrow CH_2Cl_2$/MeOH (95:5) gave 0.432 g of a reddish brown solid. De-protection of the intermediate using MeOH ether saturated with HCl-gas gave brown solid which was collected by filtration. The product was re-crystallized from MeOH/ether to give 109 mg (20%) of product as its HCl-salt: $^1$H NMR (DMSO-d6) δ 9.74 (s, 1H), 9.36 (br s, 2H), 8.20–8.14 (m, 2H), 7.55–7.45 (m, 3H), 7.44–7.42 (m, 1H), 7.16–7.09 (m, 2H), 7.02–7.00 (m, 1H), 6.75–6.74 8m, 1H), 3.85 (s, 3H), 3.42–3.27 (m, 6H), 3.18–3.14 (m, 2H), 2.31-(s, 3H), 2.14–2.07 (m, 2H); MS (posES-FIA) m/z=425.1768 (M+H)(calc 425.1774)

Example 17

N-(2-Methoxy-4-methylphenyl)-4-(3,5-trimethyl-1-piperazinyl)-1-naphthalenesulfonamide, hydrochloride To a solution of (intermediate 4 after reduction according to Method A) 4-(2,6-dimethyl-1-piperazinyl)-1-naphthylamine (0.203 g, 0.563 mmol) and pyridine (322 μL, 3.99 mmol) in DCM (3.0 mL) was added 4-methylbenzenesulfonyl chloride (0.107 g, 0.563 mmol) in DCM (1.0 mL). The solution was stirred at room temperature for 16 hours and then washed with saturated aqueous NaHCO₃, dried with Na₂SO₄, filtered and concentrated. The crude intermediate was purified via column chromatography on silica using CHCl₃/CHCl₃+10% MeOH+0.4% NH₃ to give 0.230 g of the boc-protected intermediate. Removal of the boc-group was accomplished by dissolving the intermediate in MeOH and then adding ether saturated with HCl-gas. The crude product was dissolved in DCM and then purified via column chromatography on silica using CHCl₃/CHCl₃+10% MeOH+0.4% NH₃ to give 156 mg (67%) of the pure base which was converted to its HCl-salt: 1H NMR (DMSO-d6) δ 10.01 (s, 1H), 9.86–9.78 (m, 1H), 9.14–9.00 (m, 1H), 8.13–8.10 (m, 1H), 8.05–8.02 (m, 1H), 7.58–7.55 (m, 2), 7.53–7.49 (m, 1H), 7.48–7.43 (m, 1H), 7.33–7.29 (m, 2H), 7.06 (d, J=7.85 Hz, 1H), 7.02 (d, J=8.17 Hz, 1H), 3.65–3.55 (m, 2H), 3.35–3.27 (m, 2H), 2.86–2.79 (m, 2H), 2.34 (s, 3H), 1.31 (d, J=6.60 Hz, 6H); MS (posES-FIA) m/z=409.1838 (M+H)(calc 407.1824)

Example 18

N-[4-(4-Isopropyl-1-piperizinyl)-1-naphthyl]-4-methylbenzenesulfonamide, hydrochloride To a solution of 4-(4-isopropyl-1-piperazinyl)-1-naphthylamine (0.209 g, 0.776 mmol) (prepared according to Methods A and B) and pyridine (438 μL, 5.43 mmol) in CH₂Cl₂ (3.0 mL) was added 4-methylbenzenesulfonyl chloride (0.163 g, 0.850 mmol) in CH₂Cl₂ (1.0 mL). The solution was stirred at room temperature for 16 hours and the solid was collected by filtration as the HCl-salt to yield 0.236 g (66%); ¹H NMR (DMSO-d6) δ 10.65 (br s, 1H), 9.95 (br s, 1H), 8.10–8.05 (m, 1H), 8.02–7.94 (m, 1H), 7.56–7.49 (m, 2H), 7.48–7.37 (m, 2H), 7.28–7.22 (m, 2H), 7.02–6.94 (m, 2H), 3.53–3.40 (m, 3H), 3.37–3.15 (m, 8H), 2.28 (s, 3H), 1.32–1.28 (m, 6H); MS (posES-FIA) m/z=423.1972 (M+H) (calc 423.1980).

Example 19

4-Bromo-N-(4-piperazin-1-yl-naphthalen-1-yl)-benzenesulfonamide, hydrochloride

¹H NMR (DMSO-d6) δ; 10.21 (s, 1H), 9.12 (brs, 2H), 8.12 (d, J=8.48 Hz, 1H), 7.97 (d, J=8.16 Hz., 1H), 7.75–7.70 (m, 2H), 7.61–7.57 (m, 2H), 7.54–7.49 (m, 1H), 7.48–7.43 (m, 1H), 7.10–7.01 (M, 2h), 3.38–3.31 (M, 4H), 3.23–3.10 (M, 4H), MS (posESI) m/z=446 (M+H).

Example 20

2,5-Dichloro-N-[4-(1-piperazinyl)-1-naphthyl]benzenesulfonamide, hydrochloride

¹H NMR (400 MHz, DMSO-d₆) δ 3.2 (br, 4 H), 3.4 (br, 4 H), 7.09 (s, 2 H), 7.54 (m, 2 H), 7.70 (m, 3 H), 8.10 (m, 2 H); MS (ESI+) for C20 H19 Cl2 N3 O2 S m/z 436 (M+H)⁺.

Example 21

2-Chloro-4-fluoro-N-[4-(1-piperazinyl)-1-naphthyl] benzenesulfonamide, hydrochloride ¹H NMR (400 MHz, DMSO-d₆) δ 3.1 (br, 4 H), 3.4 (br, 4 H), 7.01 (AB, J=8.03 Hz, 1 H), 7.04 (AB, J=8.03 Hz, 1H), 7.27 (dt, J=3.01, 8.53 Hz, 1 H), 7.5 (m, 2 H), 7.68 (dd, J=2.51, 9.03 Hz, 1 H), 7.85 (dd, J=6.52, 9.03 Hz, 1 H), 8.10 (d, J=7.03 Hz, 1 H), 8.20 (d, J=7.03 Hz, 1 H); MS (ESI+) for C20 H19 Cl F N3 O2 S m/z 420 (M+H)⁺.

Example 22

2,3-Dichloro-N-[4-(1-piperazinyl)-1-naphthyl]benzenesulfonamide, hydrochloride

¹H NMR (400 MHz, DMSO-d₆) δ 3.1 (br, 4 H), 3.4 (br, 4 H), 7.01 (AB, J=8.03 Hz, 1 H), 7.03 (AB, J=8.03 Hz, 1 H), 7.42 (t, J=7.78 Hz, 1 H), 7.50 (m, 2 H), 7.81 (dd, J=1.51, 8.03 Hz, 1 H), 7.85 (dd, J=1.51, 8.03 Hz, 1 H), 8.10 (dd, J=6.52, 2.0 Hz, 1 H), 8.20 (dd, J=7.53, 2.01 Hz, 1 H); MS (ESI+) for C20 H19 Cl2 N3 O2 S m/z 436 (M+H)⁺.

Example 23

2,4-Dichloro,5-methyl-N-[4-(1-piperazinyl)-1-naphthyl]benzenesulfonamide, hydrochloride ¹H NMR (400 MHz, DMSO-d₆) δ 2.27 (s, 3 H), 3.15 (br, 4 H), 3.4 (br, 4 H), 7.07 (s, 2 H), 7.54 (m, 2 H), 7.79 (s, 1 H), 7.85 (s, 1 H), 8.13 (m, 1 H), 8.19 (m, 1 H); MS (ESI+) for C21 H21 Cl2 N3 O2 S m/z 450 (M+H)⁺.

Example 24

3-Trifluoromethyl-N-[4-(1-piperazinyl)-1-naphthyl] benzenesulfonamide, hydrochloride ¹H NMR (400 MHz, DMSO-d₆) δ 3.2 (br, 4 H), 3.4 (br, 4 H), 7.05 (AB, J=8.03 Hz, 1 H), 7.10 (AB, J=8.03 Hz, 1 H), 7.40 (t, J=7.53 Hz, 1 H), 7.50 (t, J=7.53 Hz, 1 H), 7.76 (t, J=8.03 Hz, 1 H), 7.81 (s, 1 H), 7.88 (d, J=8.53 Hz, 1 H), 7.95 (d, J=8.03 Hz, 1 H), 7.99 (d, J=8.03 Hz, 1 H), 8.12 (d, J=8.54 Hz, 1 H); MS (ESI+) for C21 H20 F3 N3 O2 S m/z 436 (M+H)⁺.

Example 25

2-Trifluoromethyl-N-[4-(1-piperazinyl)-1-naphthyl] benzenesulfonamide, hydrochloride ¹H NMR (400 MHz, DMSO-d₆) δ 3.0 (br, 4 H), 3.4 (br, 4 H), 6.93 (s, 2H), 7.36 (m, 1 H), 7.41 (m, 1 H), 7.64 (m, 2 H), 7.85 (dd, J=2.01, 7.53 Hz, 1 H), 7.90 (dd, J=2.01, 7.03 Hz, 1 H), 8.02 (d, J=8.54 Hz, 2 H).

Example 26

4-Bromo-N-methyl-N-(4-piperazin-1-yl-naphthalen-1-yl)-benzenesulfonamide, hydrochloride ¹H NMR (DMSO-d6) δ; 9.12 (brs, 2H), 8.22–8.07 (m, 2H), 7.89 (d, J=8.44 Hz, 2H), 7.74–7.58 (m, 4H), 7.10 (d, J=7.91 Hz, 1H), 6.89 (d, 8.18 Hz, 1H), 3.50 (s, 3H), 3.43–3.27 (m, obscured in part by solvent signal), MS posESI) m/z=460 (M+H).

Example 27

Naphthalene-1-sulfonic acid (4-piperazin-1-yl-naphthalen-1-yl)-amide, hydrochloride ¹H NMR (DMSO-d6) δ; 9.00 (brs, 1H), 8.77–8.71 (m, 1H), 8.18 (d, J=8.44 Hz, 1H), 8.10–8.02 (m, 2H), 8.01–7.96

(m, 1H), 7.90 (d, J=8.18 Hz, 1H), 7.73–7.62 (m, 2H), 7.56–7.49 (m, 1H), 7.47–7.39 (m, 1H), 7.31–7.23 (m, 1H), 7.02–6.94 (m, 2H), 3.40–3.25 (m, obscured by solvent signal), 3.19–3.05 (m, 4H), MS (posESI) m/z=418 (M+H).

Example 28

2,5-Dichloro-thiophene-3-sulfonic acid (4-piperazin-1-yl-naphthalen-1-yl)-amide, hydrochloride $^1$H NMR (DMSO-d6) δ; 10.52 (brs, 1H), 9.02 (brs, 2H), 8.19–8.12 (m, 1H), 8.01–7.94 (m, 1H), 7.60–7.47 (m, 2H), 7.23–7.12 (m, 3H), 3.43–3.28 (m, obscured in part by solvent signal), 3.25–3.10 (m, m, 4H), MS (posESI) m/z=442 (M+H).

Example 29

4-Methoxy-N-(4-piperazin-1-yl-naphthalen-1-yl)-benzenesulfonamide, hydrochloride $^1$H NMR (DMSO-d6) δ; 9.96 (s, 1H), 9.13 (brs, 1H), 8.15–8.08 (m, 1H), 8.06–7.99 (m, 1H), 7.65–7.57 (m, 2H), 7.55–7.42 (m, 2H), 7.12–6.97 (m, 4H), 3.43–3.29 (m, 4H), 3.24–3.10 (m, 4H), MS (posESI) m/z=398 (M+H).

Example 30

4-Chloro-N-(4-piperazin-1-yl-naphthalen-1-yl)-benzenesulfonamide, hydrochloride $^1$H NMR (DMSO-d6) δ; 10.25 (brs, 1H), 9.03 (brs, 1H), 8.16–8.09 (m, 1H), 8.00–7.94 (m, 1H), 7.71–7.41 (m, 6H), 7.13–7.01 (m, 2H), 3.40–3.26 (m, obscured in part by solvent signal), 3.24–3.08 (m, 4H), MS (posESI) m/z=402 (M+H).

Example 31

2-Chloro-N-(4-piperazin-1-yl-naphthalen-1-yl)-benzenesulfonamide, hydrochloride $^1$H NMR (CDCl$_3$) δ; 8.24–8.12 (m, 2H), 7.90–7.83 (m, 1H), 7.60–7.43 (m, 3H), 7.32–7.27 (m, obscured in part by solvent signal, 1H), 7.09 (s, 1H), 7.04 (d, J=8.44 Hz, 1H), 6.87–6.79 (m, 1H), 3.90–3.40 (m, 4H), 3.12–2.80 (m, 4H), MS (posESI) m/z=402 (M+H).

Example 32

N-(4-Piperazin-1-yl-naphthalen-1-yl)-4-trifluoromethyl-benzenesulfonamide, hydrochloride $^1$H NMR (DMSO-d6) δ; 10.40 (brs, 1H), 9.03 (brs, 1H), 8.12 (d, J=7.65 Hz, 1H), 7.95–7.83 (m, 5H), 7.55–7.39 (m, 2H), 7.13–7.02 (m, 2H), 3.40–3.30 (m, obscured inp art by solvent signal), 3.23–3.09 (m, 4H), MS (posESI) m/z=436 (M+H).

Example 33

4-Fluoro-N-(4-piperazin-1-yl-naphthalen-1-yl)-benzenesulfonamide, hydrochloride $^1$H NMR (DMSO-d6) δ; 10.17 (brs, 1H), 9.18 (brs, 2H), 8.15–8.08 (m, 1H), 7.99–7.92 (m, 1H), 7.77–7.66 (m, 2H), 7.55–7.30 (m, 4H), 7.11–7.01 (m, 2H), 3.40–3.30 (m, obscured by solvent signal,), 3.25–3.10 (m, 4H), MS (posESI) m/z=386 (M+H).

Example 34

5-Fluoro-2-methyl-N-(4-piperazin-1-yl-naphthalen-1-yl)-benzenesulfonamide, hydrochloride $^1$H NMR (DMSO-d6) δ; 10.27 (brs, 1H), 9.19 (brs, 2H), 8.16–8.10 (m, 1H), 8.03–7.96 (m, 1H), 7.58–7.33 (m, 5H), 7.12–6.98 (m, 2H), 3.40–3.30 (m, obscured by solvent signal) 3.24–3.10 (m, 4H), MS (posESI) m/z=400 (M+H).

Example 35

4-Phenoxy-N-(4-piperazin-1-yl-naphthalen-1-yl)-benzenesulfonamide, hydrochloride $^1$H NMR (DMSO-d6) δ; 10.08 (s, 1H), 9.11 (brs, 2H), 8.18–8.07 (m, 1H), 7.98–7.89 (m, 1H), 7.67–7.60 (m, 2H), 7.57–7.40 (m, 4H), 7.28–7.20 (m, 1H), 7.11 (s, 2H), 7.07–6.98 (m, 1H), 7.11 (s, 2H), 7.07–6.98 (m, 4H), 3.40–3.30 (m, obscured by solvent signal), 3.24–3.10 (m, 4H), MS (posESI) m/z=460 (M+H).

Example 36

2-Bromo-4-iodo-N-(4-piperazin-1-yl-naphthalen-1-yl)-benzenesulfonamide, hydrochloride $^1$H NMR (DMSO-d6) δ; 10.45 (brs, 1H), 9.01 (brs, 2H), 8.28 (d, J=1.58 Hz, 1H), 8.18–8.09 (m, 2H), 7.88–7.83 (m, 1H), 7.59–7.50 (m, 3H), 7.07 (s, 2H), 3.40–3.30 (m, obscured by solvent signal), 3.23–3.10 (m, 4H), MS (posESI) m/z=572 (M+H).

Example 37

Thiophene-2-sulfonic acid (4-piperazin-1-yl-naphthalen-1-yl)-amide, hydrochloride $^1$H NMR (DMSO-d6) δ; 10.30 (s, 1H), 9.12 (brs, 1H), 8.17–8.09 (m, 1H), 8.00–7.92 (m, 1H), 7.89–7.85 (m, 1H), 7.56–7.38 (m, 3H), 7.18–7.06 (m, 3H), 3.40–3.30 (m, obscured by solvent signal), 3.25–3.15 (m, 4H), MS (posESI) m/z=374 (M+H).

Example 38

5-Chloro-thiophene-2-sulfonic acid (4-piperazin-1-yl-naphthalen-1-yl)-amide, hydrochloride $^1$H NMR(DMSO-d6) δ; 10.43 (brs, 1H), 9.11 (brs, 2H), 8.19–8.111 (m, 1H), 8.02–7.95 (m, 2H), 7.29 (d, J=3.95 Hz, 1H), 7.21–7.12 (m, 3H), 3.40–3.30 (m, obscured by solvent signal), 3.25–3.15 (m, 4H), MS (posESI) m/z=408 (M+H).

Example 39

3-Methyl-N-(4-piperazin-1-yl-naphthalen-1-yl)-benzenesulfonamide, hydrochloride $^1$H NMR (DMSO-d6) δ; 8.14–8.07 (m, 1H), 8.04–7.97 (m, 1H), 7.55–7.35 (m, 6H), 7.07–6.97 (m, 2H), 3.30–2.98 (m, obscured in part by solvent signal, 8H), 2.29 (s, 3H), MS (posESI) m/z=442 (M+H).

Example 40

4-Butyl-N-(4-piperazin-1-yl-naphthalen-1-yl)-benzenesulfonamide hydrochloride:

$^1$H NMR (DMSO-d6) δ; 10.05 (s, 1H), 9.20 (brs, 2H), 8.11 (d, J=7.91 Hz, 1H), 7.93 (d, J=8.18 Hz, 1H), 7.62–7.26 (m, 5H), 7.07 (s, 2H), 3.40–3.30 (m, obscured by solvent signal), 3.25–3.15 (m, 4H), 2.66–2.55 (m, obscured in part by solvent signal, 2H), 1.58–1.15 (m, 2H), 1.32–1.15 (m, 2H), 0.92–0.83 (m, 3H), MS (posESI) m/z=427 (M+H).

Example 41

2,4,6-Trimethyl-N-(4-piperazin-1-yl-naphthalen-1-yl)-benzenesulfonamide, hydrochloride $^1$H NMR (DMSO-d6) δ; 9.92 (brs, 1H), 9.01 (brs, 2H), 8.15–8.09 (m, 1H), 8.05–7.98 (m, 1H), 7.55–7.42 (m, 2H), 7.09–6.94 (m, 4H), 3.40–3.30 (m, obscured by solvent signal), 3.25–3.15 (m, 4H) 2.85 (s, 6H), 2.22 (s, 3H), MS (posESI) m/z=410 (M+H).

Example 42

2,4,5-Trichloro-N-(4-piperazin-1-yl-naphthalen-1-yl)-benzenesulfonamide, hydrochloride $^1$H NMR (DMSO-d6) δ; 10.68 (brs, 1H), 9.06 (brs, 1H), 8.22–8.08 (m, 2H), 8.18 (s, 1H), 7.88 (s, 1H), 7.61–7.52 (m, 2H), 7.09 (s, 2H), 3.40–3.30 (m, obscured by solvent signal), 3.25–3.15 (m, 4H), MS (posESI) m/z=470 (M+H).

Example 43

4-Iodo-N-(4-piperazin-1-yl-naphthalen-1-yl)-benzenesulfonamide, hydrochloride $^1$H NMR (DMSO-d6) δ; 10.22 (s, 1H), 9.06 (brs, 2H), 8.16–8.09 (m, 1H), 8.02–7.87 (m, 3H), 7.58–7.39 (m, 4H), 7.18–6.98 (m, 2H), 3.40–3.30 (m, 4H), 3.25–3.10 (m, 4H), MS (posESI) m/z=494 (M+H).

Example 44

2-Methyl-N-(4-piperazin-1-yl-naphthalen-1-yl)-benzenesulfonamide, hydrochloride:

$^1$H NMR (DMSO-d6) δ; 10.13 (s, 1H), 9.15 (brs, 2H), 8.15–8.08 (m, 1H), 8.07–7.63 (m, 1H), 7.70–7.63 (m, 1H), 7.61–7.23 (m, 2H), 3.41–3.27 (m, 4H), 3.24–3.09 (m, 4H), 2.55 (s, obscured in part by solvent signal, 3H), MS (posESI) m/z=382 (M+H).

Example 45

3,4-Dichloro-N-(4-piperazin-1-yl-naphthalen-1-yl)-benzenesulfonamide, hydrochloride MS (posESI) m/z=436 (M+H)

Example 46

5-Bromo-2-methoxy-N-(4-piperazin-1-yl-naphthalen-1-yl)-benzenesulfonamide, hydrochloride $^1$H NMR (DMSO-d6) δ; 10.13 (s, 1H), 9.10 (brs, 2H), 8.16–8.07 (m, 2H), 7.78–7.71 (m, 1H), 7.59 (d, J=2.64 Hz, 1H), 7.57–7.46 (m, 2H), 7.22–7.06 (m, 3H), 3.19 (s, 3H), 3.40–3.30 (m, obscured by solvent signal), 3.24–3.09 (m, 4H), MS (posESI) m/z=476 (M+H).

Example 47

2-Bromo-N-(4-piperazin-1-yl-naphthalen-1-yl)-benzenesulfonamide, hydrochloride $^1$H NMR (DMSO-d6) δ; 9.37 (brs, 1H), 8.22–8.07 (m, 2H), 7.89–7.79 (m, 2H), 7.57–7.40 (m, 4H), 7.05 (s, 2H), 3.40–3.30 (m, obscured by solvent signal), 3.24–3.09 (m, 4H), MS (posESI) m/z=446 (M+H).

Example 48

3-Chloro-2-methyl-N-(4-piperazin-1-yl-naphthalen-1-yl)-benzenesulfonamide, hydrochloride $^1$H NMR (DMSO-d6) δ; 9.11 (brs, 1H), 8.17–8.09 (m, 1H),), 8.04–7.96 (m, 1H), 7.73–7.67 (m, 2H), 7.58–7.46 (m, 2H), 7.36–7.27 (m, 1H), 7.11–6.99 (m, 2H), 3.40–3.30 (m, obscured by solvent signal), 3.24–3.09 (m, 4H), 2.57 (s, 3H), MS (posESI) m/z=416 (M+H).

Example 49

2,6-Dichloro-N-(4-piperazin-1-yl-naphthalen-1-yl)-benzenesulfonamide, hydrochloride $^1$H NMR (DMSO-d6) δ; 10.60 (s, 1H), 9.08 (brs, 1H), 8.18–8.06 (m, 2H), 7.66–7.44 (m, 5 H), 7.09 (s, 2H), 3.40–3.30 (m, obscured by solvent signal), 3.24–3.09 (m, 4H), MS (posESI) m/z=436 (M+H).

Example 50

3-Methoxy-N-(4-piperazin-1-yl-naphthalen-1-yl)-benzenesulfonamide, hydrochloride $^1$H NMR (DMSO-d6) δ; 10.13 (s, 1H), 9.07 (brs, 2H), 8.15–8.08 (m, 1H), 8.02–7.95 (m, 1H), 7.56–7.36 (m, 3H), 7.28–7.22 (m, 1H), 7.19–7.02 (m, 4H), 3.69 (s, 3H), 3.40–3.30 (m, 4H), 3.24–3.10 (m, 4H), MS (posESI) m/z=398 (M+H).

Example 51

3-Chloro-4-methyl-N-(4-piperazin-1-yl-naphthalen-1-yl)-benzenesulfonamide, hydrochloride $^1$H NMR (DMSO-d6) δ; 10.20 (brs, 1H), 9.12 (brs, 2H), 8.16–8.10 (m, 1H), 8.04–7.97 (m, 1H), 7.65–7.61 (m, 1H), 7.58–7.43 (m, 4H), 7.12–6.99 (m, 2H), 3.40–3.30 (m, obscured by solvent signal), 3.24–3.09 (m, 4H), 2.36 (s, 3H), MS (posESI) m/z=416 (M+H).

Example 52

4-Bromo-2-fluoro-N-(4-piperazin-1-yl-naphthalen-1-yl)-benzenesulfonamide, hydrochloride $^1$H NMR (DMSO-d6) δ; 10.59 (s, 1H), 9.17 (brs, 2H), 8.17–8.09 (m, 1H), 8.08–7.99 (m, 1H), 7.87–7.80 (m, 1H), 7.59–7.46 (m, 4H), 7.16–7.07 (m, 2H), 3.42–3.28 (, 4H), 3.24–3.08 (m, 4H), MS (posESI) m/z=464 (M+H).

Example 53

2,4-Dichloro-6-methyl-N-(4-piperazin-1-yl-naphthalen-1-yl)-benzenesulfonamide, hydrochloride $^1$H NMR (DMSO-d6) δ; 9.08 (brs, 2H), 8.18–8.04 (m, 2H), 7.73–7.69 (m, 1H), 7.60–7.42 (m, 3H), 7.14–7.04 (m, 2H), 3.40–3.30 (m, obscured by solvent signal), 3.24–3.09 (m, 4H), 2.80 (s, 3H), MS (posESI) m/z=450 (M+H).

Example 54

4-Bromo-2-methyl-N-(4-piperazin-1-yl-naphthalen-1-yl)-benzenesulfonamide, hydrochloride $^1$H NMR (DMSO-d6) δ; 10.24 (brs, 1H), 9.12 (brs, 2H), 8.17–8.10 (m, 1H), 8.05–7.98 (m, 1H), 7.68–7.65 (m, 1H), 7.58–7.46 (m, 4H), 7.10–6.96 (m, 2H), 3.40–3.30 (m, obscured by solvent signal), 3.24–3.09 (m, 4H), 2.53 (s, obscured in part by solvent signal, 3H), MS (posESI) m/z=450 (M+H).

Example 55

4,5-Dichloro-thiophene-2-sulfonic acid (4-piperazin-1-yl-naphthalen-1-yl)-amide, hydrochloride $^1$H NMR (DMSO-d6) δ; 8.97 (brs, 2H), 8.19–8.12 (m, 1H), 8.01–7.94 (m, 1H), 7.60–7.47 (m, 2h), 7.50 (S, 1H), 7.25–7.14 (m, 2H), 3.40–3.30 (m, obscured by solvent signal), 3.24–3.09 (m, 4H), MS (posESI) m/z=442 (M+H).

Example 56

N-Methyl-N-(4-bromo-2-methylphenyl)-4-(1-pyperazinyl)-1-napthalenesulphonamide, hydrochloride $^1$H NMR (DMSO) δ 9.39 (br s, 2H), 8.23–8.13 (m, 1H), 8.09–7.99 (m, 1H), 7.75–7.56 (m, 5H), 7.13–7.02 (m, 2H), 3.41–3.18 (m, 8H), 3.26 (s, 3H), 2.25 (s, 3H); MS m/z (M+1) 475.

Example 57

N-Methyl-N-(5-fluoro-2-methylphenyl)-4-(1-pyperazinyl)-1-napthalenesulphonamide, hydrochloride $^1$H NMR (DMSO) δ 9.21 (br s, 2H), 8.23–8.14 (m, 1H), 8.04–7.97 (m, 1H), 7.64–7.45 (m, 5H), 7.13–7.03 (m, 2H), 3.43–3.17 (m, 8H), 3.29 (s, 3H), 2.21 (s, 3H); MS m/z (M+1) 414.

Example 58

N-Methyl-N-(2-methylphenyl)-4-(1-pyperazinyl)-1-napthalenesulphonamide, hydrochloride $^1$H NMR (CD$_3$OD) δ 8.26–8.19 (m, 1H), 8.11–8.05 (m, 1H), 7.87–7.81 (m, 1H), 7.62–7.49 (m, 3H), 7.40–7.32 (m, 2H), 7.13–7.03 (m, 2H), 3.57–3.49 (m, 4H), 3.34–3.30 (m, 7H), 2.30 (s, 3H); MS m/z (M+1) 396.

Example 59

N-Methyl-N-(3-chloro-2-methylphenyl)-4-(1-pyperazinyl)-1-napthalenesulphonamide, hydrochloride $^1$H NMR (DMSO) δ 9.52 (br s, 2H), 8.23–8.14 (m, 1H), 8.04–7.96 (m, 1H), 7.88–7.76 (m, 2H), 7.64–7.54 (m, 2H), 7.49–7.39 (m, 1H), 7.17–7.05 (m, 2H), 3.42–3.16 (m, 8H), 3.27 (s, 3H), 2.34 (s, 3H); MS m/z (M+1) 430.

Example 60

2,5-Dichlorothiophen-3-yl-Methyl-N-(2,5-dichlorothiophen-3-yl)-4-(1-pyperazinyl)-1-napthalenesulphonamide, hydrochloride $^1$H NMR (DMSO) δ 9.49 (br s, 1H), 8.24–8.13 (m, 1H), 8.07–7.98 (m, 1H), 7.67–7.55 (m, 2H), 7.33 (s, 1H), 7.24–7.07 (m, 2H), 3.44–3.18 (m, 10H); MS m/z (M+1) 456.

Example 61

N-Methyl-N-(1-naphthyl)-4-(1-pyperazinyl)-1-napthalenesulphonamide, hydrochloride The compound was prepared 1-tert-butyl-4-(4-{bis[(2-naphthalene)sulfonyl]amino}-1-naphthyl)-1-piperazinecarboxylate and potassium carbonate (120 mg, 0.87 mmol) in acetone (2 ml) was added iodomethane (44 μl, 0.7 mmol) and the mixture was stirred at room temperature over night. The mixture was diluted with acetonitrile, filtered and concentrated in vacuo. The residue was redissolved in DCM (3 ml) and treated with concentrated TFA (1 ml) at 0° C. for 30 min and then allowed to reach room temperature. Removal of the solvents in vacuo and purification by reversed phase HPLC.followed by treatment of the residue with an excess of 1M HCl in diethyl ether, gave the title compound (70 mg, 58%) as a solid. $^1$H NMR (DMSO)δ 9.28 (br s, 2H), 8.44 (s, 1H), 8.24–8.07 (m, 5H), 7.80–7.56 (m, 5H), 7.07–7.00 (m, 1H), 6.88–6.81 (m, 1H), 3.41–3.18 (m, 8H), 3.27 (s, 3H); MS m/z (M+1) 432.

Example 62

N-Methyl-N-(1-naphthyl)-4-(1-pyperazinyl)-1-napthalenesulphonamide, hydrochloride $^1$H NMR (DMSO) δ 9.25 (br s, 2H), 8.37–8.28 (m, 2H), 8.22–8.08 (m, 3H), 8.02–7.95 (m, 1H), 7.72–7.46 (m, 5H), 6.97 (s, 2H), 3.42–3.33 (m, 4H), 3.25 (s, 3H), 3.24–3.16 (m, 3H); MS m/z (M+1) 432.

Example 63

N-Methyl-N-(4-chlorophenyl)-4-(1-pyperazinyl)-1-napthalenesulphonamide, hydrochloride $^1$H NMR (DMSO) δ 9.41 (br s, 2H), 8.23–8.05 (m, 2H), 7.73 (s, 4H), 7.67–7.56 (m, 2H), 7.13–7.03 (m, 1H), 6.92–6.85 (m, 1H), 3.42–3.19 (m, 8H), 3.22 (s, 3H); MS m/z (M+1) 416.

Example 64

N-Methyl-N-(4-methoxyphenyl)-4-(1-pyperazinyl)-1-napthalenesulphonamide, hydrochloride $^1$H NMR (DMSO) δ 9.45 (br s, 2H), 8.22–8.11 (m, 2H), 7.69–7.57 (m, 4H), 7.21–7.14 (m, 2H), 7.09–7.03 (m, 1H), 6.86–6.81 (m, 1H), 3.87 (s, 3H), 3.41–3.19 (m, 8H), 3.16 (s, 3H); MS m/z (M+1) 412.

Example 65

5-Fluoro-2-methyl-N-{4-[(2R,5S)-2,5-dimethyl-1-]piperazin-1-yl-1-naphthyl}benzenesulfonamide, hydrochloride Synthesis of (2R,5S)-2,5-Dimethyl-1-(4-nitro-1-naphthyl)piperazine—A mixture of 1-chloro-4-nitronaphtalene (400 mg, 1.9 mmol), (2R,5S)-2,5-dimethylpiperazine (800 mg, 7 mmol) and potassium carbonate (1 g, 7 mmol) in DMSO (4 ml) was stirred at 100° C. over night followed by an additional 48 hours at room temperature. The reaction mixture was diluted with ethyl acetate and filtered. The filtrate was washed with brine and 2M NaOH solution and then dried with potassium carbonate. The residue was purified on a silica column, using 10% methanol in chloroform as an eluent, to give the title compound (220 mg, 41%) as an oil. $^1$H NMR (CDCl$_3$) δ 8.68–8.53 (m, 2H), 8.31–8.26 (m, 1H), 7.76–7.59 (m, 2H), 7.30–7.24 (m, 1H), 3.32–3.87 (m, 4H), 2.96–2.82 (m, 1H), 2.44–2.32 (m, 1H), 1.14–1.04 (m, 3H), 0.99–0.89 (m, 3H); MS m/z (M+1) 286.

Synthesis of tert-Butyl (2R,5S)-2,5-dimethyl-1-(4-nitro-1-naphthyl)piperazine-1-carboxylate—To a stirred solution of (2R,5S)-2,5-Dimethyl-1-(4-nitro-1-naphthyl)piperazine (220 mg, 0.77 mmol) in DCM (2 ml) was added, at 0° C., BOC-anhydride dissolved in DCM (2 ml). The solution was stirred for 15 min and was then allowed to reach room temperature. Water was added and the solution was extracted with DCM. The organic phase was separated and dried with potassium carbonate to give the title compound (300 mg, 100%) as an oil. $^1$H NMR (CDCl$_3$) δ 8.75–8.67 (m, 1H), 8.30–8.17 (m, 2H), 7.70–7.55 (m, 2H), 6.93–6.86 (m, 1H), 4.60–4.50 (m, 1H), 3.97–3.65 (m, 4H), 2.90–2.73 (m, 1H), 1.49 (s, 9H), 1.41–1.36 (m, 3H), 0.99–0.87 (m, 3H); MS m/z (M+1) 386.

Synthesis of 5-Fluoro-2-methyl-N-{4-[(2R,5S)-2,5-dimethyl-1-]piperazin-1-yl-1-naphthyl}benzenesulfonamide hydrochloride salt—A mixture of tert-butyl (2R,5S)-2,5-dimethyl-1-(4-nitro-1-naphthyl)piperazine-1-carboxylate (300 mg, 0.78 mmol) and 10% Pd on carbon (approx. 0.1 mmol) in methanol (10 ml) was stirred in an hydrogen atmosphere over night. The mixture was filtered through a pad of Celite and the solvent evaporated. The crude aniline was dissolved in DCM (2 ml) and pyridine (0.5 ml) and 5-fluoro-2-methylbenzenesulfonyl chloride (97 µl, 0.67 mmol) was added slowly to the solution. After stirring for 2 hours water was added and the solution was extracted with DCM, the organic phase separated and dried using potassium carbonate. Removal of the solvents in vacuo gave a residue which was dissolved in DCM (3 ml) and treated with concentrated TFA (2 ml) at 0° C. The stirred solution was allowed to reach room temperature after which the solvents where removed in vacuo to give, after purification by reversed phase HPLC and treatment with an excess of 1M HCl in diethyl ether, the title compound (30 mg, 9%) as a solid. $^1$H NMR (CD$_3$OD) δ 0.85 (d, J=6.07 Hz, 3 H) 1.31 (d, J=6.60 Hz, 3 H) 2.47 (s, 3 H) 2.83 (m, 1 H) 3.15 (m, 2 H) 3.49 (m, 2 H) 3.67 (m, 1 H) 7.21 (m, 4 H) 7.47 (m, 3 H) 7.97 (m, J=7.92 Hz, 1 H) 8.44 (d, J=8.44 Hz, 1 H) MS m/z 428 (M+1).

Example 66

5-Fluoro-2-methyl-N-[4-(1,2,3,6-tetrahydropyridin-4-yl)-1 naphthyl]benzenesulfonamide, hydrochloride 5-Fluoro-2-methyl-N-[4-bromo-1-naphthyl]benzenesulfonamide—4-Bromo-1-naphthylamine (0.96 g, 4.33 mmol) was dissolved in DCM (10 mL) before pyridine (1 mL) was added. 5-Fluoro-2-methylbenzenesulfonyl chloride was added neat and the reaction mixture was stirred for 16 h. HCl (1 M, 1 mL) was added to the reaction mixture. The organic phase was filtered through a Silica plug using DCM as eluent. The solvent was evaporated. The obtained crude product was purified by flash-chromatography using MeOH (10%) in pentane, to give the desired product as a tar. To increase the purity, the product was purified by recrystallising (EtOAc/hexanes). This gave the product with a purity of 95%. $^1$H NMR (270 MHz, CDCl$_3$) δ 8.22 (d, J=8.98 Hz, 1H), 7.92 (d, J=7.92 Hz, 1H), 7.64–7.51 (m, 4H), 7.25–7.23 (m, 1H), 7.21–7.05 (m, 2H), 6.84 (br.s, 1H, N—H), 2.55 (s, 3H); MS (ESI+) for C17 H13 Br F N O2 S m/z 394.263 (M+H)$^+$. MS (ESI−) for C17 H13 Br F N O2 S m/z 394.263 m/z (M−H)$^-$.

5-Fluoro-2-methyl-N-[4-(4-(tert-butoxycarbonyl)-1-hydroxypiperidin-1-yl)-1-naphthyl]benzenesulfonamide—5-Fluoro-2-methyl-N-[4-bromo-1-naphthyl]benzenesulfonamide (0.32 g, 0.812 mmol) was dissolved in dry THF (1 m mL) under N$_2$(g). The reaction flask was cooled to −78° C. before n-BuLi (1.5 mL, 2.4 mmol) was added. The reaction mixture turned green. The reaction mixture was stirred for 5 minutes before a solution of tert-butyl 4-oxopiperidine-1-carboxylate (0.34 g, 1.7 mmol) was added during 10 s. The resulting reaction mixture was stirred and slowly reaching −30° C. after 3 h. Water dissolved in THF was added and the reaction flask was brought to RT. Brine and EtOAc was added. The phases were separated and the organic phase was dried (MgSO4).

The obtained crude product was purified by reverse-phase (using the gradient 40→90). This gave 0.17 g of the desired product. Purity 95%. $^1$H NMR (270 MHz, CDCl$_3$) δ 8.91–8.87 (m, 1H), 7.97–7.93 (m, 1H), 7.63–7.59 (m, 1H), 7.53–7.45 (m, 2H), 7.35 (d, J=8.1 Hz, 1H), 7.28–7.21 (m, 1H), 7.16–7.09 (m, 2H), 7.14 (br.s, 1H, N—H), 6.85 (br.s, 1H, O—H), 4.07–3.98 (m, 2H), 3.41–3.31 (m, 2H), 2.59 (s, 3H), 2.17–2.08 (m, 4H), 1.46 (s, 9H); MS (ESI+) for C27H31 F N2 O5 S m/z 514.615 (M+H)$^+$. Nothing; MS (ESI−) for C27 H31 F N2 O5 S m/z 514.615 (M−H)$^-$ 513.1.

The final product was obtained as following: 5-Fluoro-2-methyl-N-[4-(4-(tert-butoxycarbonyl)-1-hydroxypiperidin-1-yl)-1-naphthyl]benzenesulfonamide (0.022 g, 0.043 mmol) was dissolved in formic acid (5 mL) and stirred at RT for 24 h. HPLC showed complex reaction mixture. The reaction mixture was stirred at 100° C. for 4 h. One compound was seen on HPLC. The solvent was evaporated. The crude was transformed to the HCl salt (0.020 g) for the desired product, purity 98%. $^1$H NMR (270 MHz, CD$_3$OD) δ 8.05–7.97 (m, 2H), 7.55–7.43 (m, 3H), 7.33–7.30 (m, 1H), 7.24–7.17 (m, 3H), 5.97 (br.s, 1H), 3.90–3.88 (m, 2H), 3.56–3.52 (m, 2H), 2.73–2.70 (m, 2H), 2.53 (s, 3H); MS (ESI+) for C22 H21 F N2 O2 S HCl m/z 396.13+35.98 (M+H)$^+$397.2; MS (ESI−) C22 H21 F N2 O2 S HCl m/z 396.13+35.98 (M−H)$^-$. 395.3.

Synthesis of Example in Table II

Example 67

N-[4-(4-Methyl-1-piperazinyl)-2-naphthyl]benzenesulfonamide, hydrochloride

To a solution of 1-(4-dimethyl-1-piperazinyl)-3-naphthylamine (0.230 g, 0.951 mmol) and pyridine (537 µL, 6.66 mmol) in DCM (3.0 mL) was added benzenesulfonyl chloride (0.168 g, 0.951 mmol) in DCM (1.0 mL). The reaction mixture was stirred at room temperature for 16 hours and then and then concentrated. The crude intermediate was first purified via column chromatography on silica using CHCl$_3$/CHCl$_3$+10% MeOH+0.4% NH$_3$ and then by preparative HPLC to give the pure base which was converted to its HCl-salt (yield 53% as HCl-salt): 1H NMR (DMSO-d6) δ 10.76 (br s, 1H), 10.50 (s, 1H), 7.98–7.94 (m, 1H), 7.85–7.81 (m, 2H), 7.76–7.73 (m, 1H), 7.60–7.56 (m, 1H), 7.55–7.51 (m, 2H), 7.30 (d, J=1.60 Hz, 1H), 6.99 (d, J=1.88 Hz, 1H), 3.58–3.48 (m, 2H), 3.42–3.25 (m, m, partly obscured by HDO signal, 4H), 3.12–3.00 (m, 2H), 2.86 (s, 3H); MS (posES-FIA) m/z=381.15 24 (M+H)(calc 381.1511)

Synthesis of Intermediates and Examples in Table III

Scheme 2

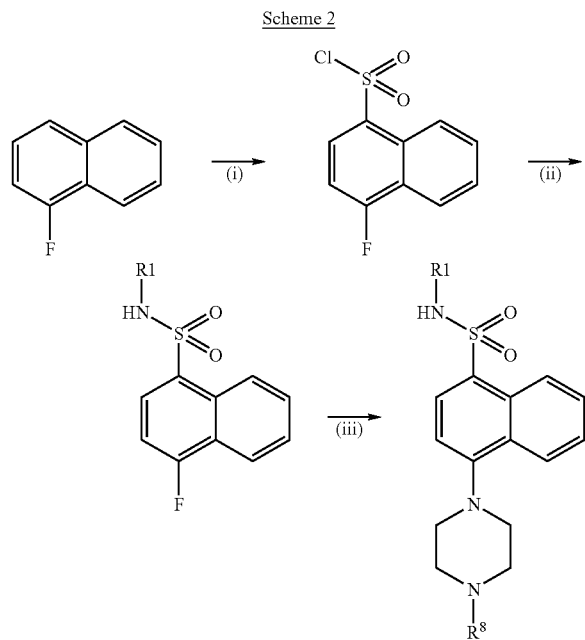

In scheme 2, the following reagents are used: (i) Chlorosulphonic acid, trifluoroacetic acid; (ii) R$^1$—NH$_2$, pyridine (1:4); (iii) diamines of choice and DMSO.

Intermediate 16

4-Fluoro-naphthalene-1-sulfonyl chloride—An emulsion of 1-fluoronaphthalene (4.00 g, 27 mmol) in TFA (19.5 mL) was stirred on an ice-bath. Chlorosulfonic acid (4.33 mL, 65 mmol) was added dropwise over 30 min. The ice-bath was removed and the reaction slurry stirred at rt for 2 h. Pouring the reaction mixture on 29 mL ice-cold water gave a white precipitate, which was filtered and washed with cold water. After drying, 4.50 g of white solid (67%): $^1$H NMR (CDCl$_3$, 400 MHz) δ 8.80 (d, 1H), 8.39 (dd, 1H), 8.28 (d, 1H), 7.88 (t, 1H), 7.76 (t, 1H), 7.26 (t, 1H); MS (EI) 244 (M). Purity (HPLC, Hichrom 200×4.6 mm I.D.) >98%.

General Method C

4-Fluoro-naphthalene-1-sulfonic acid phenylamide, 4fluoro-naphthalene-1-sulfonic acid (2-methoxy-phenyl)-amide and 4-fluoro-naphthalene-1-sulfonic acid (3-chloro-phenyl)-amide—Three reaction flasks with 4-fluoro-naphthalene-1-sulfonyl chloride (489 mg, 2.00 mmol) in CH$_2$Cl$_2$ (2 mL) were treated with aniline (224 mg, 2.40 mmol), o-anisidine (296 mg, 2.40 mmol) and m-chloroaniline (306 mg, 2.40 mmol), respectively. Pyridine (0.5 mL) was added and the reaction mixtures stirred for 3 h at rt. Dilution with ethyl acetate (50 mL) followed by washing with 1 M HCl (3×50 mL), drying (Na$_2$SO$_4$) and evaporation gave 586 mg of 4-fluoro-naphthalene-1-sulfonic acid phenylamide (97%), 629 mg of 4-fluoro-naphthalene-1-sulfonic acid (2-methoxy-phenyl)-amide (95%) and 656 mg of and 4-fluoro-naphthalene-1-sulfonic acid (3-chloro-phenyl)-amide (97%) as pink to red solids.

Intermediate 17

4-Fluoro-naphthalene-1-sulfonic acid phenylamide: $^1$H NMR (CDCl$_3$, 400 MHz) δ 8.66 (d, 1H), 8.20 (d, 1H), 8.15 (dd, 1H), 7.74 (t, 1H), 7.66 (t, 1H), 7.03–7.15 (m, 4H), 6.89 (d, 2H), 6.60 (bs, 1H); MS (CI) 299.8 (M–H)$^+$; Purity (HPLC, Hichrom 200×4.6 mm I.D.) >98%.

Intermediate 18

4-Fluoro-naphthalene-1-sulfonic acid (2-methoxy-phenyl)-amide: $^1$H NMR (CDCl$_3$, 400 MHz) δ 8.70 (d, 1H), 8.16 (d, 1H), 8.12 (dd, 1H), 7.71 (t, 1H), 7.63 (t, 1H), 7.42 (d, 1H), 7.16 (bs, H), 7.06 (t, 1H), 6.95 (t, 1H), 6.83 (t, 1H), 6.56 (d, 1H), 3.30 (s, 3H); MS (CI) 330.2 (M–H)$^+$; Purity (HPLC, Hichrom 200×4.6 mm I.D.)>98%.

Intermediate 19

4-Fluoro-naphthalene-1-sulfonic acid (3-chloro-phenyl)-amide: $^1$H NMR (CDCl$_3$, 400 MHz) δ 8.64 (d, 1H), 8.18–8.22 (m, 2H), 7.76 (t, 1H), 7.68 (t, 1H), 7.14 (dd, 1H), 7.06 (t, 1H), 7.02 (d, 1H), 6.97 (t, 1H), 6.78 (d, 1H), 6.67 (bs, 1H); MS (CI) 334.2 (M–H)$^+$; Purity (HPLC, Hichrom 200×4.6 mm I.D.) >98%.

General Procedure D

General Procedure for Preparation of Compounds According to Examples 68–74:

Solutions of 4-fluoro-naphthalene-1-sulfonic acid (2-methoxy-phenyl)-amide (60 mg, 0.20 mmol), 4-fluoro-naphthalene-1-sulfonic acid (2-methoxy-phenyl)-amide (66 mg, 0.20 mmol) and 4-fluoro-naphthalene-1-sulfonic acid (3-chloro-phenyl)-amide (67 mg, 0.20 mmol) in DMSO (2 mL) were treated with piperazine (86 mg, 1.0 mmol), homopiperazine (100 mg, 1.0 mmol) and cis-2,6-dimethyl piperazine (114 mg, 1.0 mmol) in eight reaction combinations. The reaction mixtures were stirred at 100° C. for 3 h, diluted with ethyl acetate (50 mL), washed with sat. Na$_2$CO$_3$ (3×50 mL), dried (Na$_2$SO$_4$) and evaporated with an excess of HCl in ether, giving the hydrochlorides. No purification was necessary for compounds 20–23, while compounds 24–27 were purified with HPLC (YMC combiprep ODS-AQ, 50×20 mm I.D.).

Example 68

4-Piperazin-1-yl-naphthalene-1-sulfonic acid phenylamide, hydrochloride 86 mg (95% yield) of a white solid. $^1$H NMR (DMSO, 400 MHz) δ 9.52 (bs, 1H), 8.72 (d, 1H), 8.20 (d, 1H), 8.15 (d, 1H), 7.71 (t, 1H), 7.64 (t, 1H), 7.20 (d, 1H), 7.13 (t, 2H), 7.01 (d, 2H), 6.90 (t, 1H), 3.35 (bs, 4H), 3.30 (bs, 4H). $^{13}$C NMR (DMSO, 101 MHz) δ 153.3, 137.7, 137.6, 130.8, 129.2, 129.0, 128.9, 127.9, 126.5, 124.9, 124.5, 123.3, 118.7, 113.0, 49.1, 42.8; MS (CI) 368.0 (M+H)$^+$, 366.4 (M–H)$^-$; Purity (HPLC, Hichrom 200×4.6 mm I.D.) 90%.

Example 69

4-Piperazin-1-yl-naphthalene-1-sulfonic acid (2-methoxy-phenyl)-amide, hydrochloride

$^1$H NMR (DMSO, 400 MHz) δ 9.59 (s, 1H), 8.76 (d, 1H), 8.23 (d, 1H), 7.93 (d, 1H), 7.64–7.70 (m, 2H), 7.14–7.19 (m, 2H), 7.05 (t, 1H), 6.82 (t, 1H), 6.76 (d, 1H), 3.39 (bs, 4H), 3.29 (bs, 4H), 3.11 (s, 3H). $^{13}$C NMR (DMSO, 101 MHz) δ 152.9, 152.5, 130.6, 129.7, 129.3, 127.9, 127.3, 126.5, 126.3, 125.7, 125.3, 125.2, 124.1, 120.2, 112.8, 111.6, 54.9, 49.2, 43.0. MS (CI) 398.2 (M+H)$^+$, 396.2 (M−H)$^-$; Purity (HPLC, Hichrom 200×4.6 mm I.D.) 96%.

Example 70

4-(cis-3,5-Dimethyl-piperazin-1-yl)-naphthalene-1-sulfonic acid (2-methoxy-phenyl)-amide, hydrochloride

$^1$H NMR (DMSO, 400 MHz) δ 9.75–9.81 (m, 1H), 9.60 (s, 1H), 9.03–9.12 (m, 1H), 8.76 (d, 1H), 8.23 (d, 1H), 7.93 (d, 1H), 7.64–7.71 (m, 2H), 7.05 (t, 1H), 6.82 (t, 1H), 6.76 (d, 1H), 3.63–3.71 (m, 2H), 3.47 (d, 2H), 3.13 (s, 3H), 2.89 (t, 2H), 1.32 (d, 6H). $^{13}$C NMR (DMSO, 101 MHz) δ 152.4, 152.3, 130.6, 129.8, 129.3, 127.9, 127.3, 126.5, 126.3, 125.3, 125.2, 125.1, 124.1, 120.2, 113.0, 111.6, 55.0, 54.9, 51.2, 15.5. MS (CI) 426.2 (M+H)$^+$, 424.4 (M−H)$^-$; Purity (HPLC, Hichrom 200×4.6 mm I.D.) 96%.

Example 71

4-(cis-3,5-Dimethyl-piperazin-1-yl)-naphthalene-1-sulfonic acid (3-chloro-phenyl)-amide, hydrochloride

$^1$H NMR (MeOD, 400 MHz) δ 8.80 (d, 1H), 8.32 (d, 1H), 8.27 (d, 1H), 7.79 (t, 1H), 7.73 (t, 1H), 7.28 (d, 1H), 7.12 (t, 1H), 7.07 (t, 1H), 6.95–7.00 (m, 2H); MS (CI) 430.2 (M+H)$^+$, 428.4 (M−H)$^-$; Purity (HPLC, Hichrom 200×4.6 mm I.D.) 98%.

Example 72

4-[1,4]Diazepan-1-yl-naphthalene-1-sulfonic acid (3-chloro-phenyl)-amide, hydrochloride

$^1$H NMR (MeOD, 400 MHz) δ 8.69 (d, 1H), 8.28 (d, 1H), 8.14 (d, 1H), 7.68 (t, 1H), 7.61 (t, 1H), 7.22 (d, 1H), 7.02 (t, 1H), 6.97 (bs, 1H), 6.86–6.89 (m, 2H), 3.57 (bs, 2H), 3.48 (bs, 4H), 3.33–3.37 (m, 2H), 2.20–2.24 (m, 2H); MS (CI) 416.0 (M+H)$^+$, 414.2 (M−H)$^-$; Purity (HPLC, Hichrom 200×4.6 mm I.D.) 88%.

Example 73

4-[1,4]Diazepan-1-yl-naphthalene-1-sulfonic acid Phenylamide, hydrochloride

$^1$H NMR (MeOD, 400 MHz) δ 8.57 (d, 1H), 8.13 (d, 1H), 7.96 (d, 1H), 7.44–7.55 (m, 2H), 7.04 (d, 1H), 6.90 (t, 2H), 6.72–6.82 (m, 3H), 3.39–3.43 (m, 2H), 3.32–3.36 (m, 4H), 3.17–3.21 (m, 2H), 2.05–2.10 (m, 2H); MS (CI) 382.2 (M+H)$^+$, 380.4 (M−H)$^-$; Purity (HPLC, Hichrom 200×4.6 mm I.D.) 94%.

Example 74

4-Piperazin-1-yl-naphthalene-1-sulfonic acid (3-chloro-phenyl)-amide, hydrochloride

$^1$H NMR (MeOD, 400 MHz) δ 8.69 (d, 1H), 8.23 (d, 1H), 8.16 (d, 1H), 7.68 (t, 1H), 7.62 (t, 1H), 7.17 (d, 1H), 7.02 (t, 1H), 6.97 (t, 1H), 6.85–6.89 (m, 2H), 3.46–3.50 (m, 4H), 3.33 (bs, 4H); MS (CI) 402.2 (M+H)$^+$, 400.0 (M−H)$^-$; Purity (HPLC, Hichrom 200×4.6 mm I.D.) 98%.

General method E

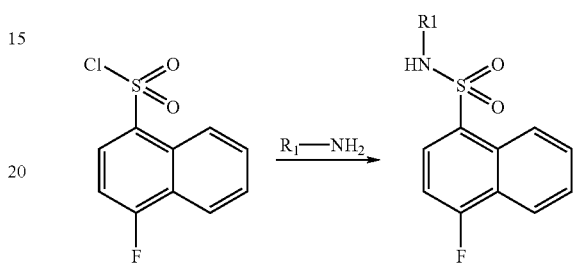

4-Fluoro-naphtalene-1-sulfonylchloride was dissolved in DCM. The amine (1.2eq) was added followed by pyridine (3eq). The mixture was stirred for 2 h at ambient temperature, diluted with DCM and washed 2 times with HCl (1M). The organic layer was filtered through a silica plug to afford the sulfonylamide.

General method F

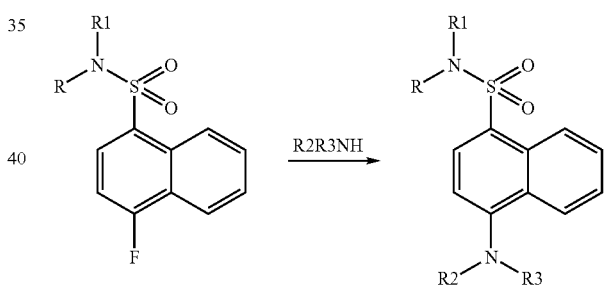

The sulfonamide and the amine (5 eq) were dissolved in DMSO and stirred at 100° C. overnight. The DMSO solution was added dropwise to water to give a precipitate. After centrifugation, the solvent was decanted and the procedure was repeated. The residue was dissolved in MeOH and converted to HCl salt by adding HCl in ether (2 M) and evaporation.

General method G

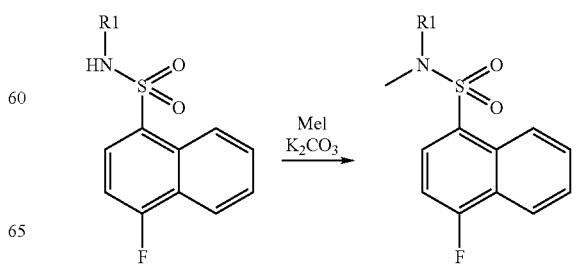

To a solution of the sulfonamide in acetone, K$_2$CO$_3$ (3 eq) was added followed by MeI (1.2 eq). The mixture was stirred overnight, filtered through a short silica plug and evaporated to give the methylated sulfonamide.

Example 75

4-Piperazin-1-yl-naphthalene-1-sulfonic acid (2-methylsulfanyl-phenyl)-amide, hydrochloride N-(2-methylsulfanyl-phenyl)-4-fluorosulphonamide—Method E; Yield (84%) $^1$H NMR (CDCl$_3$) δ 8.74–8.70 (m, 1 H), 8.29–8.24 (m, 1 H), 8.17–8.14 (m, 1 H), 8.01 (br. s, 1 H), 7.75–7.60 (m, 2 H), 7.50–7.47 (m, 1 H), 7.29–7.25 (m, 1 H), 7.18–7.10 (m, 2 H), 6.98–6.92 (m, 1 H), 2.02 (s, 3 H); MS (ESI+) for C17 H14 F N O2 S2 m/z 348 (M+H)$^+$.

The final product was prepared according to Method F; Yield 0.77 g (53%)

$^1$H NMR (DMSO-d$_6$) δ 11.13 (s, 1 H), 9.42 (br. s, 2 H), 8.69–8.66 (m, 1 H), 8.21–8.18 (m, 2 H), 7.76–7.62 (m, 2 H), 7.42–7.21 (m, 5 H), 3.421–3.30 (m, 8 H); MS (ESI+) for C21 H23 N3 O2 S2 m/z 414.2 (M+H)$^+$.

Example 76

4-Piperazin-1-yl-naphthalene-1-sulfonic acid methyl-naphthalen-1-yl-amide, hydrochloride N-(1-naphthyl)-4-fluoronaqphthalensulphonamide—Method E; Yield (83%)

$^1$H NMR (CDCl$_3$) δ 8.77–8.74 (m, 1 H), 8.18–8.05 (m, 2 H), 7.75–7.61 (m, 5 H), 7.41–7.35 (m, 1 H), 7.30–7.26 (m, 1 H), 7.14–7.00 (m, 2 H), 6.93 (br. s, 1 H); MS (ESI+) for C20 H14 F N O2 S m/z 352 (M+H)$^+$.

4-Fluoro-1-naphthalene-1-sulfonic acid methyl-naphthalen-1-yl-amide—Methylation according to Method G, Yield (97%)

$^1$H NMR (DMSO-d$_6$) δ 8.38–8.35 (m, 1 H), 8.23–8.20 (m, 1 H), 8.16 (dd, J=8.4, 5.5 Hz, 1 H), 7.99–7.91 (m, 3 H), 7.79–7.73 (m, 1 H), 7.66–7.46 (m, 4 H), 7.37–7.31 (m, 1 H), 7.03 (dd, J=7.5, 1.2 Hz, 1 H), 3.29 (s, 3 H)

The final product was prepared according to Method F; Yield (36%)

$^1$H NMR (DMSO-d$_6$) δ 9.33 (br. s, 1H), 8.40 (d, J=8.4 Hz, 1 H), 8.25 (d, J=7.9 Hz, 1 H), 8.09 (d, J=8.2 Hz, 1 H), 7.98–7.91 (m, 3 H), 7.68–7.62 (m, 1 H), 7.58–7.43 (m, 3 H), 7.40–7.34 (m, 1 H), 7.24 (d, J=8.2 Hz, 1 H), 7.13–7.10 (m, 1 H), 3.44–3.39 (m, 4 H), 3.29 (br. s, 4 H), 3.25 (s, 3 H); MS (ESI+) for C25 H25 N3 O2 S m/z 432 (M+H)$^+$.

Example 77

4-Piperazin-1-yl-naphthalene-1-sulfonic acid (2,3-dihydro-benzo[1,4]dioxin-6-yl)-methyl-amide, hydrochloride N-(2,3-dihydro-benzo[1,4]dioxin-6-yl)-4-sulphonamide—Method E; Yield (96%). $^1$H NMR (CDCl$_3$) δ 8.66–8.63 (m, 1 H), 8.22–8.09 (m, 2 H), 7.77–7.63 (m, 2 H), 7.10 (dd, J=8.2, 9.5 Hz, 1 H), 6.58 (d, J=8.5 Hz, 1 H), 6.46 (d, J=2.4 Hz, 1 H), 6.30 (dd, J=2.6, 8.7 Hz, 1 H), 4.14 (s, 4 H); MS (ESI+) for C18 H14 F N O4 S m/z 360 (M+H)$^+$.

4-Fluoro-Nl-naphthalene-1-sulfonic acid methyl-(2, 3-dihydro-benzo[1,4]dioxin-6-yl)-methyl-amide—Methylation according to Method G; Yield (100%). $^1$H NMR (DMSO-d$_6$) δ 8.19–8.13 (m, 2 H), 8.09 (dd, J=8.4, 5.5 Hz, 1 H), 7.75–7.70 (m, 1 H), 7.64–7.58 (m, 1 H), 7.50 (dd, J=10.0, 8.4 Hz, 1 H), 6.71 (d, J=8.4 Hz, 1 H), 6.55 (d, J=2.6 Hz, 1 H), 6.51–6.47 (m, 1 H), 4.20–4.15 (m, 4 H), 3.10 (s, 3 H)

The final product was prepared according to Method F; the product precipitates in MeOH; Yield (57%): $^1$H NMR (DMSO-d$_6$) δ 9.29 (br. s, 2 H), 8.23–8.16 (m, 2 H), 8.01 (d, J=8.2 Hz, 1 H), 7.64–7.49 (m, 2 H), 7.25 (d, J=8.2 Hz, 1 H), 6.72 (d, J=8.4 Hz, 1 H), 6.56–6.48 (m, 2 H), 4.21–4.16 (m, 4 H), 3.38–3.31 (m, 4 H), 3.08 (s, 3 H); MS (ESI+) for C23 H25 N3 O4 S m/z 440 (M+H)$^+$.

Example 78

4-Piperazin-1-yl-naphthalene-1-sulfonic acid (2,3-dihydro-benzo[1,4]dioxin-6-yl)-amide, hydrochloride The final product was prepared according to Method F; Yield (36%); $^1$H NMR (270 MHz, DMSO-D6) δ ppm 3.32 (m, 8 H) 4.08 (m, 4 H) 6.45 (m, 2 H) 6.61 (d, J=8.44 Hz, 1 H) 7.20 (d, J=8.18 Hz, 1 H) 7.67 (m, 2 H) 8.07 (d, J=7.92 Hz, 1 H) 8.21 (d, J=8.71 Hz, 1 H) 8.67 (d, J=8.44 Hz, 1 H) 9.22 (s, 1 H) 10.32 (s, 1 H); MS (ESI+) for C22 H23 N3 O4 S m/z 426.2 (M+H)$^+$.

Example 79

4-Piperazin-1-yl-naphthalene-1-sulfonic acid methyl-(2-methylsulfanyl-phenyl)-amide, hydrochloride 4-Fluoro-N-methyl-N-(2-methylsulfanyl-phenyl)-amide—Methylation according to Method G; Yield (97%); $^1$H NMR (DMSO-d$_6$) δ 8.52–8.49 (m, 1 H), 8.22–8.19 (m, 1 H), 8.16 (dd, J=8.4, 5.5 Hz, 1 H), 7.79–7.66 (m, 2 H), 7.52 (dd, J=10.0, 8.4 Hz, 1 H), 7.37–7.24 (m, 2 H), 7.06–7.00 (m, 1 H), 6.88 (dd, J=7.9, 1.3 Hz, 1 H), 3.10 (s, 3 H), 2.28 (s, 3 H).

The final product was prepared according to Method F; Trituration with MeCN; Yield (65%) $^1$H NMR (DMSO-d$_6$) δ 9.27 (br. s, 2 H), 8.54–8.50 (m, 1 H), 8.27–8.23 (m, 1 H), 8.09 (d, J=8.2 Hz, 1 H), 7.67–7.56 (m, 2 H), 7.38–7.25 (m, 3 H), 7.07–6.92 (m, 2 H), 3.41–3.33 (m, 8 H), 3.06 (s, 3 H), 2.30 (s, 3 H); MS (ESI+) for C22 H25 N3 O2 S$_2$ m/z 428 (M+H)$^+$.

Example 80

4-Piperazin-1-yl-naphthalene-1-sulfonic acid methyl-(3-trifluoromethyl-phenyl)-amide, hydochloride N-(3-trifluoromethylphenyl)-4-fluoronaphthalenesulphonamide—Method E; Yield (90%). $^1$H NMR (CDCl$_3$) δ 8.65–8.62 (m, 1 H), 8.23–8.18 (m, 2 H), 7.78–7.65 (m, 2 H), 7.31–7.17 (m, 2 H), 7.16–7.08 (m, 3 H); MS (ESI+) for C17 H11 F4 N O2 S m/z 370 (M+H)$^+$. Methylation according to Method F; Yield (100%); $^1$H NMR (DMSO-d$_6$) δ 8.19–8.11 (m, 2 H), 8.01–7.98 (m, 1 H), 7.73–7.62 (m, 2 H), 7.57–7.44 (m, 4 H), 7.35 (br. s, 1 H), 3.21 (s, 3 H).

The final product was prepared according to Method F; Trituration with MeCN; Yield 0.07 g (40%). $^1$H NMR (DMSO-d$_6$) δ 9.35 (br. s, 2 H), 8.21 (d, J=8.2 Hz, 1 H), 8.06–8.02 (m, 2 H), 7.63–7.42 (m, 5 H), 7.28–7.24 (m, 2 H), 3.39 (br. s, 8 H), 3.21 (s, 3 H), 2.06 (s, 3 H); MS (ESI+) for C22 H22 F3 N3 O2 S m/z 450 (M+H)$^+$.

Example 81

4-Piperazin-1-yl-naphthalene-1-sulfonic acid (3-chloro-4-methyl-phenyl)-methyl-amide, hydrochloride N-(3-Chloro-4-methylphenyl)-4-fluoronaphthalenesulphonamide—Method E; Yield (88%). $^1$H NMR (DMSO-d$_6$) δ 10.86 (br. s, 1 H), 8.74–8.71 (m, 1 H), 8.22 (dd, J=8.3, 5.4 Hz, 1 H), 8.19–8.16 (m, 1 H), 7.89–7.75 (m, 2 H), 7.47 (dd, J=10.0, 8.4 Hz, 1 H), 7.12–7.09 (m, 1 H), 7.00 (d, J=2.2 Hz, 1 H), 6.86 (dd, J=8.3, 2.2 Hz, 1 H), 2.11 (s, 3 H);

4-Fluoro-1-naphthalene-1-sulfonic acid (3-chloro-4-methyl-phenyl)-methyl-amide—Methylation according to Method G; Yield (100%). $^1$H NMR (DMSO-d$_6$) δ 8.20–8.07 (m, 3 H), 7.76–7.70 (m, 1 H), 7.62–7.48 (m, 2 H), 7.27–7.24 (m, 1 H), 7.13 (d, J=2.4 Hz, 1 H), 6.99 (dd, J=8.2, 2.4 Hz, 1 H), 3.15 (s, 3 H), 2.28 (s, 3 H);

The final product was prepared according to Method F; Yield (28%). $^1$H NMR (DMSO-d$_6$) δ 9.29 (br. s, 2 H), 8.24–8.15 (m, 2 H), 8.01 (d, J=8.2 Hz, 1 H), 7.65–7.47 (m, 2 H), 7.26 (dd, J=8.3, 4.6 Hz, 2 H), 7.09–7.08 1 H), 7.03–6.99 (m, 1H), 3.38–3.33 (m, 8 H), 3.14 (s, 3 H), 2.27 (s, 3 H);MS (ESI+) for C22 H24 Cl N3 O2 S m/z 430 (M+H)$^+$.

Example 82

4-Piperazin-1-yl-naphthalene-1-sulfonic acid (3-ethyl-phenyl)-methyl-amide, hydrochloride N-(3-ethylphenyl)-4-fluoronaphthalenesulphonamide—Method E; Yield (85%). $^1$H NMR (CDCl$_3$) δ 8.66 (d, J=8.4 Hz, 1 H), 8.20–8.14 (m, 2 H), 7.75–7.62 (m, 2 H), 7.10 (dd, J=9.5, 8.4 Hz, 1 H), 7.02 (t, J=7.8 Hz, 1 H), 6.88–6.85 (m, 1 H), 6.72–6.68 (m, 3 H), 2.45 (q, J=7.7 Hz, 2 H), 1.03 (t, J=7.7 Hz, 3 H)

4-Fluoro-1-yl-naphthalene-1-sulfonic acid (3-ethyl-phenyl)-methyl-amide—Methylation according to Method G; Yield (100%); $^1$H NMR (DMSO-d$_6$) δ 8.18–8.06 (m, 3 H), 7.72–7.66 (m, 1 H), 7.54–7.48 (m, 2 H), 7.21–7.16 (m, 1 H), 7.10–7.08 (m, 1 H), 6.96–6.92 (m, 1 H), 6.81–6.80 (m, 1 H), 3.16 (s, 3 H), 2.41 (q, J=7.5 Hz, 2 H), 0.93 (t, J=7.5 Hz, 3 H)

The final product was prepared according to Method f; Trituration with MeCN; Yield (49%); $^1$H NMR (DMSO-d$_6$) δ 9.21 (br. s, 2 H), 8.21 (d, J=8.4 Hz, 1 H), 8.13 (d, J=8.7 Hz, 1 H), 8.02 (d, J=8.2 Hz, 1 H), 7.62–7.57 (m, 1 H), 7.47–7.41 (m, 1 H), 7.27–7.17 (m, 2 H), 7.10–6.95 (m, 2 H), 6.8 (br. s, 1 H), 3.40–3.29 (m, 8 H), 3.15 (s, 3 H), 2.43 (q, J=7.6 Hz, 2 H), 0.95 (t, J=7.6 Hz, 2 H); MS (ESI+) for C23 H27 N3 O2 S m/z 410 (M+H)$^+$.

Example 83

4-(3,5-Dimethyl-piperazin-1-yl)-naphthalene-1-sulfonic acid (2-isopropyl-phenyl)-amide, hydrochloride The final product was prepared according to Method F; Yield (35%); $^1$H NMR (270 MHz, DMSO-D6) δ ppm 0.64 (d, J=6.86 Hz, 6 H) 1.30 (d, J=6.60 Hz, 6 H) 2.92 (m, 3 H) 3.53 (m, 4 H) 6.86 (d, J=7.65 Hz, 1 H) 6.98 (m, 1 H) 7.13 (m, 3 H) 7.67 (m, 2 H) 7.86 (d, J=7.92 Hz, 1 H) 8.24 (m, 1 H) 8.74 (m, 1 H) 9.08 (m, 1 H) 9.79 (m, 2 H); MS (ESI+) for C25 H31 N3 O2 S m/z 438.01 (M+H)$^+$.

Example 84

4-[1,4]Diazepan-1-yl-naphthalene-1-sulfonic acid (2-isopropyl-phenyl)-amide, hydrochloride N-(2 isopropylphenyl)-4-fluoronaphthalensulphonamide—Method E; Yield (87%) $^1$H NMR (CDCl$_3$) δ 8.67–8.64 (m, 1 H), 8.22–8.18 (m, 1 H), 8.12 (dd, J=8.3, 5.4 Hz, 1 H), 7.71–7.62 (m, 2 H), 7.15–6.97 (m, 5 H), 2.84–2.73 (m, 1 H), 0.85 (s, 3 H), 0.82 (s, 3 H)

The final product was prepared according to Method F; Yield (22%). $^1$H NMR (DMSO-d6) δ 9.83 (s, 1 H), 9.37 (br. s, 2 H), 8.74–8.70 (m, 1 H), 8.27.8.24 (m, 1 H), 7.84 (d, J=7.9 Hz, 1 H), 7.68–7.64 (m, 2 H), 7.17–7.11 (m, 3 H), 7.01–6.87 (m, 2 H), 3.82 (br. s, 6 H), 3.51–3.50 (m, 2 H), 3.38–3.28 (m, 2 H), 3.02–2.93 (m, 1 H), 0.65 (s, 3 H), 0.63 (s, 3 H); MS (ESI+) for C24 H29 N3 O2 S m/z 424.02 (M+H)$^+$.

Example 85

4-[1,4]Diazepan-1-yl-naphthalene-1-sulfonic acid (3-ethyl-phenyl)-amide, hydrochloride The final product was prepared according to Method F; Yield (22%); $^1$H NMR (DMSO-d$_6$) δ 10.53 (s, 1 H), 9.24 (br. s, 2 H), 8.68 (d, J=8.2 Hz, 1 H), 8.20 (d, J=7.9 Hz, 1 H), 8.14 (d, J=8.2 Hz, 1 H), 7.72–7.60 (m, 2 H), 7.22 (d, J=8.2 Hz, 1 H), 7.01 (t, J=7.8 Hz, 1 H), 6.83–6.72 (m, 3 H), 3.33 (br. s, 6 H), 2.39 (q, J=7.7 Hz, 2 H), 2.12 (br. s, 2 H), 0.98 (t, J=7.5 Hz, 3 H); MS (ESI+) for C23 H27N3 O2 S m/z 410.03 (M+H)$^+$.

Example 86

N-(2-Fluorophenyl)-4-piperazin-1-ylnaphthalene-1-sulfonamide, hydrochloride

N-(2-Fluorophenyl)-4-fluoronaphthalensulphonamide—Method E; Yield (88%); $^1$H NMR (DMSO-d$_6$) δ 10.41 (br. s, 1 H), 8.76–8.69 (m, 1 H), 8.20–8.17 (m, 1 H), 8.08 (dd, J=8.0, 5.5 Hz, 1 H), 7.82–7.75 (m, 2 H), 7.41 (dd, J=10.0, 8.3 Hz, 1 H), 7.20–7.01 (m, 4 H); MS (ESI−) for C16 H11 F2 N O2 S m/z 318.2 (M−H)$^−$.

The final product was prepared according to Method F; Yield (22%); $^1$H NMR (DMSO-d$_6$) δ 10.41 (s, 1 H), 9.35 (m, 2 H), 8.72–8.68 (m, 1 H), 8.24–8.20 (m, 1 H), 8.02 (d, J=7.9 Hz, 1 H), 7.72–7.62 (m, 2 H), 7.22–7.00 (m, 5 H), 4.05 (d, J=1.3 Hz, 4 H), 3.36 (s, 4 H); MS (ESI+) for C20 H20 F N3 O2 S m/z 386 (M+H)$^+$.

Example 87

4-[1,4]Diazepan-1-yl-naphthalene-1-sulfonic acid (3-trifluoromethyl-phenyl)-amide, hydrochloride The final product was prepared according to Method F; Yield (21%); $^1$H NMR (DMSO-d6) δ 11.1 (s, 1 H), 9.32 (br. s, 2 H), 8.65 (d, J=8.2 Hz, 1 H), 8.19 (t, J=8.6 Hz, 2 H), 7.75–7.62 (m, 2 H), 7.42–7.22 (m, 4 H), 3.88 (br. s, 6 H), 3.55–3.53 (m, 2 H), 2.11 (m, 2 H); MS (ESI+) for C22 H22 F3 N3 O2 S m/z 449.95 (M+H)$^+$.

Example 88

N-(2,4-difluorophenyl)-4-piperazin-1-ylnaphthalene-1-sulfonamide, hydrochloride N-(2,4-di-Fluorophenyl)-4-fluoronaphthalensulphonamide—Method E; Yield (81%); $^1$H NMR (DMSO-d$_6$) δ 10.44 (s, 1 H), 8.73–8.69 (m, 1 H), 8.21–8.18 (m, 1 H), 8.02 (dd, J=8.4, 5.5 Hz, 1 H), 7.85–7.76 (m, 2 H), 7.41 (dd, J=10.2, 8.3 Hz, 1 H), 7.22–7.11 (m, 2 H), 7.01–6.93 (m, 1 H); MS (ESI–) for C16 H10 F3 N O2 S m/z 336.2 (M–H)$^-$.

The final product wass prepared according to Method F; Yield (27%); $^1$H NMR (DMSO-d6) δ 10.33 (s, 1 H), 9.28 (br. s, 2 H), 8.68–8.65 (m, 1 H), 8.25–8.21 (m, 1 H), 8.0 (d, J=8.2 Hz, 1 H), 7.73–7.62 (m, 2 H), 7.21–7.08 (m, 3 H), 7.0–6.93 (m, 1 H), 3.29 (br. s, 4 H); MS (ESI+) for C20 H19 F2 N3 O2 S m/z 403.94 (M+H)$^+$.

Example 89

4-Piperazin-1-yl-naphthalene-1-sulfonic acid (2-trifluoromethoxy-phenyl)-amide, hydrochloride N-(2-tri-Fluoromethoxyphenyl)-4-fluoronephthylsulphonamide—Method E; Yield (43%); $^1$H NMR (DMSO-d$_6$) δ 10.58 (s, 1 H), 8.80–8.76 (m, 1 H), 8.20–8.17 (m, 1 H), 8.08 (dd, J=8.3, 5.4 Hz, 1 H), 7.84–7.74 (m, 2 H), 7.42 (dd, J=10.2, 8.3 Hz, 1 H), 7.32–7.18 (m, 4 H).

The final product was preapred according to Method F; Yield (48%); $^1$H NMR (DMSO-d6) δ 10.49 (s, 1 H), 9.27 (br. s, 2 H), 8.75–8.72 (m, 1 H), 8.24–8.21 (m, 1 H), 8.02 (d, J=7.9 Hz, 1 H), 7.71–7.62 (m, 2 H), 7.32–7.17 (m, 5 H), 3.38 (br. s, 4 H), 3.28 (br. s, 4 H); S (ESI+) for C21 H20 F3 N3 O3 S m/z 451.9 (M+H)$^+$.

Example 90

4-Piperazin-1-yl-naphthalene-1-sulfonic acid (3-phenoxy-phenyl)-amide, hydrochloride N-(3-phenyloxyphenyl)-4-fluoronephthylsulphonamide—Method E; Yield 0.64 g (100%); $^1$H NMR (DMSO-d$_6$) δ 10.80 (br. s, 1 H), 8.71–8.68 (m, 1 H), 8.19–8.16 (m, 1 H), 8.10 (dd, J=8.3, 5.4 Hz, 1 H), 7.85–7.74 (m, 2 H), 7.45 (dd, J=10.2, 8.3 Hz, 1 H), 7.38–7.31 (m, 2' H), 7.18–7.10 (m, 2 H), 6.82–6.73 (m, 3 H), 6.58–6.55 (m, 2 H); MS (ESI–) for C22 H16 F N O3 S m/z 392.2 (M–H)$^-$.

The final product was preapred according to Method F; Yield 0.08 g (31%); $^1$H NMR (DMSO-d6) δ 10.76 (s, 1 H), 9.37 (br. s, 2 H), 8.67–8.63 (m, 1 H), 8.23–8.20 (m, 1 H), 8.02 (d, J=8.2 Hz, 1 H), 7.73–7.62 (m, 2 H), 7.41–7.35 (m, 2 H), 7.20–7.09 (m, 3 H), 6.84–6.73 (m, 3 H), 6.60–6.52 (m, 2 H), 3.47–3.37 (m, 8 H); MS (ESI+) for C26 H25 N3 O3 S m/z 459.95 (M+H)$^+$.

Example 91

4-Piperazin-1-yl-naphthalene-1-sulfonic acid (3-trifluoromethoxy-phenyl)-amide, hydrochloride N-(3-Trifluoromethoxyphenyl)-4-fluoronaphthalensulphonamide—Method E; Yield (35%); $^1$H NMR (DMSO-d6) δ 11.01 (br.s, 1 H), 8.74–8.71 (m, 1 H), 8.26 (dd, J=8.3, 5.3 Hz, 1 H), 8.16 (d, J=9.0 Hz, 1 H), 7.86–7.82 (m, 1 H), 7.78–7.74 (m, 1 H), 7.46 (dd, J=10.0, 8.5 Hz, 1 H), 7.27 (t, J=8.3 Hz, 1 H), 7.02–6.90 (m, 3 H); MS (ESI–) for C17 H11 F4 N O3 S m/z 383.8 (M–H)$^-$.

The final product was prepared according to Method F; Yield (35%); $^1$H NMR (DMSO-d6) δ 11.07 (s, 1 H), 9.63 (br. s, 1 H), 9.31 (br. s, 1 H), 8.66 (d, J=8.4 Hz, 1 H), 8.21–8.18 (m, 2 H), 7.75–7.62 (m, 2 H), 7.29–7.21 (m, 2 H), 7.03–6.86 (m, 3 H), 3.32–3.28 (m, 8 H); MS (ESI+) for C26 H25 N3 O3 S m/z 451.94 (M+H)$^+$.

Example 92

4-Piperazin-1-yl-naphthalene-1-sulfonic acid (2-chloro-5-methyl-phenyl)-amide, hydrochloride The final product was prepared according to method F: $^1$H NMR ((DMSO-d6) δ; 10.10 (brs, 1H), 9.25 (brs, 2H), 8.76–8.66 (m, 1H), 8.27–8.17 (m, 1H), 8.00–7.94 (m, 1H), 7.71–7.60 (m, 2H), 7.25–7.11 (m, 2H), 7.02 (s, 1H), 6.99–6.92 (m, 1H), 3.40–3.20 (m, obscured by solvent signal) 2.17 (s, 3H), MS (posESI) m/z=416 (M+H).

Example 93

4-Piperazin-1-yl-naphthalene-1-sulfonic acid (4-isopropyl-phenyl)-amide, hydrochloride The final product was prepared according to method F: $^1$H NMR ((DMSO-d6) δ; 10.52 (s, 1H), 9.26 (brs, 2H), 8.74–8.66 (m, 1H), 8.27–8.11 (m, 2H), 7.76–7.60 (m, 2H), 7.26.7.17 (m, 1H), 7.06–6.89 (m, 4H), 3.40–3.20 (m, obscured by solvent signal), 2.77–2.61 (m, 1H), 1.05 (d, J=6.87 Hz, 6H), MS (posESI) m/z=410 (M+H).

Example 94

N-(3,5-Difluorophenyl)-4-piperazin-1-ylnaphthalene-1-sulfonamide, hydrochloride The final product was prepared according to Method F using the crude N-(3,5-difluorophenyl)-4-fluoronaphthalene-1-sulfonamide (50 mg, 0.15 mmol) afforded the title compound (20 mg, 31%) as a yellow solid. $^1$H NMR (DMSO) δ 11.33 (s, 1H), 9.35 (br s, 2H), 8.69 (m, 1H), 8.30–8.18 (m, 2H), 7.80–7.61 (m, 2H), 7.30–7.21 (m, 1H), 6.84–6.62 (m, 3H), 3.45–3.24 (m, 8H); MS m/z (M+1) 404.

Example 95

1-[4-(3,4-Dihydroquinolin-1(2 H)-ylsulfonyl)-1-naphthyl]piperazine, hydrochloride 4-Fluoronaphthalene-1-sulfonyl chloride—To a stirred solution of 1-fluoronaphthalene (8.0 g, 55 mmol) in concentrated trifluoroacetic acid (40 ml), chlorosulfonic acid was added slowly (15 min) at 0° C. The mixture was stirred at room temperature for an additional 2 hours and then added slowly onto a stirred ice slurry. The formed precipitate filtered off, washed with cold water and dried in vacuo to give the title compound (7.3 g) as a white solid.

1-[(4-Fluoro-1-naphthyl)sulfonyl]-1,2,3,4-tetrahydroquinoline—Method E: To a stirred solution of 4-fluoronaphthalene-1-sulfonyl chloride (200 mg, 0.82 mmol) in DCM (1 ml) was added 1,2,3,4-tetrahydroquinoline (123 μl, 0.98 mmol) followed by pyridine (0.25 ml). The reaction mixture was stirred over night, diluted with DCM and washed with 1M HCl (3×3 ml). Subsequent drying of the organic phase using MgSO$_4$, and removal of the solvents in vacuo afforded the title compound (280 mg, 100%) as a white solid. $^1$H NMR (CDCl$_3$) δ 8.24–8.10 (m, 3H), 7.68–7.62 (m, 1H), 7.58–7.51 (m, 1H), 7.42–7.34 (m, 1H), 7.23–7.04 (m, 3H), 6.96–6.89 (m, 1H), 3.84–3.74 (m, 2H), 2.39–2.28 (m, 2H), 1.63–1.49 (m, 1H); MS m/z (M+1) 342.

The final product was prepared according to Method F: A stirred solution of 1-[(4-fluoro-1-naphthyl)sulfonyl]-1,2,3,4-tetrahydroquinoline (50 mg, 0.15 mmol) and piperazine (80 mg, 0.9 mmol) in DMSO (1 ml) was heated at 95° C. over night. The reaction mixture was allowed to reach room temperature and was subsequently added dropwise into water. The formed solid was isolated, re-dissolved in MeOH and treated with an excess of 1M HCl in diethyl ether. Removal of the solvents in vacuo afforded the title compound (60 mg, 83%) as a white solid. $^1$H NMR (DMSO) δ 9.17 (br s, 2H), 8.23–8.06 (m, 3H), 7.61–7.55 (m, 1H), 7.48–7.38 (m, 2H), 7.29–7.23 (m, 1H), 7.19–7.12 (m, 1H), 7.09–6.98 (m, 2H), 3.78–3.71 (m, 2H), 3.44–3.30 (m, 8H), 2.42–2.32 (m, 2H), 1.57–1.48 (m, 2H); MS m/z (M+1) 408.

Example 96

4-[1,4]Diazepan-1-yl-naphthalene-1-sulfonic acid (3-nitro-phenyl)-amide, hydrochloride The final product was prepared according to Method F: $^1$H NMR ((DMSO-d6) δ; 8.68–8.63 (m, 1H), 8.27–8.13 (m, 2H), 7.78 (s, 1H), 7.72–7.53 (m, 3H), 7.35–7.16 (m, 3H), 3.55–3.40 (m, 6H), 3.34–3.27 (m, obscured in part by solvent signal), 2.22–2.13 (m, 2H), MS (posESI) m/z=427 (M+H).

Example 97

4-Piperazin-1-yl-naphthalene-1-sulfonic acid (3-nitro-phenyl)-amide, hydrochloride The final product was prepared according to Method F: $^1$H NMR ((DMSO-d6) δ; 8.68–8.60 (m, 1H), 8.24–8.13 (m, 2H), 7.77 (s, 1H), 7.71–7.53 (m, 3H), 7.30–7.20 (m, 2H), 7.16–7.10 (m, 1H), 3.45–3.40 (m, 4H), 3.31–3.20 (m, 4H), MS (posESI) m/z=413 (M+H).

Example 98

4-[1,4]Diazepan-1-yl-naphthalene-1-sulfonic acid (3-nitro-phenyl)-methyl-amide, hydrochloride The final product was prepared according to Method F: $^1$H NMR (DMSO-d6) δ; 8.21 (d, J=8.47 Hz, 1H), 8.12 (d, J=8.79 Hz, 1H), 8.01–7.95 (m, 2H), 7.64 (s, 1H), 7.54–7.39 (m, 3H), 7.34–7.28 (m, 1H), 7.23–7.18 (m, 1H), 3.60–3.30 (m, 8H), 3.17 (s, 3H), 2.24–2.16 (m, 2H), MS (posESI) m/z=441 (M+H).

Example 99

N-(4-Methylphenyl)-4-piperazin-1-ylnaphthalene-1-sulfonamide, hydrochloride

4-Fluoro-N-(4-methylphenyl)naphthalene-1-sulfonamide—Method E: Use of 4-methylaniline afforded the title compound (500 mg, 95%) as an oil by the application of the general procedure A described above. $^1$H NMR (CDCl$_3$) δ 8.82–8.75 (m, 1H), 8.22–8.13 (m, 2H), 7.73–7.58 (m, 2H), 7.44 (s, 1H), 7.11–7.02 (m, 1H), 6.93–6.80 (m, 4H), 2.17 (s, 3H); MS m/z (M+1) 316.

The final product was prepared according to Method E: Use of 4-fluoro-N-(4-methylphenyl)naphthalene-1-sulfonamide afforded the title compound (200 mg, 30%), after washing with methanol, as a yellow solid. $^1$H NMR (DMSO) δ 10.46 (s, 1H), 9.30 (br s, 2H), 8.76–8.65 (m, 1H), 8.25–8.06 (m, 2H), 7.78–7.59 (m, 2H), 7.25–7.14 (m, 1H), 6.98–6.83 (4H), 3.41–3.22 (m, 8H), 2.09 (s, 3H); MS m/z (M+1) 382.

Example 100

N-(3-Chloro-4-methylphenyl)-4-piperazin-1-ylnaphthalene-1-sulfonamide, hydrochloride The final product was prepared according to Method E: yield 100%, purity 93% $^1$H NMR (500 MHz, DMSO-D6) δ ppm 2.26 (s, 3 H), 2.74 (m, 4 H), 3.54 (m, 4 H), 7.23 (m, 4 H), 7.83 (m, 2 H), 8.31 (m, 2 H), 8.81 (s, 1 H), 9.11 (s, 1 H, N—H), 10.86 (s, 1 H, N—H); MS (ESI+) for C21 H22 Cl N3 O2 S HCl m/z (M+H)$^+$. 416.1; MS (ESI–) for C21 H22 Cl N3 O2 S HCl m/z (M–H)$^-$. 414.1.

Example 101

4-[1,4]Diazepan-1-yl-naphthalene-1-sulfonic acid (2,3-dimethyl-phenyl)-methyl-amide, hydrochloride The final product was prepared according to Method F: $^1$H NMR (DMSO-d6) δ; 8.51–8.41 (m, 1H), 8.39–8.30 (m, 1H), 8.11–7.99 (m, 1H), 7.68–7.56 (m, 1H), 7.54–7.42 (m, 1H), 7.35–7.23 (m, 1H), 7.13–7.02 (M, 1H), 6.90–6.78 (m, 1H), 6.62–6.47 (m, 1H), 3.70–3.40 (m, 8H), 3.17 (s, 3H), 2.25 (s, 3H), 2.10 (s, 3H), MS (posESI) m/z=424 (M+H).

Example 102

4-[1,4]Diazepan-1-yl-naphthalene-1-sulfonic acid (4-isopropyl-phenyl)-amide, hydrochloride The final product was prepared according to Method F: $^1$H NMR ((DMSO-d6) δ; 8.74 (d, J=8.16 Hz, 1H), 8.33 (d, J=8.48 Hz, 1H), 8.15–8.10 (m, 1H), 7.72–7.62 (m, 2H), 7.25–7.21 (m, 1H), 6.99–6.86 (m, 4H), 3.62–3.57 (m, 2H), 3.56–3.50 (m, 4H), 3.41–3.35 (m, 2H), 2.79–2.69 (m, 1H), 2.32–2.22 (m, 2H), 1.14–1.10 (m, 6H), MS (posESI) m/z=424 (M+H).

Example 103

4-[1,4]Diazepan-1-yl-naphthalene-1-sulfonic acid (4-isopropyl-phenyl)-methyl-amide, hydrochloride The final product was prepared according to Method F: $^1$H NMR (DMSO-d6) δ; 8.13–8.07 (m, 1H), 8.01–7.93 (m, 1H), 7.51–7.41 (m, 1H), 7.38–7.15 (m, 2H), 7.00–6.95 (m, 2H), 6.89–6.85 (m, 2H), 3.59–3.28 (m, 8H), 3.09 (s, 3H), 2.81–2.71 (m, 1H), 1.11 (d, J=6.60 Hz, 6H), MS (posESI) m/z=438 (M+H).

Example 104

4-[1,4]Diazepan-1-yl-naphthalene-1-sulfonic acid (2,4-dimethyl-phenyl)-amide, hydrochloride The final product was prepared according to Method F: $^1$H NMR ((DMSO-d6) δ; 8.70–8.61 (m, 1H), 8.30–8.20 (m, 1H), 7.91–7.78 (m, 1H), 7.60–7.51 (m, 2H), 7.14–7.06 (m, 1H), 6.76–6.59 (m, 3H), 3.64–3.40 (m, 6H), 3.35–3.30 (m, obscured in part by solvent signal), 2.24–2.13 (m, 2H), 2.07 (s, 3H), 1.76 (s, 3H), MS (posESI) m/z=410 (M+H).

Example 105

4-[1,4]Diazepan-1-yl-naphthalene-1-sulfonic acid (2-chloro-5-methyl-phenyl)-amide, hydrochloride The final product was prepared according to Method F: $^1$H NMR ((DMSO-d6) δ; 8.67–8.61 (m, 1H), 8.24–8.19 (m, 1H), 7.95 (d, J=8.16 Hz, 1H), 7.57–7.56 (m, 2H), 7.21–7.18 (m, 1H), 7.12 (d, J=8.17 Hz, 1H), 6.89 (d, J=8.17 Hz, 1H), 6.78–6.75 (m, 1H), 3.52–3.47 8m, 2H), 3.45–3.40 (m, 4H), 3.31–3.26 (m, 2H), 2.20–2.10 (m, 2H), 2.14 (s, 3H), MS (posESI) m/z=430 (M+H).

Example 106

4-Piperazin-1-yl-naphthalene-1-sulfonic acid (2,5-dimethoxy-phenyl)-amide, hydrochloride The final product was prepared according to Method F: $^1$H NMR ((DMSO-d6) δ; 8.80–8.72 (m, 1H), 8.27–8.19 (m, 1H), 7.98 (d, J=8.18 Hz, 1H), 7.74–7.60 (m, 2H), 7.17 (d, J=7.91 Hz, 1H), 6.76–6.75 (m, 2H), 6.62–6.55 (m, 1H), 3.60 (s, 3H), 3.40–3.20 (m, obscured by solvent signal), 3.12 (s, 3H), MS (posESI) m/z=428 (M+H).

Example 107

4-Piperazin-1-yl-naphthalene-1-sulfonic acid (3-acetyl-phenyl)-amide; hydrochloride The final product was prepared according to Method F: $^1$H NMR ((DMSO-d6) δ; 8.79–8.72 (m, 1H), 8.29–8.21 (m, 2H), 7.75–7.62 (m, 2H), 7.59–7.52 (m, 2H), 7.26–7,19 (m, 3H), 3.52–3.44 (m, 4H), 3.39–3.30 (m, obscured by solvent signal), 2.43 (s, 3H), MS (posESI) m/z=410 (M+H).

Example 108

4-Piperazin-1-yl-naphthalene-1-sulfonic acid (2,4-dimethyl-phenyl)-amide, hydrochloride The final product was prepared according to Method F: $^1$H NMR ((DMSO-d6) δ; 8.81–8.72 (m, 1H), 8.34–8.25 (m, 1H), 7.98 (d, J=8.18 hz, 1H), 7.71–7.60 (m, 2H), 7.14 (d, J=8.18 Hz, 1H), 6.81 (s, 1H), 6.76–6.72 (m, 2H), 3.58–3.47 (m, 4H), 3.44–3.30 (m, obscured in part by solvent signal), 2.16 (s, 3H), 1.84 (s, 3H), MS (posESI) m/z 396 (M+H).

Example 109

4-Piperazin-1-yl-naphthalene-1-sulfonic acid (3-trifluoromethyl-phenyl)-amide, hydrochloride The final product was prepared according to Method F: $^1$H NMR ((DMSO-d6) δ; 8.72–8.64 (m, 1 H9, 82.7–8.16 (m, 2H), 7.81–7.62 (m, 2H), 7.45–7.19 (m, 5H), 3.40–3.20 (m, obscured by solvent signal), MS (posESI) m/z=436 (M+H).

Example 110

4-Piperazin-1-yl-naphthalene-1-sulfonic acid Biphenyl-2-ylamide, hydrochloride

The final product was prepared according to Method F: $^1$H NMR ((DMSO-d6) δ; 9.71 (s, 1H), 944 (brs, 2H), 8.51–8.42 (m, 1H), 8.24–8.15 (m, 1H), 7.83 (d, J=8.18 Hz, 1H), 7.66–7.49 (m, 2H), 7.29–6.98 (m, 10H), 3.50–3.30 (m, obscured by solvent signal), MS (posESI) m/z=444 (M+H).

Example 111

4-Piperazin-1-yl-naphthalene-1-sulfonic acid (3-benzyloxy-phenyl)-amide,

N-(3-phenyloxyphenyl)-4-fluoronaphthalensulphonamide—Method E; Yield 9.2 g (47%). $^1$H NMR (DMSO-d$_6$) δ 10.75 (s, 1H), 8.75 (d, J=8.4 Hz, 1H), 8.23–8.14 (m, 2 H), 7.87–7.73 (m, 2 H), 7.44 (dd, J=10.2, 8.3 Hz, 1 H), 7.34–7.29 (m, 5 H), 7.03 (t, J=8.2 Hz, 1 H), 6.66–6.56 (m, 3 H), 4.93 (s, 2 H); MS (ESI+) for C23 H18 F N O3 S m/z 407 (M+H)$^+$.

The final product was prepared according to Method F: Yield 0.6 g (78%); $^1$H NMR (DMSO-d$_6$) δ 10.67 (s, 1 H), 9.30 (br. s, 2 H), 8.69 (d, J=7.7 Hz, 1 H), 8.21 (d, J=8.4 Hz, 1 H), 8.13 (d, J=8.2 Hz, 1 H), 7.75–7.61 (m, 2 H), 7.35–7.30 (m, 5 H), 7.19 (d, J=8.2 Hz, 1 H), 7.03 (t, J=8.2 Hz, 1 H), 6.68–6.54 (m, 3 H), 4.93 (s, 2 H), 3.36–3.29 (m, 8 H); MS (ESI+) for C27 H27 N3 O3 S m/z 474 (M+H)$^+$.

Example 112

N-(4-fluorophenyl)-4-piperazin-1-ylnaphthalene-1-sulfonamide, hydrochloride4-Fluoro-N-(4-fluorophenyl)naphthalene-1-sulfonamide—Method E: Use of 4-methoxyaniline afforded the title compound (475 mg, 86%) as an oil by the application of the general procedure A described above. $^1$H NMR (CDCl$_3$) δ 8.79–8.71 (m, 1H), 8.23–8.10 (m, 2H), 7.75–7.59 (2H), 7.52–7.45 (m, 1H), 7.15–7.04 (m, 1H), 6.96–6.73 (m, 4H); MS m/z (M+1) 320.

The final product was prepared according to Method F: Use of 4-fluoro-N-(4-fluorophenyl)naphthalene-1-sulfonamide afforded the title compound (95 mg, 15%), after recrystallization from methanol, as a white solid by the application of the general procedure B described above. $^1$H NMR (DMSO) δ 10.60 (s, 1H), 9.37 (br s, 2H), 8.73–8.65 (m, 1H), 8.25–8.17 (m, 1H), 8.13–8.06 (m, 1H), 7.76–7.60 (m, 2H), 7.22–7.15 (m, 1H), 7.04–6.95 (m, 4H), 3.43–3.24 (m, 8H); MS m/z (M+1) 386.

Example 113

N-(3-Ethylphenyl)-4-piperazin.1.ylnaphthalene-1-sulphonamine, hydrochloride

N-(3-Ethylphenyl)-4-fluoronaphthalene-1-sulfonamide—Method E: yield 80%, purity 92%. $^1$H NMR (270 MHz, CDCl$_3$) δ ppm 1.03 (t, J=7.52 Hz, 3 H), 2.45 (q, J=7.65 Hz, 2 H), 6.68–6.72 (m, 2 H, N—H), 6.87 (d, J=7.13 Hz, 1 H), 6.99–7.13 (m, 2H), 7.65–7.72 (m, 2 H), 8.13–8.20 (m, 2 H), 8.65 (d, J=8.44 Hz, 1 H); MS (ESI+) for C18 H16 F N O2 S m/z 329.393 (M+H)$^+$. 330.0; MS (ESI–) for C18 H16 F N O2 S m/z 329.393 (M–H)$^-$. 328.1

The final product was prepared according to Method F: yield 61%, purity 98%. $^1$H NMR (500 MHz, DMSO) δ 8.67–8.65 (m, 1H), 8.16–8.10 (m, 2H), 7.66–7.57 (m, 2H), 7.14 (d, J=8.56 Hz, 1H), 6.97–6.94 (m, 1H), 6.78–6.76 (m, 2H), 6–70–6.69 (m, 1H), 3.30–3.28 (m, 2H), 3.22–3.19 (m, 2H), 2.34 (q, J=17 Hz, 2H), 1.94 (tr, J=17 Hz, 3H); MS (ESI+) for C22 H25 N3 O2 S HCl m/z 431.98 (M–HCl+H)$^+$. 396.1; MS (ESI–) for C22 H25 N3 O2 S HCl m/z (M–HCl–H)$^-$. 394.1

Example 114

4-Piperazinyl-N-[3-(trifluoromethyl)phenyl]naphthalene-1-sulfonamide, hydrochloride The final product was prepared according to Method F: Use of 4-fluoro-N-(3-trifluoromethythiophenyl)naphthalene-1-sulfonamide afforded the title compound (0.08 g), gave 0.060 g of the desired product, yield 85%, purity 96%.

$^1$H NMR (270 MHz, CD$_3$OD) δ 8.74–8.71 (m, 1H), 8.26–8.19 (m, 2H), 7.75–7.65 ( m, 2H), 7.32 (br.s, 1H), 7.23–7.14 (m, 4H), 3.57–3.47 (m, 4H), 3.35–3.30 (m, 4H); MS (ESI+) for C21 H20 F3 N3 O2 S2HCl m/z 467.09+35.46 (M+H)$^+$468.0; MS (ESI+) for C21 H20 F3 N3 O2 S2HCl m/z 467.09+35.46 (M–H)$^-$466.1.

Example 115

4-Piperazinyl-N-[3-benzoylphenyl]naphthalene-1-sulfonamide, hydrochloride

The final product was prepared according to Method F: yield 25%, purity 97%. $^1$H NMR (270 MHz, CD$_3$OD) δ 8.76–8.72 (m, 1H), 8.29–8.26 (m, 1H), 8.17 (d, J=8,1 Hz, 1H), 7.73–7.60 (m, 3H), 7.55–7.44 (m, 4H), 7.34–7.28 (m, 4H), 7.18 (d, J=8,1 Hz, 1H), 3.54–3.50 (m, 4H), 3.37–3.30 (m, 4H); MS (ESI+) for C27 H25 N3 O3 S HCl m/z 471.17+35.46 (M+H)$^+$472.1; MS (ESI+)+) for C27 H25 N3 O3 S HCl m/z 471.17+35.46 (M–H)$^-$470.01.

Example 116

4-Piperazinyl-N-[3-(4-bromo-1-methyl-1H-pyrazol-3-yl)phenyl]naphthalene-1-sulfonamide, hydrochloride The final product was prepared according to Method F: yield 81%, purity 96%. $^1$H NMR (270 MHz, CD$_3$OD) δ 8.78–8.74 (m, 1H), 8.27–8.24 (m, 1H), 8.19 (d, J=8,1 Hz, 1H), 7.75–7.64 (m, 2H), 7.46 (s, 1H), 7.31–7.25 (m 11H), 7.19–7.16 (m, 2H), 7.02–6.96 (m, 2H), 3.57–3.49 (m, 4H), 3.52 (s, 3H), 3.35–3.30 (m, 4H); MS (ESI+) for C24 H24 Br N5 O2 S HCl m/z 525.08+35.46 (M+H)$^+$526.0; MS (ESI+) C24 H24 Br N5 O2 S HCl m/z 525.08+35.46 (M–H)$^-$524.1.

Example 117

4-Piperazinyl-N-[3-biphenylphenyl]naphthalene-1-sulfonamide, hydrochloride

The final product was prepared according to Method F: yield 33%, purity 95%. $^1$H NMR (270 MHz, CD$_3$OD) δ 8.83–8.80 (m, 1H), 8.26–8.22 (m, 2H), 7.79–7.68 (m, 2H), 7.39–7.35 (m, 5H), 7.23–7.19 (m, 4H), 7.03–6.99 (m, 1H), 3.52–3.47 (m, 4H), 3.35–3.30 (m, 4H); MS (ESI+) for C26 H25 N3 O2 S HCl m/z 443.17+36.45 (M+H)$^+$444.1; MS (ESI–) for C26 H25 N3 O2 S HCl m/z 443.17+36.45 (M–H)$^-$442.2.

Synthesis of Examples and Intermediates in Table IV

General Method H

Example 118

N-[1-(4-Methyl-1-piperazinyl)-3-isoquinolinyl]benzenesulfonamide, hydrochloride

To a solution of 1-(4-methyl-1-piperazinyl)-3-isoquinolinylamine (commercially available; 0.26 g, 1.07 mmol) and pyridine (0.60 mL, 7.51 mmol) in CH$_2$Cl$_2$ (3.0 mL) was added benzenesulfonyl chloride (151 μL, 1.18 mmol) in CH$_2$Cl$_2$ (1 mL). The mixture was stirred at room temperature for 16 hours and left in the refrigerator for 24 hours. The precipitate was collected by filtration to give 0.255 g (57%) of the pure product as the HCl-salt: $^1$H NMR (DMSO-d6) δ 10.93 (s, 2H), 7.96–7.90 (m, 3H), 7.79–7.75 (m, 1H), 7.64–7.56 (m, 4H), 7.44–7.38 (m, 1H), 7.01 (s, 1 H9, 3.70–3.15 (m, partly obscured by solvent signal, 8H), 2.79 (s, 3H); MS (posEI-DIP) m/z 382 (M$^+$).

Example 119

2,4-di-Fluoro-N-[1-(4-methyl-1-piperazinyl)-3-isoquinolinyl]benzenesulfonamide, hydrochloride The title compound was prepared from 1-(4-methyl-1-piperazinyl)-3-isoquinolinylamine (commercially available; 0.209 g, 0.862 mmol) using the method described in example that follows: yield 0.152 g (65%); $^1$H NMR (DMSO-d6) δ; 11.35 (s, 1H), 11.09 (br s, 1H), 8.15–8.04 (m, 1H), 7.97–7.90 (m, 1H), 7.83–7.35 (m, 5H), 6.95 (s, 1H), 3.70–3.10 (m, 8H), 2.85–2.75 (m, 3H); MS (posESI) m/z 419 (M+H).

Example 120

4-Bromo-N-[1-(4-methyl-piperazin-1-yl)-isoquinolin-3-yl]-benzenesulfonamide, hydrochloride $^1$H NMR (DMSO-d6) δ; 11.07 (s, 1H), 10.75 (br s, 1H), 7.98–7.75 (m, 5H), 7.66–7.58 (m, 1H), 7.52 (s, 1H), 7.47–7.37 (m, 1H), 7.00 (brs, 1H), 3.70–3.20 (obscured in part by solvent signal, 8H), 2.85–2.80 (m, 2H), MS (posESI) m/z=461 (M+H)

Example 121

5-Chloro-3-methyl-benzo[b]thiophene-2-sulfonic acid [1-(4-methyl-piperazin-1-yl)-isoquinolin-3-yl]-amide, hydrochloride $^1$H NMR (DMSO-d6) δ; 11.47 (br s,1H), 10.55 (br s, 1H), 8.14–8.07 (m, 1H), 8.01–7.98 (m, 1H), 7.96–7.98 (m, 1H), 7.82–7.76 (m, 1H), 7.67–7.52 (m, 2H), 7.47–7.39 (m, 1H), 7.06 (s, 1H), 3.80–3.65 (m, 2H), 3.60–3.25 (m, obscured by solvent signal), 2.80–2.73 (m, 3H),), MS (posESI) m/z=487 (M+H)

Example 122

3-Chloro-2-methyl-N-[1-(4-methyl-piperazin-1-yl)-isoquinolin-3-yl]-benzenesulfonamide, hydrochloride $^1$H NMR (DMSO-d6) δ; 11.24 (br s, 1H), 10.56 (br s, 1H), 8.10–8.05 (m, 1H), 7.95–7.89 (m, 1H), 7.80–7.69 (m, 2H), 7.66–7.57 (m, 1H), 7.53–7.35 (m, 2H), 6.94 (s, 1H), 3.70–330 (m, obscured by solvent signal), 3.29–3.10 (m, 4H), 3.85–2.79 (m, 3H),), MS (posESI) m/z=431(M+H).

Example 123

3,4-Dichloro-N-[1-(4-methyl-piperazin-1-yl)-isoquinolin-3-yl]-benzenesulfonamide, hydrochloride $^1$H NMR (DMSO-d6) δ; 11.17 (s, 1H), 10.50 (br s, 1H), 8.16–8.14 (m, 1H), 7.98–7.93 (m, 1H), 7.91–7.89 (m, 2H), 7.85–7.80 (m, 1H), 7.68–7.60 (m, 1H), 7.49–7.41 (m, 1H), 7.04 (s, 1H), 3.85–3.20 (m, obscured by solvent signal), 2.87–2.83 (m, 3H),), MS (posESI) m/z=451(M+H).

Example 124

4-Methyl-N-[1-(4-methyl-piperazin-1-yl)-isoquinolin-3-yl]-benzenesulfonamide, hydrochloride $^1$H NMR (DMSO-d6) δ; 10.88 (m, brs, 1H), 7.95–7.88 (m, 1H), 7.85–7.74 (m, 3H), 7.65–7.56 (m, 1H), 7.51–7.34 (m, 4H), 7.14–7.09 (m, 1H), 6.99 (s, 1H), 3.75–3.45 (m, obscured by solvent signal, 4H), 3.35–3.15 (m, 4H), 2.84 (d, J=4.75 Hz, 3H), 2.33 (s, 3H),), MS (posESI) m/z=397(M+H).

Example 125

3-Methoxy-N-[1-(4-methyl-piperazin-1-yl)-isoquinolin-3-yl]-benzenesulfonamide, hydrochloride $^1$H NMR (DMSO-d6) δ; 10.93 (brs, 1H), 10.69 (brs, 1H), 7.93 (d, J=8.19 Hz, 1H), 7.79 (d, J=7.92 Hz, 1H), 7.65–7.57 (m, 1H), 7.52–7.37 (m, 4H), 7.24–7.13 (m, 1H), 7.03 (s, 1H), 3.78 (s, 3H), 3.75–3.20 (m, obscured by solvent signal, 8H), 2.81 (d, J=4.48 Hz, 3H), MS (posESI) m/z=413(M+H).

Example 126

5-Chloro-thiophene-2-sulfonic acid [1-(4-methyl-piperazin-1-yl)-isoquinolin-3-yl]-amide, hydrochloride $^1$H NMR (DMSO-d6) δ; 7.76–7.21 (m, 1H), 7.01–6.96 (m, 1H), 6.89–6.82 (m, 1H), 6.74–6.71 (m, 1H), 6.70–6.66 (m, 1H), 6.40 (brs, 1H), 6.22 (d, J=3.96 Hz, 1H), 3.20–3.10 (m, 2H), 2.87–2.75 (m, 2H), 2.70–2.50 (m, obscured in part by solvent signal, 4H), 2.19 (brs, 3H), MS (posESI) m/z=423(M+H).

Example 127

N-{2-Chloro-4-[1-(4-methyl-piperazin-1-yl)-isoquinolin-3-ylsulfamoyl]-phenyl}-acetamide, hydrochloride $^1$H NMR (DMSO-d6) δ; 10.03 (s, 1H), 10.52 (brs, 1H), 7.93 (d, J=8.44 Hz, 1H), 7.78 (d, J=7.92 Hz, 1H), 7.71 (d, J=2.11 Hz, 1H), 7.65–7.57 (m, 1H), 7.57–7.51 (dd, J=2.11 and 8.44 Hz, 1H), 7.45–7.37 (m, 1H), 6.99 (s, 1H), 6.80 (d, 8.44 Hz, 1H), m3.82–3.71 (m, 2H), 3.60–3.20 (m, obscured by solvent signal)$_{2.84}$ (d, J=4.49 hz, 3H), MS (posESI) m/z=474(M+H).

Example 128

2,5-Dichloro-thiophene-3-sulfonic acid [1-(4-methyl-piperazin-1-yl)-isoquinolin-3-yl]-amide, hydrochloride $^1$H NMR (DMSO-d6) 6; 794–7.89 (m, 1H), 7.77–7.72 (m, 1H), 7.63–7.56 (m, 1H), 7.46 (s, 1H), 7.44–7.36 (m, 1H), 3.50–3.20 (m, obscured by solvent signal), 2.70–2.50 m, obscured by solvent signal), 2.32 (brs, 3H), MS (posESI) m/z=457(M+H).

Example 129

N-[1-(4-Methyl-piperazin-1-yl)-isoquinolin-3-yl]-3-trifluoromethyl-benzenesulfonamide, hydrochloride $^1$H NMR (DMSO-d6) δ; 11.17 (s, 1H), 10.71 (brs, 1H), 8.27–8.17 (m, 2H), 8.07–8.01 (m, 1H), 7.97–7.79 (m, 3H), 7.67–7.60 (m, 1H), 7.48–7.40 (m, 1H), 7.06 (s, 1H), 3.70–3.40 (m, m, obscured by solvent signal), 3.31–3.14 (m, 4H), 2.82 (d, J=4.75 Hz, 3H), MS (posESI) m/z=451 (M+H).

Example 130

N-[1-(4-Methyl-piperazin-1-yl)-isoquinolin-3-yl]-4-phenoxy-benzenesulfonamide, hydrochloride $^1$H NMR (DMSO-d6) δ; 10.91 (s, 1H), 10.79 (brs, 1H), 7.98–7.89 (m, 3H), 7.81–7.74 (m, 1H), 7.66–7.55 (m, 1H), 7.49–7.37 (m, 3H), 7.28–7.20 (m, 1H), 7.13–7.06 (m, 4H), 7.00 (s, 1H), 3.77–3.66 (m, 2H), 3.50–3.20 (m, 6H), 2.82 (d, J=4.49 Hz, 3H), MS (posESI) m/z=475 (M+H).

Example 131

5-Bromo-2-methoxy-N-[1-(4-methyl-piperazin-1-yl)-isoquinolin-3-yl]-benzenesulfonamide, hydrochloride $^1$H NMR (DMSO-d6) δ; 10.90 (s, 1H), 10.75 (brs, 1H), 7.99 (d, J=2.64 Hz, 1H), 7.91 (m, d, J=8.45 Hz, 1H), 7.80–7.73 (m, 2H), 7.65–7.57 (m, 1H), 7.45–7.37 (m, 1H), 7.14 (d, J=8.47 Hz, 1H), 3.82 (s, 3H), 3.68–3.55 (m, 2H), 3.52–3.38 (m, 2H), 3.35–3.20 (m, 4H), 2.84 (d, J=4.49 Hz, 3H), MS (posESI) m/z=491(M+H).

Example 132

2-Methanesulphonyl-N-[1-(4-methyl-piperazin-1-yl)-isoquinolin-3-yl]-benzenesulfonamide, hydrochloride MS (posESI) m/z=461 (M+H).

Example 133

3,5-Dimethyl-isoxazole-4-sulfonic acid [1-(4-methyl-piperazin-1-yl)-isoquinolin-3-yl]-amide, hydrochloride $^1$H NMR (DMSO-d6) δ; 11.17 (s, 1H), 10.54 (s, 1H), 7.99 (d, J=8.45 Hz, 1H), 7.86 (d, J=7.92 Hz, 1H), 7.71–7.63 (m, 1H), 7.53–7.45 (m, 1H), 7.07 (s, 3H), 3.75–3.64 (m, 2H), 3.55–3.45 (m, 2H), 3.35–3.15 (m, 4H), 2.84 (d, J=4.49 Hz, 3H), 2.76 (s, 3H), 2.31 (s, 3H), MS (posESI) m/z=402 (M+H).

Example 134

2,4,6-Trimethyl-N-[1-(4-methyl-piperazin-1-yl)-isoquinolin-3-yl]-benzenesulfonamide ¹H NMR (DMSO-d6) δ; 10.82 (s, 1H), 10.52 (brs, 1H), 7.92–7.87 (m, 1H), 7.76–7.70 (m, 1H), 7.64–7.56 (m, 1H), 7.43–7.36 (m, 1H), 7.00 (s, 2H), 6.88 (s, 1H), 6.74 (brs, 1H), is 3.60–3.10 (m, 8H), 2.81 (d, J=4.75 Hz, 3H), 2.61 (s, 6H), 2.22 (s, 3H), MS (posESI) m/z=425 (M+H).

Example 135

3,4-Dimethoxy-N-[1-(4-methyl-piperazin-1-yl)-isoquinolin-3-yl]-benzenesulfonamide, hydrochloride ¹H NMR (DMSO-d6) δ; 10.75 (brs, 1H), 10.72 (s, 1H), 7.95–7.90 (m, 1H), 7.82–7.76 (m, 1H), 7.65–7.57 (m, 1H), 7.55–7.37 (m, 2H), 7.11 (d, J=8.71 Hz, 1H)m 7.05 (s, 1H), 3.78 (s, 3H), 3.76 (s, 3H), 3.76–3.69 (m, obscured in part by —OMe), 3.51–3.19 (m, 6H), 2.82 (d, J=4.49 Hz, 3H), MS (posESI) m/z=443 (M+H).

Synthesis of Examples in Table V

Example 136

N-[8-(4-Methyl-1-piperazinyl)-5-quinolinyl]benzenesulfonamide, hydrochloride

To a solution of 8-(4-methyl-1-piperazinyl)-5-nitroquinoline (0.379 g, 1.39 mmol) in THF:EtOH 1:4 solvent system was added Raney-Ni (1.0 mL suspension in EtOH) followed by hydrazine hydrate (0.348 g, 6.95 mmol). The mixture was stirred vigorously at room temperature for 16 hours and then filtered through celite pretreated with water. The filtrate was concentrated, and the residue was purified by column chromatography (SiO₂, CHCl₃/MeOH/NH₃ 9:1:0.4%) to give 0.337 g of 8-(4-methyl-1-piperazinyl)-5-quinolinylamine. The amine was dissolved in CH₂Cl₂ (6.0 mL) and pyridine (0.785 mL, 9.73 mmol) and benzenesulfonyl chloride (0.178 mL, 1.39 mmol) was added. The reaction mixture was stirred at room temperature for 16 hours and then washed with saturated aqueous NaHCO₃. The organic phase was dried with Na₂SO₄, filtered and concentrated. The crude product was purified by column chromatography (SiO₂, CHCl₃/MeOH/NH₃ 9:1:0.4%) to give 0.130 g of the free base which was converted to its HCl-salt: ¹H NMR (DMSO-d6) δ; 11.09 (br s, 1H), 10.32 (s, 1H), 8.94–8.89 (m, 1H), 8.55–8.48 (m, 1H), 7.68–7.65 (m, 2H), 7.64–7.57 (m, 2H), 7.54–7.49 (m, 2H), 7.27–7.22 (m, 1H), 7.12–7.08 (m, 1H), 3.95–3.84 (m, 2H), 3.55–3.49 (m, 2H), 3.45–3.35 (m, 2H), 3.26–3.16 (m, 2H), 2.85–2.82 (m, 3); MS (posESI) m/z 383 (M+H).

Syntehsis of Examples and Intermediates in Table VI

Scheme 3

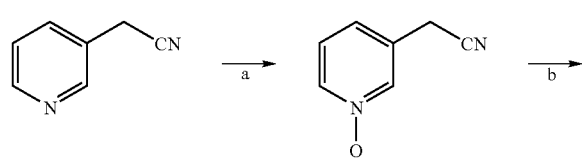

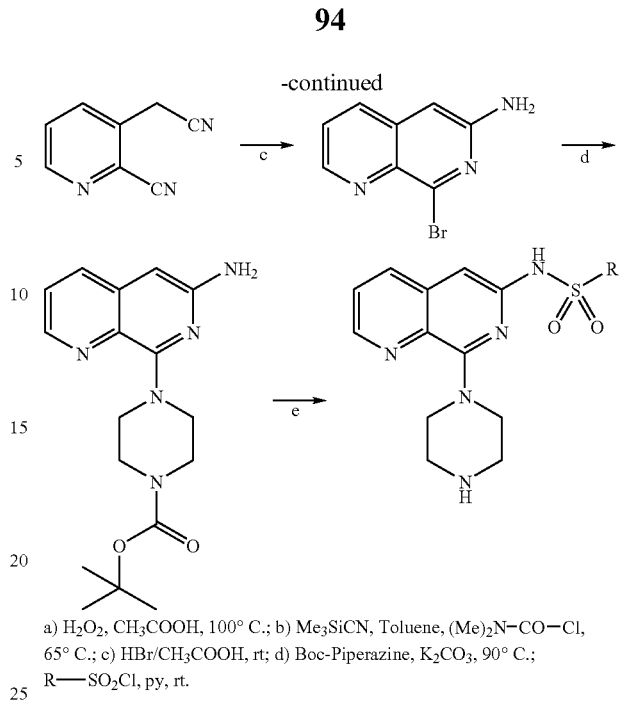

a) H₂O₂, CH₃COOH, 100° C.; b) Me₃SiCN, Toluene, (Me)₂N—CO—Cl, 65° C.; c) HBr/CH₃COOH, rt; d) Boc-Piperazine, K₂CO₃, 90° C.; R—SO₂Cl, py, rt.

Intermediate 20

3-Cyanomethylpyridine-N-oxide—Hydrogenperoxide (17 ml, 30% ww) was added to a mixture of 3-cyanomethylpyridine (11 g, 93 mmol) and glacial acetic acid (55 ml) and heated at 100° C. overnight. The mixture was diluted with water (70 ml) and MnO₂ (5.0 g) was carefully added and stirred for 5 hours (check peroxide content with peroxide sticks), and only small amounts of peroxide was left. The mixture was concentrated in vacuo to 40 ml and diluted with methanol (40 ml), filtered through a short plug of silica, and washed with methanol (400 ml). The filtrate were concentrated and recrystallized from chloroform and hexane to give the title compound (9.5 g, 76%). ¹H NMR (CDCl₃) δ 8.16 (s, 2H), 7.32 (s, 2H), 3.73 (s, 2H); MS m/z (M+1)135.

Intermediate 21

3-(Cyanomethyl)pyridine-2-carbonitrile—Trimethylsilylcyanide (4.2 ml, 32 mmol) was added to a suspension of 3-cyanomethylpyridine-N-oxide (3.5 g, 26 mmol) in toluene (35 ml) and after 1 minute dimethylcarbamylchloride (2.4 ml, 26 mmol) was added and the reaction was stirred overnight at 65° C. EtOAc and 1N NaOH was added and the mixture was washed with water (2×). The organic phase was dried (MgSO₄) and evaporated. The crude product was dissolved in ethanol (150 ml) and stirred overnight, filtered (remove byproduct) and concentrated (25 ml). After 30 min at 0° C. the yellow powder was filtered and washed with cold ethanol (1×) to give, after drying, the title compound (2.15 g, 57%). ¹H NMR (CDCl₃) δ 8.71 (m, 1H), 8.03 (d, J=8.03 Hz, 1H), 7.62 (dd, J=8.16, 4.64 Hz, 1H), 4.04 (s, 2H); MS m/z (M−1) 142.

Intermediate 22

6-Amino-8-bromo-1,7-naphthyridine—3-(Cyanomethyl)pyridine-2-carbonitrile (4.0 g, 28 mmol) was added carefully to HBr in acetic acid (33%) (25 ml) at rt. The red suspension was stirred for 1.5 h and filtered. The red solid was washed with EtOAc (3×) and suspended in water. 1N NaOH was added dropwise until pH-8, and the suspension was stirred for 45 minutes and filtered. The red solid was washed with water (2×) and dried. The crude product was suspended in 5% MeOH in CH$_2$Cl$_2$ and filtered through a short plug of silica, washing with 5% MeOH in CH$_2$Cl$_2$. Subsequent concentration in vacuo afforded the title compound (3.85 g, 61%). $^1$H NMR (DMSO) δ 8.58 (dd, J=4.02, 1.51 Hz, 1H), 8.01 (dd, J=8.53, 1.51 Hz, 1H), 7.47 (dd, J=8.53, 4.02 Hz, 1H), 6.58 (s, 1H), 6.48 (s, 2H); MS m/z (M+1) 226.

Intermediate 23 tert-Butyl 4-(6-amino-1,7-naphthyridin-8-yl)piperazine-1-carboxylate—A mixture of 6-amino-8-bromo-1,7-naphthyridine (650 mg, 2.9 mmol), BOC-piperazine (1.1 g, 5.9 mmol), potassium carbonate (2 g, 15 mmol) in DMSO (1 ml) was stirred at 90° C. for 3 days. Chloroform was added, the mixture was filtered and the filtrate was washed with brine (3×100 ml). The organic phase was dried using potassium carbonate, filtered and concentrated in vacuo to give a yellow oil. The oil was triturated with diethyl ether and then eluted through a short silica plug using chloroform. Subsequent concentration of the residue in vacuo gave the title compound (700 mg, 74%) as a yellow oil. $^1$H NMR (CDCl$_3$) δ 8.43 (dd, J=4.09, 1.72 Hz, 1H), 7.67 (dd, J=8.31, 1.72 Hz, 1H), 7.25–7.20 (m, 1H), 6.08 (s, 1H), 4.29 (s, 2 H), 3.95–3.88 (m, 4H), 3.65–3–57 (m, 4H), 1.46 (s, 9 H); MS m/z (M+1) 330.

General Procedure I

To a stirred solution of tert-butyl 4-(6-amino-1,7-naphthyridin-8-yl)piperazine-1-carboxylate (63 mg, 0.19 mmol) in anhydrous dichloromethane (0.5 ml) and pyridine (0.25 ml) was added p-toluenesulfonyl chloride (36 mg, 0.19 mmol). The reaction mixture was stirred at room temperature over night and then concentrated in vacuo. The residue was purified using reversed-phase preparative HPLC to give the corresponding tert-butoxycarbonyl protected piperazine intermediate. This was dissolved in dichloromethane (1.5 ml) and treated with concentrated TFA (1 ml) at room temperature for 1.5 hours.

Example 137

4-Methyl-N-(8-piperazin-1-yl-1,7-naphthyridin-6-yl)benzenesulfonamide, trifluoroacetic acid The title compound was prepared following the general procedure I (61 mg, 65%) as a yellow solid. $^1$H NMR (CD$_3$OD) δ 8.57–8.65 (m, 1H), 8.06–7.98 (m, 1H), 7.86–7.78 (m, 2H), 7.53–7.43 (m, 1H), 7.36–7.26 (m, 2H), 6.88 (s, 1H), 4.18–4.06 (m, 4H), 3.35–3.24 (m, 4H), 2.35 (s, 3H); MS m/z (M+1) 384.

Example 138

4-Bromo-N-(8-piperazin-1-yl-1,7-naphthyridin-6-yl)benzenesulfonamide, trifluoroacetic acid The title compound was prepared following the general procedure I (14 mg, 13%). $^1$H NMR (CD$_3$OD) δ 8.70–8.63 (m, 1H), 8.14–8.05 (m, 1H), 7.91–7.83 (m, 2H), 7.76–7.67 (m, 2H), 7.57–7.49 (m, 1H), 6.91 (s, 1H), 4.19–4.09 (m, 4H), 3.38–3.28 (m, 4H); MS m/z (M+1) 449.

Example 139

N-(8-Piperazin-1-yl-1,7-naphthyridin-6-yl)naphthalene-1-sulfonamide, trifluoroacetic acid The title compound was prepared following the general procedure 1 (66 mg, 65%). $^1$H NMR (CD$_3$OD) δ 8.82–8.76 (m, 1H), 8.58–8.54 (m, 1H), 8.42–8.37 (m, 1H), 8.13–8.07 (m, 1H), 8.01–7.92 (m, 2H), 7.71–7.54 (m, 3H), 7.47–7.40 (m, 1H), 6.80 (s, 1H), 4.02–3.96 (m, 4H), 3.24–3.18 (m, 4H); MS m/z (M+1) 420.

Example 140

N-(8-Piperazin-1-yl-1,7-naphthyridin-6-yl)butane-1-sulfonamide, trifluoroacetic acid The title compound was prepared following the general procedure I (48 mg, 55%). $^1$H NMR (CD$_3$OD) δ 8.71–8.66 (m, 1H), 8.13–8.06 (m, 1H), 7.58–7.51 (m, 1H), 6.83 (s, 1H), 4.33–4.23 (m, 4H), 3.51–3.38 (m, 6H), 1.91–1.72 (m, 2H), 1.53–1.38 (m, 2H), 0.98–0.86 (m, 3H); MS m/z (M+2) 351.

Example 141

3-Trifluoromethyl-N-(8-piperazin-1-yl-1,7-naphthyridin-6-yl)benzenesulfonamide, trifluoroacetic acid The title compound was prepared following the general procedure 1 (60 mg, 57%). $^1$H NMR (CD$_3$OD) δ 8.70–8.63 (m, 1H), 8.28–8.17 (m, 2H), 8.13–8.05 (m, 1H), 7.96–7.87 (m, 1H), 7.80–7.69 (m, 1H), 7.58–7.48 (m, 1H), 6.93 (s, 1H), 4.18–4.07 (m, 4H), 3.39–3.27 (m, 4H); MS m/z (M+1) 438.

Example 142

3,4-Dimethoxy-N-(8-piperazin-1-yl-1,7-naphthyridin-6-yl)benzenesulfonamide, trifluoroacetic acid The title compound was prepared following the general procedure 1 (65 mg, 63%). $^1$H NMR (CD$_3$OD) δ 8.68–8.59 (m, 1H), 8.11–8.01 (m, 1H), 7.61–7.40 (m, 3H), 7.04–6.92 (m, 2H), 4.22–4.10 (m, 4H), 3.81 (s, 3H), 3.78 (s, 3H), 3.39–3.27 (m, 4H); MS m/z (M+1) 430.

Example 143

2,4-Dichloro-N-(8-piperazin-1-yl-1,7-naphthyridin-6-yl)benzenesulfonamide, trifluoroacetic acid The title compound was prepared following the general procedure 1 (56 mg, 53%). $^1$H NMR (CD$_3$OD) δ 8.66–8.61 (m, 1H), 8.25–8.20 (m, 1H), 8.06–8.00 (m, 1H), 7.65–7.61 (m, 1H), 7.57–7.47 (m, 2H), 6.76 (s, 1H), 4.13–4.06 (m, 4H), 3.36–3.28 (m, 4H); MS m/z (M+2) 439.

Example 144

N-(8-Piperazin-1-yl-1,7-naphthyridin-6-yl)thiophene-2-sulfonamide, trifluoroacetic acid The title compound was prepared following the general procedure 1 (57 mg, 61%). $^1$H NMR (CD$_3$OD) δ 8.71–8.64 (m, 1H), 8.14–8.05 (m, 1H), 7.76–7.67 (m, 2H), 7.58–7.49 (m, 1H), 7.11–7.03 (m, 1H), 6.98 (s, 1H), 4.27–4.15 (m, 4H), 3.40–3.28 (m, 4H); MS m/z (M+1) 376.

Example 145

1-Phenyl-N-(8-piperazin-1-yl-1,7-naphthyridin-6-yl)methanesulfonamide, trifluoroacetic acid The title compound was prepared following the general procedure 1 (35 mg, 37%). $^1$H NMR (DMSO) δ 8.83 (br s, 1H), 8.52–8.40 (m, 2H), 7.47–7.41 (m, 1H), 7.29–7.10 (m, 6H), 6.87 (s, 1H), 4.52 (s, 2H), 4.39–4.31 (m, 4H), 3.30–3.22 (m, 4H); MS m/z (M+1) 384.

Synthesis of Examples and Intermadiates in Table

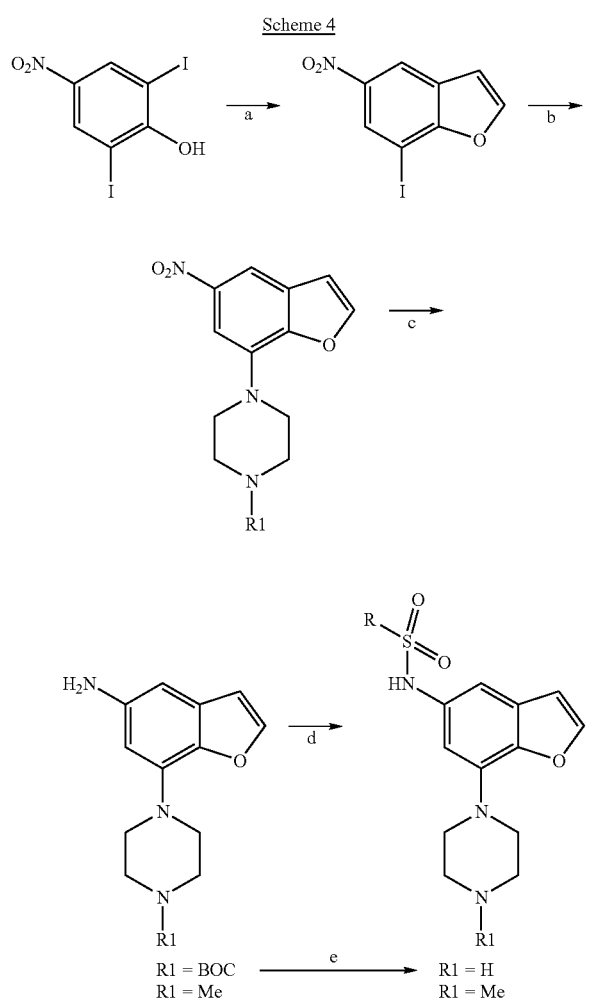

Scheme 4 a) TMS-acethylene, Cu2O, Py, 80° C.; b) tBuO-Na, Pd2(dba)3, Xantphos, xilene, 120° C.; c) Raney-Ni, Hydrazine, THF/Ethanol; d) R—SO2—Cl, Py; e) HCl-diethy ether.

Intermediate 24

7-Iodo-5-nitro-1-benzofuran—A mixture of 4-nitro-2,5-diiodophenol (7.68 g, 6.86 mmol), TMS-acetylene (0.67 g, 6.86 mmol) and Cu$_2$O (0.59 g, 4.12 mmol) in pyridine (120 mL) was heated to 80 C for 48 h. The mixture was filtered through celite and the solvent was removed. Column chromatography DCM/heptane 1:1 gave 0.35 g (18%) of product. $^1$HNMR (CD$_3$OD) δ 8.60 (d, 1H, j=2.1 Hz), 8.51 (d, 1H, J=2.1 Hz), 7.84 (d, 1H, J=2.1 Hz), 7.04 (d, 1H, J=2.4 Hz); MS (ESI) 289.8 (M+H)$^+$; Purity (HPLC, column X) 93%.

Interemediate 25

1-Methyl-4-(5-Nitro-1-benzofuran-7-yl)-piperazine—A mixture of 7-iodo-5-nitro-1-benzofuran (94.5 mg, 0.327 mmol), Xantphos (19 mg. 0.032 mmol), Pd$_2$(dba)$_3$ (7.4 mg, 0.025 mmol) and NaOt-Bu (44.0 mg, 0.458 mmol), methylpiperazine (39.3 mg, 0.392 mmol) in xylene (3 mL) was heated to 120° C. overnight. The mixture was diluted with DCM and filtered through silica. The product was elueed with DCM/MeOH×0.4% NH$_3$. Flash chromatography (DCM/MeOH×0.4% NH$_3$) gave 60 mg (70%) of BVT: $^1$HNMR (CD$_3$OD) δ 8.07 (d, 1H, J=2.1 Hz), 7.70 (d, 1H, J=2.1 Hz), 7.58 (d, 1H, J=2.1 Hz), 6.84 (d, 1H, J=2.1 Hz), 3.44–3.40 (m, 4H), 2.65–2.62 (m, 4H), 2.36 (s, 3H); MS (ESI) 262.0 (M+H)$^+$; Purity (HPLC, column X) 95%.

Intermediate 26 tert-Butyl 4-(5-nitro-1-benzofuran-7-yl)-piperazine-1-carboxylate—The title compound was prepared according to the same procedure used for Intermediate 25 using N-tert-butyl-piperazine carboxylate to afford 240 mg (64%) of a white solid: $^1$HNMR (CD$_3$OD) δ 8.08 (d, 1H, J=2.1 Hz), 7.72 (d, 1H, J=2.1 Hz), 7.58 (d, 1H, J=2.1 Hz), 6.86 (d, 1H, J=2.1 Hz), 3.66–3.62 (m, 4H), 3.34–3.31 (m, 4H), 1.46 (s, 9H); MS (ESI) 370.0 (M+Na)$^+$; Purity (HPLC, column X) 96%.

Intermediate 27

1-Methyl-4-(5-amino-1-benzofuran-7-yl)-piperazine

Intermediate 28 tert-Butyl 4-(5-amino-1-benzofuran-7-yl)-piperazine-1-carboxylate—1-Methyl-4-(5-Nitro-1-benzofuran-7-yl)-piperazine (1 eq) and tert-butyl 4-(5-nitro-1-benzofuran-7-yl)-piperazine-1-carboxylate (1 eq) were reduced to aromatic amine with Raney-Ni and hydrazine (10 eq) in THF/Ethanol (1:4), 3 h at room temperature. The reaction mixture are filtered through celite pad, the volatiles are evaporated and the crude is used in the next reactions.

Example 146

3-Cyanophenyl-N-(7-piperazin-1-yl-benzofuran-5-yl)-benzenesulfonamide, hydrochloride To a solution of tert-butyl 4-(5-amino-1-benzofuran-7-yl)-piperazine-1-carboxylate (43 mg 0.138 mmol) and pyridine (100 μL, 1.24 mmol) was added 3-cyanobenzenesulfonylchloride (33.4 mg, 0.166 mmol). After 2 h PS-Trisamin was added and the reaction was stirred overnight. Flash chromatography (DCM/Heptane/MeOH 5:4:1) gave 24.6 mg of a solid. The crude product was dissolved in MeOH (2 mL) and HCl/ether 2M (4 mL) was added. After 0.5 h the sample was concentrated to afford 19 mg (36%) of a white solid: $^1$HNMR (CD$_3$OD) δ 8.02–7.88 (m, 3H), 7.72 (d, 1H, J=2.1 Hz), 7.76–7.61 (m, 1H), 6.92 (d, 1H, J=2.1 Hz), 6.74 (d, 1H, J=2.1 Hz), 6.60 (d, 1H, J=2.1 Hz), 3.52–3.41 (m, 8H); MS (ESI) 381.2 (M+H)$^+$; Purity (HPLC, column X) 95%.

Example 147

4-Phenoxy-N-(7-piperazin-1-yl-benzofuran-5-yl)-benzenesulfonamide, hydrochloride The title compound was prepared according to the method used for the synthesis of Example 146 (21%) of a white solid: $^1$HNMR (CD$_3$OD) δ 7.73 (d, 1H, J=2.1 Hz), 7.69–7.64 (m, 2H), 7.43–7.37 (m, 2H), 7.24–7.17 (m, 1H9, 7.04–6.94 (m, 4H), 6.88 (d, 1H, J=2.1 Hz), 6.74 (d, 1H, J=2.1 Hz), 6.70 (d, 1H, J=2.1 Hz), 3.53–3.41 (m, 8H); MS (ESI) 450.1 (M+H)$^+$; Purity (HPLC, column X) 90%.

Example 148

1-Naphthyl-Phenoxy-N-(7-piperazin-1-yl-benzofuran-5-yl)-benzenesulfonamide, hydrochloride The title compound was prepared according to the method used for the synthesis of Example 146 (30%) of a white solid: $^1$HNMR (CD$_3$OD) δ 8.65 (d, 1H, J=8.8 Hz), 8.03–7.86 (m, 3H), 7.58–7.49 (m, 3 H9, 7.36–7.33 (m, 1H), 6.74 (d, 1H, J=2.2 Hz), 6.53 (d, 1H, J=2.2 Hz), 6.30 (d, 1H, J=2.2 Hz), 3.52–3.41 (m, 8H); MS (ESI) 408.1 (M+H)$^+$; Purity (HPLC) 100%.

Example 149

N-(7-Piperazin-1-yl-benzofuran-5-yl)-benzenesulfonamide, hydrochloride

The title compound was prepared according to the method used for the synthesis of Example 146 (33%) of a white solid: $^1$HNMR (CD$_3$OD) δ 7.72–7.69 (m, 3H), 7.57–7.51 (m, 1H), 7.47–7.41 (m, 2H), 6.92 (d, 1H, J=2.1 Hz), 6.72 (d, 1H, J=2.1 Hz), 6.58 (d, 1H, J=2.1), 3.49–3.39 (m, 8H); MS (ESI) 358.1 (M+H)$^+$; Purity (HPLC) 96%.

Example 150

5-Chloro-3-methyl-benzo[b]thiophene-2-sulfonic acid (7-piperazin-1-yl-benzofuran-5-yl)-amide, hydrochloride The title compound was prepared according to the method used for the synthesis of Example 146 (9%) of a white solid: $^1$HNMR (CD$_3$OD) δ 7.74–7.73 (m, 2H), 7.62 (d, 1H, J=2.2 Hz), 7.38–7.36 (m, 1H), 6.87 (d, 1H, J=1.8 Hz), 6.64 (d, 1H, J=2.2 Hz), 6.58 (d, 1H, J=1.8 Hz), 3.36–3.28 (m, 8H); MS (ESI) 398.2 (M+H)$^+$; Purity (HPLC) 98%.

Example 151

N-[7-(4-methylpiperazin-1-yl)-1-benzofuran-5-yl]-benzenesulfonamide, hydrochloride The title compound was prepared according to the method used for the synthesis of Example 146 using 1-Methyl-4-(5-Nitro-1-benzofuran-7-yl)piperazine (45%) of a white solid: $^1$HNMR (CD$_3$OD) δ 7.74–7.283 (m, 6H), 6.82 (d, 1H, J=1.8 Hz), 6.62 (d, 1H, J=2.2 Hz), 6.48 (d, 1H, J=1.8 Hz), 3.82–2.95 (m, 8H), 2.87 (s, 3H); MS (ESI) 372.1 (M+H)$^+$; Purity (HPLC, column X) 96%.

Example 152

4-Methyl-N-(7-piperazin-1-yl-benzofuran-5-yl)-benzenesulfonamide, hydrochloride 4-(5-Amino-benzofuran-7-yl)-piperazine-1-carboxylic acid tert-butyl ester (44 mg, 0.139 mmol) in 3 ml dichloromethane was added to a tube containing p-toluenesulfonyl chloride (32 mg, 0.167 mmol) together with pyridine (100 μl, 1.25 mmol) and left on a shaker over weekend. After purification by preparative HPLC, the resulting Boc-material was treated with HCl in ether and left on a shaker until the salt had formed. The solution was centrifugated and the supernatant was removed. Ether was added, then centrifugated and decanted (repeated three times) to remove the excess HCl. The remaining ether was finally evaporated in a SpeedVAc concentrator to yield 10 mg of title product. HPLC purity=94%, m/z=372.3 (M+H). 1H NMR (270 MHz, methanol-d4) δ ppm 2.35 (s, 3 H) 3.45 (m, 8 H) 6.63 (d, J=1.85 Hz, 1 H) 6.71 (d, J=2.11 Hz, 1 H) 6.88 (d, J=1.85 Hz, 1 H) 7.25 (m, 2 H) 7.58 (m, 2 H) 7.71 (d, J=2.11 Hz, 1 H).

Example 153

3,4-Dimethoxy-N-(7-piperazin-1-yl-benzofuran-5-yl)-benzenesulfonamide, hydrochloride HPLC purity=92%, m/z=418.3 (M+H). 1H NMR (270 MHz, methanol-d4) δ ppm 3.45 (m, 8 H) 3.70 (m, 3H) 3.81 (m, 3 H) 6.62 (d, J=1.85 Hz, 1 H) 6.73 (d, J=2.38 Hz, 1 H) 6.94 (m, 2 H) 7.17 (d, J=2.11 Hz, 1 H) 7.29 (dd, J=8.44, 2.11 Hz, 1 H) 7.72 (d, J=2.38 Hz, 1 H).

Example 154

4-Bromo-N-(7-piperazin-1-yl-benzofuran-5-yl)-benzenesulfonamide, hydrochloride

HPLC purity=95%, m/z=436.2 (M+H). 1H NMR (270 MHz, methanol-d4) δ ppm 3.46 (m, 8 H) 6.62 (d, J=1.85 Hz, 1 H) 6.74 (d, J=2.38 Hz, 1 H) 6.93 (d, J=1.85 Hz, 1 H) 7.61 (m, 4 H) 7.73 (d, J=2.11 Hz, 1 H).

Example 155

2,3-Dichloro-N-(7-piperazin-1-yl-benzofuran-5-yl)-benzenesulfonamide, hydrochloride HPLC purity=96%, m/z=426.2 (M+H). 1H NMR (270 MHz, methanol-d4) δ ppm 3.44 (m, 8 H) 6.67 (d, J=1.85 Hz, 1 H) 6.72 (d, J=2.11 Hz, 1 H) 7.01 (d, J=1.85 Hz, 1 H) 7.34 (t, J=8.18 Hz, 1 H) 7.70 (m, 2 H) 7.94 (dd, J=7.92, 1.58 Hz, 1 H).

Example 156

2,4-Dichloro-5-methyl-N-(7-piperazin-1-yl-benzofuran-5-yl)-benzenesulfonamide, hydrochloride HPLC purity=96%, m/z=440.2 (M+H). 1H NMR (270 MHz, methanol-d4) δ ppm 2.30 (s, 3 H) 3.46 (m, 8 H) 6.69 (d, J=1.85 Hz, 1 H) 6.73 (d, J=2.11 Hz, 1 H) 7.01 (d, J=1.85 Hz, 1 H) 7.60 (s, 1 H) 7.71 (d, J=2.11 Hz, 1 H) 7.87 (s, 1 H).

Example 157

4-Methoxy-N-(7-piperazin-1-yl-benzofuran-5-yl)-benzenesulfonamide, hydrochloride HPLC purity=93%, m/z=388.3 (M+H). 1H NMR (270 MHz, methanol-d4) δ ppm 3.45 (m, 8 H) 3.79 (s, 3 H) 6.72 (d, J=2.11 Hz, 1 H) 6.93 (m, 3 H) 7.63 (m, 3 H) 7.71 (d, J=2.11 Hz, 1 H).

Example 158

4-Chloro-N-(7-piperazin-1-yl-benzofuran-5-yl)-benzenesulfonamide, hydrochloride

HPLC purity=97%, m/z=392.3 (M+H). 1H NMR (270 MHz, methanol-d4) δ ppm 3.46 (m, 8 H) 6.63 (d, J=1.85 Hz, 1 H) 6.74 (d, J=2.38 Hz, 1 H) 7.47 (m, 2 H) 7.67 (m, 3 H) 7.73 (d, J=2.11 Hz, 1 H).

Example 159

N-(7-Piperazin-1-yl-benzofuran-5-yl)-4-trifluoromethyl-benzenesulfonamide, hydrochloride HPLC purity=91%, m/z=426.3 (M+H). 1H NMR (270 MHz, methanol-d4) δ ppm 3.47 (m, 8 H) 6.64 (d, J=1.85 Hz, 1 H) 6.74 (d, J=2.11 Hz, 1 H) 6.92 (d, J=1.85 Hz, 1 H) 7.73 (d, J=2.11 Hz, 1 H) 7.84 (m, 4 H).

Example 160

5-Fluoro-2-methyl-N-(7-piperazin-1-yl-benzofuran-5-yl)-benzenesulfonamide, hydrochloride HPLC purity=94%, m/z=390.3 (M+H). 1H NMR (270 MHz, methanol-d4) δ ppm 2.57 (m, 3 H) 3.46 (m, 8 H) 6.63 (m, 1 H) 6.74 (d, J=2.11 Hz, 1 H) 6.91 (d, J=1.85 Hz, 1 H) 7.20 (m, 1 H) 7.34 (m, 1 H) 7.56 (dd, J=8.71, 2.64 Hz, 1 H) 7.73 (d, J=2.11 Hz, 1 H).

Example 161

5-Chloro-thiophene-2-sulfonic acid (7-piperazin-1-yl-benzofuran-5-yl)-amide, hydrochloride HPLC purity=94%, m/z=398.3 (M+H). 1H NMR (270 MHz, methanol-d4) δ ppm 3.48 (m, 8 H) 6.68 (d, J=2.11 Hz, 1 H) 6.79 (d, J=2.38 Hz, 1 H) 6.97 (d, J=3.96 Hz, 1 H) 7.01 (d, J=1.85 Hz, 1 H) 7.25 (d, J=3.96 Hz, 1 H) 7.76 (d, J=2.38 Hz, 1 H).

Biological Tests

The ability of a compound according to the invention to bind a $5\text{-HT}_6$ receptor, and to be pharmaceutically useful, can be determined using in vivo and in vitro assays known in the art.

(a) $5\text{-HT}_6$ Intrinsic Activity Assay

Antagonists to the $5\text{-HT}_6$ receptor were characterized by measuring inhibition of 5-HT induced increase in cAMP in HEK 293 cells expressing the human $5\text{-HT}_6$ receptor (see Boess et al. (1997) Neuropharmacology 36: 713–720). Briefly, HEK293/$5\text{-HT}_6$ cells were seeded in polylysine coated 96-well plates at a density of 25,000/well and grown in DMEM (Dulbecco's Modified Eagle Medium) (without phenol-red) containing 5% dialyzed Foetal Bovine Serum for 48 h at 37° C. in a 5% $CO_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 μl dissolved in assay medium, the cells were incubated for 10 min at 37° C. in a 5% $CO_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times $EC_{50}$) evoked increase in cAMP, using the formula $K_i = IC_{50}/(1+[5HT]/EC_{50})$.

The compounds in accordance with the invention have a selective affinity to $5\text{-HT}_6$ receptors with $K_i$ values between 0.5 nM and 5 μM. The compounds show good selectivity for $5\text{-HT}_{1a}$, $5\text{-HT}_{2a}$, $5\text{-HT}_{2a}$, $5\text{-HT}_{2b}$, $5\text{-HT}_{2c}$.

(b) In vivo Assay of Reduction of Food Intake

For a review on serotonin and food intake, see Blundell, J. E. and Halford, J. C. G. (1998) Serotonin and Appetite Regulation. Implications for the Pharmacological Treatment of Obesity. CNS Drugs 9:473–495.

Obese (ob/ob) mouse is selected as the primary animal model for screening as this mutant mouse consumes high amounts of food resulting in a high signal to noise ratio. To further substantiate and compare efficacy data, the effect of the compounds on food consumption is also studied in wild type (C57BL/6J) mice. The amount of food consumed during 15 hours of infusion of compounds is recorded.

Male mice (obese C57BL/6JBom-Lep$^{ob}$ and lean wild-type C57B1/6JBom; Bomholtsgaard, Denmark) 8–9 weeks with an average body weight of 50 g (obese) and 25 g (lean) are used in all the studies. The animals are housed singly in cages at 23±1° C., 40–60% humidity and have free access to water and standard laboratory chow. The 12/12-h light/dark cycle is set to lights off at 5 p.m. The animals are conditioned for at least one week before start of study.

The test compounds are dissolved in solvents suitable for each specific compound such as cyclodextrin, cyclodextrin/methane sulfonic acid, polyethylene glycol/methane sulfonic acid, saline. Fresh solutions are made for each study. Doses of 30, 50 and 100 mg kg$^{-1}$day$^{-1}$ are used. The purity of the test compounds is of analytical grade.

The animals are weighed at the start of the study and randomized based on body weight. Alzet osmotic minipumps (Model 2001D; infusion rate 8 μl/h) are used and loaded essentially as recommended by the Alzet technical information manual (Alza Scientific Products, 1997; Teeuwes and Yam, 1976). Continuous subcutaneous infusion with 24 hours duration is used. The minipumps are either filled with different concentrations of test compounds dissolved in vehicle or with only vehicle solution and maintained in vehicle pre-warmed to 37° C. (approx. 1 h). The minipumps are implanted subcutaneously in the neck/back region under short acting anesthesia (metofane/enflurane). This surgical procedure lasts approximately 5 min. It takes about 3 h to reach steady state delivery of the compound.

The weight of the food pellets are measured at 5 p.m. and at 8 p.m. for two days before (baseline) and one day after the implantation of the osmotic minipumps. The weigh-in is performed with a computer assisted Mettler Toledo PR 5002 balance. Occasional spillage is corrected for. At the end of the study the animals are killed by neck dislocation and trunk blood sampled for later analysis of plasma drug concentrations.

The plasma sample proteins are precipitated with methanol, centrifuged and the supernatant is transferred to HPLC vials and injected into the liquid chromatography/mass spectrometric system. The mass spectrometer is set for electrospray positive ion mode and Multiple Reaction Monitoring (MRM with the transition m/z 316→221). A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the percent basal values. If statistical significance is reached at the level of $p<0.05$, Mann-Whitney U-test for statistical comparison between control and treatment groups is performed.

TABLE VI

In vivo efficacy data on the effect of the compounds on Food Intake reduction

| EXAMPLES | In vivo efficacy - Food intake (15 h) in ob/ob mouse % Inhibition of Food Intake in ob/ob mice at 50 mg/Kg/day, 15 h | Free plasma concentration of the compounds at steady state (Css, u) |
|---|---|---|
| 48 | 23.8 | 0.008 |
| 13 | 24.1 | 0.035 |
| 53 | 25.7[a] | ND |
| 34 | 51.4 | 0.078 |
| 24 | 46.2 | 0.0076 |
| 19 | 69.6 | 0.150 |
| 27 | 68.9 | 0.008 |
| 30 | 60.1 | 0.275 |
| 29 | 71 | 0.33 |
| 14 | 41[b] | 0.23 |

[a]The effect on Food Intake reported in the table was obtained at the dose of 14.8 mg/kg/d
[b]The effect on Food Intake reported in the table was obtained at the dose of 100 mg/kg/d The compounds according to the invention show an effect in the range of 50–200 mg/kg.

What is claimed is:

1. A compound of the formula I

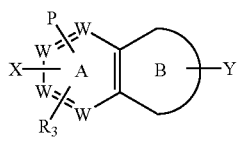

or a pharmaceutically acceptable salt thereof, wherein:
ring B is

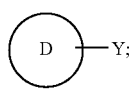

in which D is a five-membered heterocyclic or heteroaryl ring, said ring comprising one or two atoms selected from the group consisting of nitrogen, sulfur and oxygen, with the proviso that when D contains an oxygen atom, D is heteroaryl;
W is —(CH);
P is

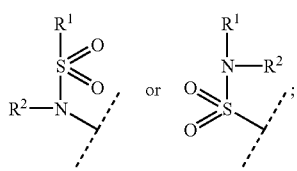

P and $R^3$ are bound to the same ring and are disposed in meta- or para-positions relative to each other;
$R^1$ is
(a) $C_{1-6}$ alkyl,
(b) $C_{1-6}$ alkoxyalkyl,
(c) straight or branched $C_{1-6}$ hydroxyalkyl,
(d) straight or branched $C_{1-6}$ alkylhalides; or
(e) a group Ar;
Ar is
(a) phenyl,
(b) 1-naphthyl,
(c) 2-naphthyl,
(d) benzyl,
(e) cinnamoyl,
(f) a 5 to 7-membered, optionally aromatic, partially saturated or completely saturated, heterocyclic ring containing 1 to 4 heteroatoms, selected from oxygen, nitrogen and sulfur, or
(g) a bicyclic ring system comprising at least one heterocyclic ring according to (f);
wherein the group Ar is substituted in one or more positions with
(a) H, X or Y, or
(b) a 5 to 7-membered, optionally aromatic, partially saturated or completely saturated, heterocyclic ring each containing 1 to 4 heteroatoms selected from oxygen, nitrogen or sulfur;
$R^2$ is
(a) H,
(b) $C_{1-6}$ alkyl,
(c) $C_{1-6}$ alkoxy,
(d) straight or branched $C_{1-6}$ hydroxyalkyl, or
(e) straight or branched $C_{1-6}$ alkylhalides;
or $R^1$ and $R^2$ are linked to form a group $(CH_2)_4O$;
one of $R^3$ is a group

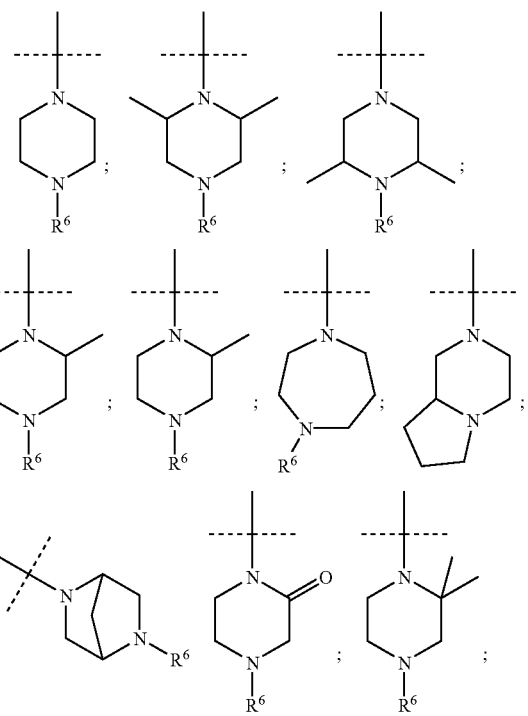

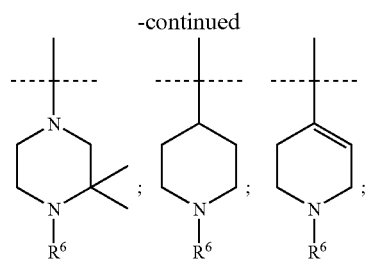

X and Y are independently
(a) H,
(b) halogen,
(c) $C_{1-6}$ alkyl,
(d) —$CF_3$,
(e) hydroxy,
(f) $C_{1-6}$ alkoxy,
(g) $C_{1-4}$ alkenyl,
(h) phenyl,
(i) phenoxy,
(j) benzyloxy,
(k) benzoyl,
(l) —$OCF_3$,
(m) —CN,
(n) straight or branched $C_{1-6}$ hydroxyalkyl,
(o) straight or branched $C_{1-6}$ alkylhalides,
(p) —$NH_2$,
(q) —$NHR^4$,
(r) —$NR^4R^5$,
(s) —$NO_2$,
(t) —$CONR^4R^5$,
(u) —$NHSO_2R^4$,
(v) —$NR^4COR^5$,
(x) —$SO_2NR^4R^5$,
(z) —$C(=O)R^4$,
(aa) —$CO_2R^4$,
(ab) —$S(O)_nR^4$ wherein n is 0, 1, 2 or 3,
(ac) —S—$(C_{1-6})$alkyl, or
(ad) —$SCF_3$;
$R^4$ and $R^5$ are independently
(a) H,
(b) $C_{1-6}$ alkyl,
(c) $C_{3-7}$ cycloalkyl, or
(d) Ar, as defined above for $R^1$;
alternatively, $R^4$ and $R^5$ are linked to form a group $(CH_2)_2O$, $(CH_2)_4O$ or $(CH_2)_{3-5}$; and
$R^6$ is
(a) H, or
(b) straight of branched $C_{1-6}$ alkyl.

2. The compound according to claim 1 of the general formula VI

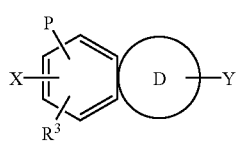

(VI)

wherein $R^3$, P, X and Y are as defined for formula (I) in claim 1; and wherein D is a five-membered heterocyclic or heteroaryl ring, said ring comprising one or two atoms selected from the group consisting of nitrogen, sulfur and oxygen, with the proviso that when D contains an oxygen atom, D is heteroaryl, and wherein when the heteroaryl ring comprises one or two nitrogen atoms, a group $R^6$ is attached at the secondary nitrogen, in which $R^6$ is as defined for formula (I) in claim 1.

3. The compound according to claim 1, wherein
$R^1$ is
(a) $C_{1-6}$ alkyl, or
(e) a group Ar;
Ar is
(a) phenyl,
(b) 1-naphthyl,
(c) 2-naphthyl, or
(f) a 5 to 7-membered, optionally aromatic, partially saturated or completely saturated, heterocyclic ring containing 1 to 4 heteroatoms, selected from oxygen, nitrogen and sulfur;
wherein the group Ar is substituted in one or more positions with X or Y; wherein X or Y is
(a) H,
(b) halogen,
(c) $C_{1-6}$ alkyl,
(d) —$CF_3$,
(f) $C_{1-6}$ alkoxy,
(g) $C_{1-4}$ alkenyl,
(l) —$OCF_3$, or
(n) straight or branched $C_{1-6}$ hydroxyalkyl;
$R^2$ is
(a) H, or
(b) $C_{1-3}$ alkyl;
or $R^1$ and $R^2$ are linked to form a group $(CH_2)_4O$;
$R^3$ is

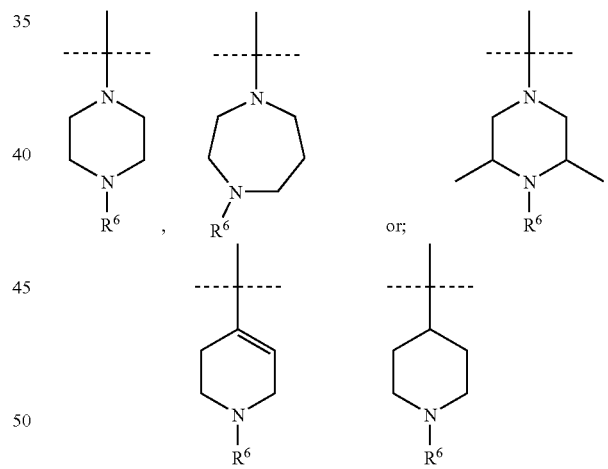

wherein $R^6$ is
(a) H, or
(b) $C_{1-6}$ alkyl; and
D is pyrrolyl, thienyl or furanyl.

4. The compound of claim 3, wherein $R^6$ is methyl.

5. The compound of claim 3, wherein $R^2$ is methyl.

6. The compound according to claim 1, which is the compound 3-Cyanophenyl-N-(7-piperazin-1-yl-benzofuran-5-yl)-benzenesulfonamide, hydrochloride, 4-Phenoxy-N-(7-piperazin-1-yl-benzofuran-5-yl)-benzenesulfonamide, hydrochloride,
1-Naphthyl-N-(7-piperazin-1-yl-benzofuran-5-yl)-benzenesulfonamide, hydrochloride, N-(7-Piperazin-1-yl-benzofuran-5-yl)-benzenesulfonamide, hydrochloride, 5-Chloro-3-methyl-benzo[b]thiophene-2-sulfonic acid (7-piperazin-1-yl-benzofuran-5-yl)-amide hydrochloride, or N-[7-(4-Methylpiperazin-1-yl)-1-benzofuran-5-yl]-benzenesulfonamide, hydrochloride.

7. A pharmaceutical formulation containing a compound according to claim 1 as active ingredient, in combination with a pharmaceutically acceptable diluent or carrier.

8. A method for the treatment of obesity, which comprises administering to a mammal in need of such treatment an effective amount of a compound according to claim 1.

9. A method for the treatment of obesity, which comprises administering to a mammal in need of such treatment an effective amount of a compound according to claim 2.

10. A method for the treatment of obesity, which comprises administering to a mammal in need of such treatment an effective amount of a compound according to claim 6.

11. A method for the treatment of type II diabetes, which comprises administering to a mammal in need of such treatment an effective amount of a compound according to claim 1.

12. A method for the treatment of type II diabetes, which comprises administering to a mammal in need of such treatment an effective amount of a compound according to claim 2.

13. A method for the treatment of type II diabetes, which comprises administering to a mammal in need of such treatment an effective amount of a compound according to claim 6.

14. A method for the treatment of binge disorders, which comprises administering to a mammal in need of such treatment an effective amount of a compound according to claim 1.

15. A method for the treatment of binge disorders, which comprises administering to a mammal in need of such treatment an effective amount of a compound according to claim 2.

16. A method for the treatment of binge disorders, which comprises administering to a mammal in need of such treatment an effective amount of a compound according to claim 6.

17. A method for reducing body-weight or reducing food intake, comprising administering to a subject in need thereof an effective amount of a compound according to claim 1.

18. A method for reducing body-weight or reducing food intake, comprising administering to a subject in need thereof an effective amount of a compound according to claim 2.

19. A method for reducing body-weight or reducing food intake, comprising administering to a subject in need thereof an effective amount of a compound according to claim 6.

* * * * *